(12) United States Patent
Saitoh et al.

(10) Patent No.: US 7,468,443 B2
(45) Date of Patent: Dec. 23, 2008

(54) ALKYL ETHER DERIVATIVES OR SALTS THEREOF

(75) Inventors: Akihito Saitoh, Toyama (JP); Noboru Iwakami, Takaoka (JP); Tamotsu Takamatsu, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/416,321

(22) Filed: May 3, 2006

(65) Prior Publication Data

US 2006/0194781 A1 Aug. 31, 2006

Related U.S. Application Data

(62) Division of application No. 10/492,774, filed as application No. PCT/JP02/10827 on Oct. 18, 2002, now Pat. No. 7,087,594.

(30) Foreign Application Priority Data

Oct. 19, 2001 (JP) ............... 2001-321381

(51) Int. Cl.
- *C07D 409/00* (2006.01)
- *C07D 405/00* (2006.01)
- *A01N 43/40* (2006.01)
- *A01N 43/38* (2006.01)

(52) U.S. Cl. ............. 548/525; 546/202; 514/324; 514/422

(58) Field of Classification Search ............... None
See application file for complete search history.

(56) References Cited

U.S. PATENT DOCUMENTS

| | | | |
|---|---|---|---|
| 6,008,233 A | * | 12/1999 | Andino et al. ............ 514/327 |
| 2005/0250843 A1 | | 11/2005 | Nakada et al. |
| 2006/0205709 A1 | * | 9/2006 | Kimura et al. ......... 514/210.19 |

FOREIGN PATENT DOCUMENTS

| | | |
|---|---|---|
| EP | 0 790 245 A1 | 8/1997 |
| JP | 3-232830 | 10/1991 |
| JP | 4-95070 | 3/1992 |
| WO | 96/12717 | 5/1996 |
| WO | 99/31056 | 6/1999 |
| WO | 00-76957 | 12/2000 |

OTHER PUBLICATIONS http://mw1.merriam-webster.com/dictionary (1 page only).*
Society for Neuroscience, Abstracts, vol. 24, Part 1, p. 228, 1998.
Ono et al., (1999), "Alkyl Ether Derivatives or Salt Thereof and Calcium Antagonist Inclusive of the Same," Schreiber Translations.

* cited by examiner

*Primary Examiner*—Kamal A Saeed
*Assistant Examiner*—Sun Jae Y Loewe
(74) *Attorney, Agent, or Firm*—Oblon, Spivak, McClelland, Maier & Neustadt, P.C.

(57) ABSTRACT

An alkyl ether derivative represented by the general formula:

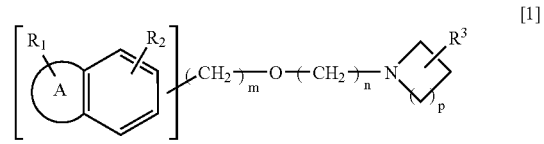

wherein each of $R^1$ and $R^2$ represents one or more groups selected from a hydrogen atom, a halogen atom, an alkyl group, an aryl group, an aralkyl group, an alkoxy group, an aryloxy group, an alkylthio group, an arylthio group, an alkenyl group, an alkenyloxy group, an amino group, an alkylsulfonyl group, an arylsulfonyl group, a carbamoyl group, a heterocyclic group, a hydroxyl group, a carboxyl group, a nitro group, an oxo group and the like; $R^3$ is an alkylamino group, an amino group, a hydroxyl group or the like; the ring A is a 5-membered or 6-membered heteroaromatic ring or a benzene ring; each of m and n is an integer of 1 to 6; and p is an integer of 1 to 3, or its salt has activity to protect neurons, activity to accelerate nerve regeneration and activity to accelerate neurite extension and hence is useful as a therapeutic agent for diseases in central and peripheral nerves.

3 Claims, No Drawings

ALKYL ETHER DERIVATIVES OR SALTS THEREOF

TECHNICAL FIELD

The present invention relates to novel alkyl ether derivatives or their salts, a process for production thereof, intermediates thereof and a therapeutic agent for central and peripheral nerves.

BACKGROUND ART

Dementia is divided into cerebrovascular dementia and neurodegenerative dementia, and various agents such as cerebral blood flow improvers and nootropics are used for treating these dementias.

Senile plaques characteristic of Alzheimer's disease, which is most typical as neurodegenerative dementia, are mainly composed of amyloid β protein (Aβ) derived from β amyloid precursor protein. Aβ is considered as a substance that is deposited on the neurons or blood vessels of brain to cause a disease such as dementia. In addition, it has been reported that Aβ itself injures neurons. Inhibitors of neurotoxicity induced by Aβ are investigated as therapeutic agents for Alzheimer's disease.

As compounds having inhibitory activity against neurotoxicity induced by Aβ, there are known, for example, the 1,2-ethanediol derivatives disclosed in JP-A-3-232830 and JP-A-4-95070, and the N-alkoxyalkyl-N,N-dialkylamine derivatives disclosed in International Publication WO 00/76957.

The 1,2-ethanediol derivatives disclosed in JP-A-3-232830 and JP-A-4-95070, in particular, (R)-1-(benzo[b]thiophen-5-yl)-2-[2-(N,N-diethylamino)ethoxy]ethanol hydrochloride has protective activity against the neuronal death caused by Aβ (SOCIETY FOR NEUROSCIENCE, Abstracts, Vol. 24, Part 1, p. 228, 1998) and activity to enhance the activity of nerve growth factor (NGF) (WO 96/12717) and hence is useful as a therapeutic agent for diseases in central and peripheral nerves. However, there is desired the development of a compound possessing properties such as a higher activity to protect neurons and a higher activity to accelerate nerve regeneration, which are required as a therapeutic agent for diseases in central and peripheral nerves.

DISCLOSURE OF THE INVENTION

The present inventors earnestly investigated in order to solve the above problem, and consequently found that there are compounds having not only calcium-antagonistic activity but also inhibitory activity against neurotoxicity induced by Aβ, among the alkyl ether derivatives with calcium-antagonistic activity disclosed in WO 99/31056.

The present inventors further investigated, and consequently found that an alkyl ether derivative represented by the following general formula [1]:

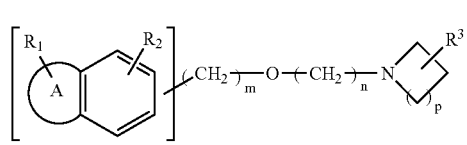

wherein each of $R^1$ and $R^2$, which may be the same or different, represents one or more groups selected from a hydrogen atom, a halogen atom, a substituted or unsubstituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, a protected or unprotected amino, hydroxyl or carboxyl group, a nitro group, and an oxo group; $R^3$ is a substituted or unsubstituted alkylamino group, or a protected or unprotected amino or hydroxyl group; the ring A is a 5-membered or 6-membered heteroaromatic ring or a benzene ring; each of m and n is an integer of 1 to 6; and p is an integer of 1 to 3, or its salt has activity to protect neurons, activity to accelerate nerve regeneration and activity to accelerate axon extension, is excellent in stability to metabolism, and is useful as a therapeutic agent for diseases in central and peripheral nerves, whereby the present invention has been accomplished.

The present invention is explained below in detail.

The terms used in the present specification have the following meanings unless otherwise specified. The term "halogen atom" means a fluorine atom, a chlorine atom, a bromine atom or an iodine atom; the term "alkyl group" means a straight chain or branched chain $C_{1-12}$alkyl group such as methyl, ethyl, propyl, isopropyl, butyl, isobutyl, tert-butyl, pentyl, hexyl, heptyl, octyl or the like; the term "lower alkyl group" means a straight chain or branched chain $C_{1-6}$alkyl group such as methyl, ethyl, propyl, isopropyl, butyl, isobutyl, tert-butyl, pentyl, hexyl or the like; the term "alkoxy group" means a straight chain or branched chain $C_{1-12}$alkyloxy group such as methoxy, ethoxy, propoxy, isopropoxy, butoxy, isobutoxy, tert-butoxy, pentyloxy, hexyloxy, heptyloxy, octyloxy or the like; the term "lower alkoxy group" means a straight chain or branched chain $C_{1-6}$alkyloxy group such as methoxy, ethoxy, propoxy, isopropoxy, butoxy, isobutoxy, tert-butoxy, pentyloxy, hexyloxy or the like; the term "alkenyl group" means a $C_{2-12}$alkenyl group such as vinyl, propenyl, butenyl, pentenyl, hexenyl, heptenyl, octenyl or the like; the term "lower alkenyl group" means a $C_{2-6}$alkenyl group such as vinyl, propenyl, butenyl, pentenyl, hexenyl or the like; the term "alkenyloxy group" means a $C_{2-12}$alkenyloxy group such as vinyloxy, propenyloxy, butenyloxy, pentenyloxy, hexenyloxy heptenyloxy, octenyloxy or the like; the term "lower alkenyloxy group" means a $C_{2-6}$alkenyloxy group such as vinyloxy, propenyloxy, butenyloxy, pentenyloxy, hexenyloxy or the like; the term "alkynyl group" means a $C_{2-6}$alkynyl group such as ethynyl, 2-propynyl, 2-bytynyl or the like; the term "cycloalkyl group" means a cyclopropyl, cyclobutyl, cyclopentyl or cyclohexyl group; the term "alkylthio group" means a $C_{1-12}$alkylthio group such as methylthio, ethylthio, propylthio, isopropylthio, butylthio, isobutylthio, tert-butylthio, pentylthio, hexylthio, heptylthio, octylthio or the like; the term "lower alkylthio group" means a $C_{1-6}$alkylthio group such as methylthio, ethylthio, propylthio, isopropylthio, butylthio, isobutylthio, tert-butylthio, pentylthio, hexylthio or the like; the term "aryl group" means a phenyl, naphthyl, indanyl or indenyl group; the term "aryloxy group" means a phenyloxy, naphthyloxy, indanyloxy or indenyloxy group; the term "aralkyl group" means an ar-$C_{1-6}$alkyl group such as benzyl, diphenylmethyl, trityl, phenethyl or the like; the term "arylthio group" means a phenylthio, naphthylthio, indanylthio or indenylthio group; the term "acyl group" means a formyl group, a $C_{2-12}$alkanoyl group such as acetyl, isovaleryl, propionyl, pivaloyl or the like, an aralkylcarbonyl group such as benzylcarbonyl or the like, or an aroyl group such as benzoyl, naphthoyl or the like; the term "alkylsulfonyl group" means a $C_{1-12}$alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, heptylsulfonyl, octylsulfonyl or the like; the term "lower alkylsulfonyl group" means a $C_{1-6}$alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl or the like; the term "arylsulfonyl group" means a phenylsulfonyl, p-toluenesulfonyl or naphthylsulfonyl group or the like; the term "lower alkylsulfonyloxy group" means a $C_{1-6}$alkylsulfonyloxy group such as methylsulfonyloxy, ethylsulfonyloxy, propylsulfonyloxy, isopropylsulfonyloxy, butylsulfonyloxy, isobutylsulfonyloxy, sec-butylsulfonyloxy, tert-butylsulfonyloxy, pentylsulfonyloxy or the like; the term "arylsulfonyloxy group" means a phenylsulfonyloxy, p-toluenesulfonyloxy or naphthylsulfonyloxy group or the like; the term "alkylamino group" means a mono- or di-$C_{1-6}$alkylamino group such as a methylamino, ethylamino, propylamino, isopropylamino, butylamino, dimethylamino, diethylamino, diisopropylamino, dibutylamino or the like; the term "monoalkylamino group" means a mono-$C_{1-6}$alkylamino group such as methylamino, ethylamino, propylamino, isopropylamino, butylamino or the like; the term "dialkylamino group" means a di-$C_{1-6}$alkylamino group such as dimethylamino, diethylamino, diisopropylamino, dibutylamino or the like; the term "heterocyclic group" means a 5-membered or 6-membered heterocyclic group containing at least one heteroatom selected from nitrogen, oxygen and sulfur atoms or a condensed or crosslinked heterocyclic group thereof, such as pyrrolidinyl, piperidinyl, piperazinyl, homopiperazinyl, homopiperidinyl, morpholyl, thiomorpholyl, tetrahydroquinolyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl, 1,4-benzodioxanyl or the like; and the term "cyclic amino group" means a 5-membered, 6-membered or 7-membered cyclic amino group which contains one or more nitrogen atoms as the heteroatoms forming the ring and may further contain one or more oxygen atoms or sulfur atoms or a condensed or crosslinked cyclic amino group thereof, such as pyrrolidinyl, piperidinyl, piperazinyl, homopiperazinyl, homopiperidinyl, morpholyl, thiomorpholyl, tetrahydroquinolyl, tetrahydroisoquinolyl, imidazolidinyl or the like.

As the 5-membered or 6-membered heteroaromatic ring as the ring A, there are exemplified 5-membered or 6-membered heteroaromatic rings which contain at least one heteroatom selected from oxygen, nitrogen and sulfur atoms as the heteroatom forming the ring, such as triazine, pyridazine, pyrimidine, pyrazine, pyridine, furan, thiophene, pyrrole, oxazole, thiazole, imidazole, isoxazole, isothiazole, pyrazole, pyran, and the like.

As the substituent of each of the alkyl group, aryl group, aralkyl group, alkoxy group, aryloxy group, alkylthio group, arylthio group, alkenyl group, alkenyloxy group, amino group, alkylsulfonyl group, arylsulfonyl group, carbamoyl group and heterocyclic group for each of $R^1$ and $R^2$ and the alkylamino group for $R^3$, there are exemplified groups selected from halogen atoms, lower alkyl groups, cycloalkyl groups, aryl groups, lower alkoxy groups, aryloxy groups, lower alkylthio groups, arylthio groups, lower alkenyl groups, lower alkylsulfonyl groups, arylsulfonyl groups, alkylamino groups, protected or unprotected amino groups, protected or unprotected hydroxyl groups, protected or unprotected carboxyl groups, acyl groups, heterocyclic groups, etc.

The protecting group for the carboxyl group includes all conventional groups usable as carboxyl-protecting groups, for example, lower alkyl groups such as methyl, ethyl, propyl, isopropyl, 1,1-dimethylpropyl, butyl, tert-butyl and the like; aryl groups such as phenyl, naphthyl and the like; ar-lower alkyl groups such as benzyl, diphenylmethyl, trityl, 4-nitrobenzyl, 4-methoxybenzyl, bis(4-methoxyphenyl)methyl and the like; acyl-lower alkyl groups such as acetylmethyl, benzoylmethyl, 4-nitrobenzoylmethyl, 4-bromobenzoylmethyl, 4-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichloroethyl and the like; lower alkylsilyl-lower alkyl groups such as 2-(trimethylsilyl)ethyl and the like; acyloxy-lower alkyl groups such as acetoxymethyl, propionyloxymethyl, pivaloyloxymethyl and the like; nitrogen-containing heterocyclic lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl)ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting group for the hydroxyl group includes all conventional groups usable as hydroxyl-protecting groups, for example, alkoxy- and alkylthiocarbonyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio) ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, S-benzylthiocarbonyl and the like; acyl groups such as acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; lower alkynyl groups such as propargyl and the like; ar-lower alkyl groups such as benzyl, 4-methoxybenzyl, 3,4-dimethoxybenzyl, diphenylmethyl, trityl and the like; oxygen-containing or sulfur-containing heterocyclic groups such as tetrahydrofuryl, tetrahydropyranyl, tetrahydrothiopyranyl and the like; lower alkoxy- or lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl) ethoxymethyl, 1-ethoxyethyl, 1-methyl-1-methoxyethyl and the like; lower alkyl- or aryl-sulfonyl groups such as methanesulfonyl, p-toluenesulfonyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting group for the amino group includes all conventional groups usable as amino-protecting groups, for example, alkoxycarbonyl groups such as methoxycarbonyl, 2,2,2-trichloroethoxycarbonyl, 2,2,2-tribromoethoxycarbonyl, 2-trimethylsilylethoxy-carbonyl, 1,1-dimethylpropoxycarbonyl, tert-butoxycarbonyl, vinyloxycarbonyl, allyloxycarbonyl, 1-adamantyloxycarbonyl, benzyloxycarbonyl, 4-nitrobenzyloxycarbonyl, 2-bromobenzyloxycarbonyl, 4-methoxybenzyloxycarbonyl, 2,4-dichlorobenzyloxycarbonyl, diphenylmethoxycarbonyl, 4-(phenylazo)benzyloxycarbonyl, 2-furfuryloxycarbonyl, 8-quinolyloxycarbonyl and the like; acyl groups such as (mono-, di- or tri-)chloroacetyl, trifluoroacetyl, phenylacetyl, formyl, acetyl, benzoyl, phthaloyl, succinyl, alanyl, leucyl and the like; ar-lower alkyl groups such as benzyl, diphenylmethyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- or diar-lower alkylphosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; and substituted silyl groups such as trimethylsilyl and the like.

The salt of the compound of the general formula [1] includes usually known salts at basic groups such as amino group and the like and salts at acidic groups such as hydroxyl group, carboxyl group and the like.

The salts at the basic groups include, for example, salts with mineral acids such as hydrochloric acid, hydrobromic acid, nitric acid, sulfuric acid and the like; salts with organic carboxylic acids such as formic acid, acetic acid, citric acid, oxalic acid, fumaric acid, maleic acid, succinic acid, malic acid, tartaric acid, aspartic acid, trichloroacetic acid, trifluoroacetic acid and the like; and salts with sulfonic acids such as methanesulfonic acid, benzenesulfonic acid, p-toluenesulfonic acid, mesitylenesulfonic acid, naphthalenesulfonic acid and the like.

The salts at the acidic-groups include, for example, salts with alkali metals such as sodium, potassium and the like; salts with alkaline earth metals such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like.

Of the above-exemplified salts, preferable salts are pharmacologically acceptable salts.

When the alkyl ether derivative of the general formula [1] or its salt has isomers (for example, optical isomers, geometrical isomers and tautomers), the present invention includes all of these isomers, and the derivative or its salt may be in the form of a hydrate or solvate or in any crystal form.

Preferable examples of the alkyl ether derivative of the general formula [1] or salt thereof of the present invention are compounds of the general formula [1] in which the portion represented by

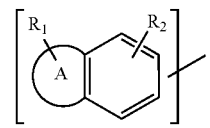

is any of the following:

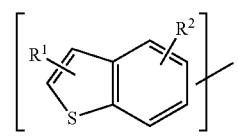

(A)

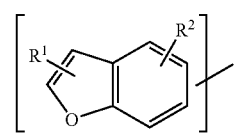

(B)

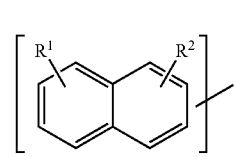

(C)

Of such compounds, preferable examples of the derivative or salt thereof of the present invention are compounds in which $R^1$ is a hydrogen atom; and $R^2$ is a hydrogen atom, a halogen atom or an alkoxy group.

In addition, compounds of the general formula [1] in which m=2 and n=2~3 are preferable. Of such compounds, compounds of the general formula [1] in which p=1~2 are more preferable.

The most preferable examples of the derivative or salt thereof of the present invention are compounds in which each of $R^1$ and $R^2$ in the above group (A) is a hydrogen atom; $R^3$ is a hydroxyl group; m=2; n=3; and p=1.

Processes for producing the alkyl ether derivative of the general formula [1] or its salt are explained below.

The alkyl ether derivative of the general formula [1] or its salt can be produced, for example, by any of the following production processes by adopting one or a proper combination of per se well-known methods.

Production process 1
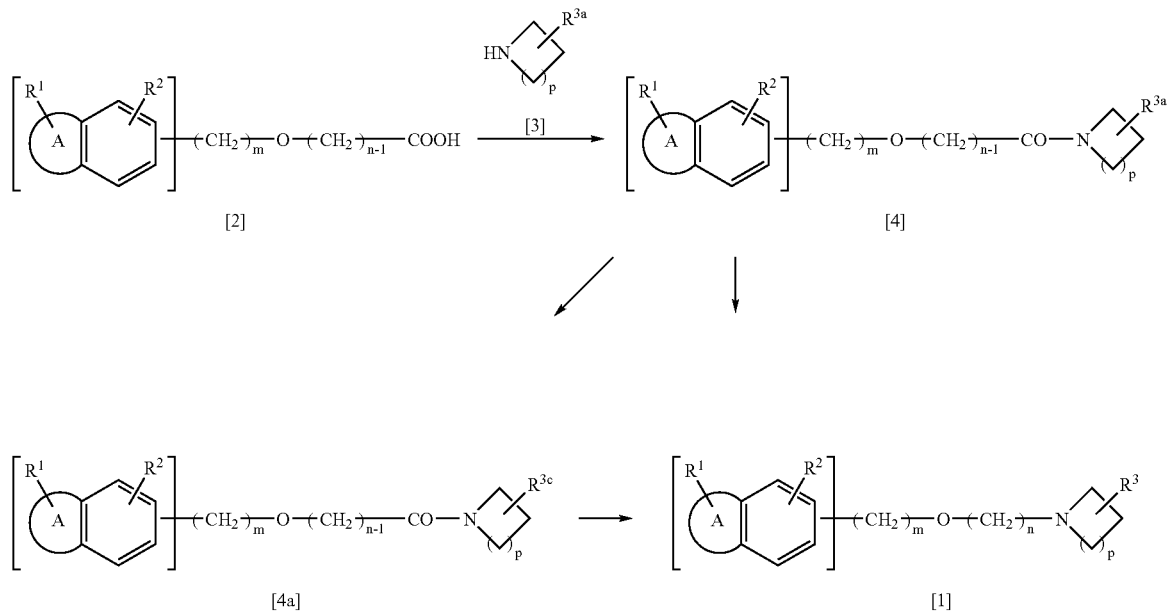
Production process 2
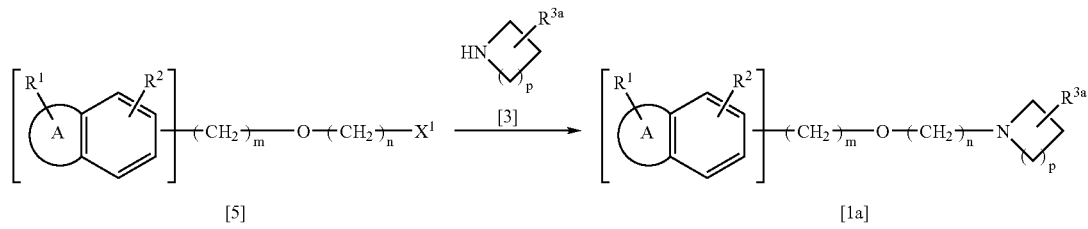
Production process 3
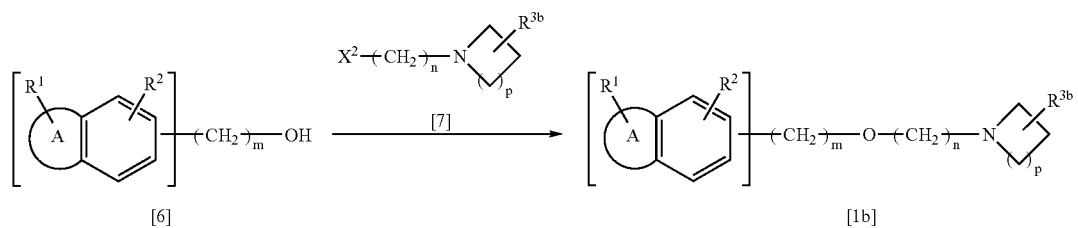
Production process 5
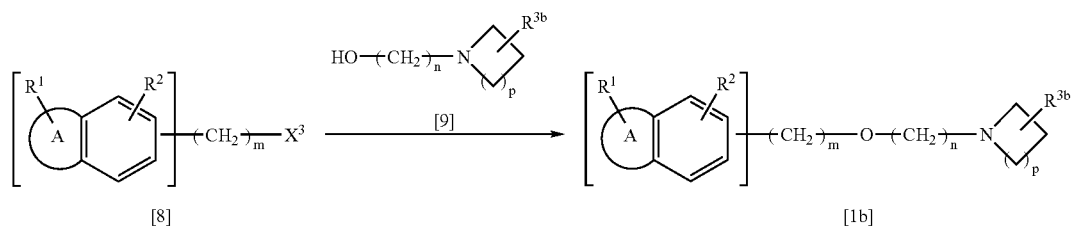

Production process 5

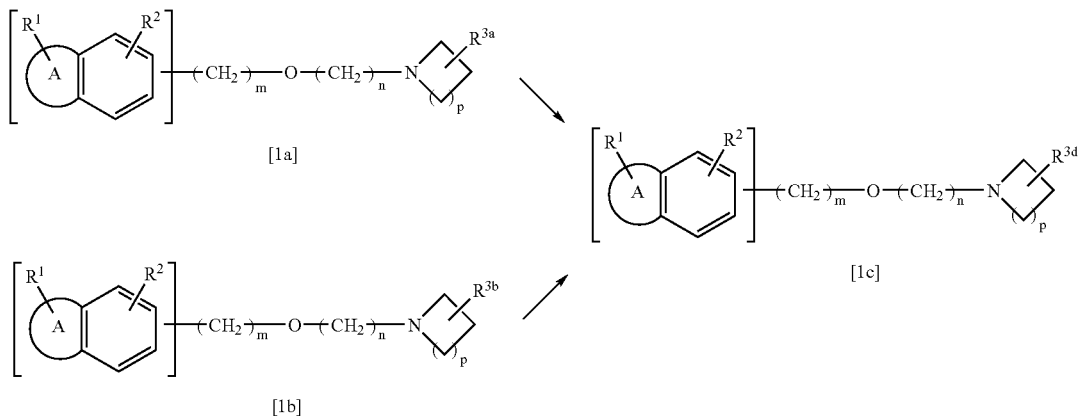

wherein $R^1$, $R^2$, $R^3$, A, m, n and p are as defined above; $R^{3a}$ is a dialkylamino group, a protected monoalkylamino group, a protected amino group or a protected or unprotected hydroxyl group; $R^{3b}$ is a dialkylamino group, a protected monoalkylamino group, a protected amino group or a protected hydroxyl group; $R^{3c}$ is a protected hydroxyl group; $R^{3d}$ is a monoalkylamino group, an amino group or a hydroxyl group; and each of $X^1$, $X^2$ and $X^3$ is a leaving group.

The leaving group includes, for example, halogen atoms, lower alkylsulfonyloxy groups and arylsulfonyloxy groups.

The individual production processes are explained below.

Production Process 1.

(1-1) A compound of the general formula [4] can be produced by reacting a compound of the general formula [2] or its reactive derivative with a compound of the general formula [3].

This reaction may be carried out by a per se well-known method, for example, the method described in Japanese Chemical Association, "Jikken Kagaku Koza" vol. 22, pages 137-173 (1992), Maruzen Co., Ltd. or a method based thereon.

The reactive derivative of the compound of the general formula [2] includes, for example, acid halides, acid anhydrides, activated amides and activated esters.

When the compound of the general formula [2] is used in the form of a free acid, the reaction is preferably carried out in the presence of a condensing agent.

The condensing agent includes, for example, N,N'-dialkylcarbodiimides such as N,N'-dicyclohexyl-carbodiimide and the like; halogenating agents such as thionyl chloride, oxalyl chloride and the like; acid halides such as ethoxycarbonyl chloride and the like; agents for conversion to an activated amide, such as carbonyldiimidazole and the like; and agent for conversion to an azide, such as diphenylphosphoryl azide and the like.

The amount of the condensing agent used is 1 mole or more, preferably 1 to 5 moles, per mole of the compound of the general formula [2].

In the reaction, any solvent may be used so long as it has no undesirable influence on the reaction. The solvent includes, for example, water; halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitriles such as acetonitrile and the like; and heteroaromatic compounds such as pyridine and the like. These solvents may be used singly or as a mixture thereof.

The reaction may be carried out in the presence of a base.

The base includes, for example, organic or inorganic bases such as triethylamine, diisopropylethylamine, 1,8-diazabicyclo[5,4,0]undec-7-ene (DBU), pyridine, potassium tert-butoxide, sodium carbonate, sodium hydrogencarbonate, potassium carbonate, sodium hydroxide and the like.

The amount of the base used is 0.5 mole or more, preferably 1 to 10 moles, per mole of the compound of the general formula [2].

The amount of the compound of the general formula [3] is 1 mole or more, preferably 1 to 20 moles, per mole of the compound of the general formula [2].

The reaction is carried out at usually −100° C. to 200° C., preferably −60° C. to 100° C., for 10 minutes to 20 hours.

The compound of the general formula [4] obtained may be used as it is in the subsequent reaction without isolation.

(1-2) When $R^{3a}$ is an unprotected hydroxyl group in the compound of the general formula [4], this compound can be converted to a compound of the general formula [4a] by subjecting it to a conventional reaction for protecting the hydroxyl group.

This reaction may be carried out by a per se well-known method, for example, the method described in Theodora W. Green, "Protective Groups in Organic Synthesis" pages 10-118 (1991), John Wiley & Sons. Inc., or a method based thereon.

A compound used in the reaction for protecting the hydroxyl group includes, for example, acid anhydrides such as acetic anhydride and the like; acid halides such as benzoyl chloride, pivaloyl chloride, methoxycarbonyl chloride, ethoxycarbonyl chloride and the like; halides such as methoxymethyl chloride, benzyloxymethyl chloride, benzyl chloride, benzyl bromide, trityl chloride, triethylsilyl chloride and the like; organic carboxylic acid compounds such as benzoic acid and the like; dialkoxyalkyl compounds such as dimethoxymethane and the like; and acyclic or cyclic alkoxyvinyl compounds such as 2-methoxypropene, 3,4-dihydro-2H-pyran and the like.

The amount of the compound used in the reaction for protecting the hydroxyl group is 1 mole or more, preferably 1 to 2 moles, per mole of the compound of the general formula [4a].

The reaction for protecting the hydroxyl group by the use of any of the acid anhydrides, the acid halides and the halides is usually carried out in the presence of a base or a dehalogenating agent. The base used includes, for example, organic or inorganic bases such as triethylamine, N,N-diisopropylethylamine, 1,8-diazabicyclo[5,4,0]undec-7-ene (DBU), pyridine, 4-dimethylaminopyridine, potassium tert-butoxide, sodium hydroxide, potassium hydroxide, sodium hydride and the like. The dehalogenating agent includes silver compounds such as silver oxide and the like.

The reaction for protecting the hydroxyl group by the use of the organic carboxylic acid compound is carried out in the presence of a dehydrating agent. The dehydrating agent used includes, for example triphenylphosphine-diisopropyl=azodicarboxylate.

The reaction for protecting the hydroxyl group by the use of any of the acid anhydrides, the dialkoxyalkyl compounds and the acyclic or cyclic alkoxyvinyl compounds is usually carried out in the presence of an acid catalyst. The acid used includes organic sulfonic acids such as p-toluenesulfonic acid and the like; inorganic acids such as hydrochloric acid, sulfuric acid and the like; and Lewis acids such as boron trifluoride, boron trifluoride diethyl ether complex, boron trifluoride tetrahydrofuran complex and the like.

The amount of the base, dehalogenating agent or dehydrating agent used in the reaction is 1 mole or more, preferably 1 to 2 moles, per mole of the compound used in the reaction for protecting the hydroxyl group. The amount of the acid used as catalyst is 0.001 to 10 moles, preferably 0.01 to 1 mole, per mole of the compound of the general formula [4a].

In the reaction, any solvent may be used so long as it has no undesirable influence on the reaction. The solvent includes, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitrites such as acetonitrile and the like; and heteroaromatic compounds such as pyridine and the like. These solvents may be used singly or as a mixture thereof.

The reaction is carried out at usually $-100°$ C. to $200°$ C., preferably $-60°$ C. to $100°$ C., for 10 minutes to 30 hours.

The reactants or base used in each of the above production methods may be used also as a solvent, depending on their properties.

The compound of the general formula [4a] obtained may be used as it is in the subsequent reaction without isolation.

(1-3) A compound of the general formula [1] can be produced by subjecting the compound of the general formula [4] or the general formula [4a] to a conventional reduction.

This reduction may be carried out by a per se well-known method, for example, the method described in Japanese Chemical Association, "Shin Jikken Kagaku Koza" vol. 15, [II], pages 29-244 (1977), Maruzen Co., Ltd. or a method based thereon.

In the reaction, any solvent may be used so long as it has no undesirable influence on the reaction. The solvent includes, for example, halogenated hydrocarbons such as methylene chloride, chloroform and the like; ethers such as tetrahydrofuran, dioxane and the like; aromatic hydrocarbons such as benzene, toluene, xylene and the like; and alcohols such as methanol, ethanol, isopropanol and the like. These solvents may be used singly or as a mixture thereof.

As a reducing agent, there are exemplified aluminum hydrides such as lithium aluminum hydride and the like; and boron hydrides such as diborane, boranetetrahydrofuran complexes, borane-dimethyl sulfide complexes, sodium borohydride and the like.

When sodium borohydride is used as the reducing agent, the reaction is preferably carried out in the presence of a Lewis acid such as boron trifluoride, boron trifluoride diethyl ether complex, boron trifluoride tetrahydrofuran complex or the like.

The amount of the reducing agent used is 0.2 mole or more, preferably 0.5 to 10 moles, per mole of the compound of the general formula [4] or the general formula [4a].

The amount of the Lewis acid used is 1 mole or more, preferably 4/3 to 2 moles, per mole of the reducing agent.

The reaction is carried out at usually $-50°$ C. to $200°$ C., preferably $0°$ C. to $110°$ C., for 10 minutes to 20 hours.

Production Process 2.

A compound of the general formula [1a] can be produced by reacting a compound of the general formula [5] with a compound of the general formula [3] in the presence or absence of a base.

In this reaction, any solvent may be used so long as it has no undesirable influence on the reaction. The solvent includes, for example, water; halogenated hydrocarbons such as methylene chloride, chloroform and the like; aromatic hydrocarbons such as benzene, toluene, xylene and the like; ethers such as tetrahydrofuran, dioxane and the like; alcohols such as methanol, ethanol and the like; nitrites such as acetonitrile and the like; amides such as N,N-dimethylformamide and the like; and sulfoxides such as dimethyl sulfoxide and the like. These solvents may be used singly or as a mixture thereof.

The base optionally used includes, for example, organic or inorganic bases such as triethylamine, diisopropylethylamine, 1,8-diazabicyclo[5,4,0]undec-7-ene (DBU), pyridine, potassium tert-butoxide, sodium carbonate, sodium hydrogencarbonate, potassium carbonate, sodium hydroxide and the like.

The amount of the base used is 0.5 mole or more, preferably 1 to 20 moles, per mole of the compound of the general formula [5].

In addition, the reaction may be carried out in the presence of a catalyst.

The catalyst includes, for example, potassium iodide and sodium iodide.

The amount of the catalyst used is 0.01 to 10 moles, preferably 0.1 to 1 mole, per mole of the compound of the general formula [5].

The amount of the compound of the general formula [3] used is 1 mole or more, preferably 1 to 20 moles, per mole of the compound of the general formula [5].

The reaction is carried out at usually $0°$ C. to $200°$ C., preferably $20°$ C. to $150°$ C., for 10 minutes to 20 hours.

The reactants or base used in the above production process may be used also as a solvent, depending on their properties.

Production Process 3.

A compound of the general formula [1b] can be produced by reacting a compound of the general formula [6] with a compound of the general formula [7] in the presence of a base.

This reaction may be carried out by a per se well-known method, for example, the method described in Tetrahedron Letters, vol. 38, pages 3251-3254 (1975) and Japanese Chemical Association, "Shin Jikken Kagaku Koza" vol. 14, [I], pages 567-611 (1977), Maruzen Co., Ltd. or a method based thereon.

The base includes, for example, sodium hydride, sodium hydroxide, potassium hydroxide and potassium tert-butoxide.

In the reaction, any solvent may be used so long as it has no undesirable influence on the reaction. The solvent includes, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; and water. These solvents may be used singly or as a mixture thereof.

The reaction may be carried out in the presence or absence of a catalyst.

The catalyst used includes usually known phase transfer catalysts composed of a quaternary ammonium salt, and preferable examples thereof are tetra-n-butylammonium hydrogensulfate and tetra-n-butylammonium bromide.

The amount of each of the compound of the general formula [7] and the base used in the reaction is 1 mole or more, preferably 1 to 20 moles, per mole of the compound of the general formula [6]. The amount of the catalyst is 0.001 to 1 mole per mole of the compound of the general formula [6].

The reaction is carried out at usually −50° C. to 200° C., preferably 0° C. to 150° C., for 10 minutes to 20 hours.

Production Process 4.

A compound of the general formula [1b] can be produced by reacting a compound of the general formula [8] with a compound of the general formula [9] in the presence or absence of a base.

This reaction may be carried out by a per se well-known method, for example, the same method as in production process 3.

Production Process 5.

(5-1) A compound of the general formula [1c] can be produced by subjecting a compound of the general formula [1a] and a compound of the general formula [1b] to a conventional deprotecting reaction.

This reaction may be carried out by a per se well-known method, for example, the method described in Theodora W. Green, "Protective Groups in Organic Synthesis" pages 10-118 and 309-405 (1991), John Wiley & Sons. Inc., or a method based thereon.

The deprotecting reaction is carried out under conditions for, for example, hydrolysis and transesterification reaction in the presence of an acid or a base, substitution and elimination reaction in the presence of an acid catalyst, or hydrogenolysis in the presence of a metal catalyst. The base used includes, for example, inorganic bases such as sodium hydroxide, potassium hydroxide, sodium hydride and the like. The acid includes organic sulfonic acids such as p-toluenesulfonic acid and the like; organic carboxylic acids such as formic acid, acetic acid, trifluoroacetic acid and the like; inorganic acids such as hydrochloric acid, sulfuric acid and the like; and Lewis acids such as boron trifluoride, boron trifluoride diethyl ether complex, boron trifluoride tetrahydrofuran complex and the like. The metal catalyst includes, for example, transition metals such as platinum, palladium, palladium-carbon, palladium hydroxide and the like.

The base used in the reaction may be used in an amount of 1 mole or more, preferably 1 to 5 moles, per mole of a combination of the compounds of the general formulas [1a] and [1b]. The amount of the acid used is 1 mole or more, preferably 1.1 to 100 moles, per mole of a combination of the compounds of the general formulas [1a] and [1b]. The amount of the metal catalyst used is a catalytic amount, preferably 0.01 to 30% by weight, relative to a combination of the compounds of the general formulas [1a] and [1b].

In the reaction, any solvent may be used so long as it has no undesirable influence on the reaction. The solvent includes, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitrites such as acetonitrile and the like; alcohols such as methanol, ethanol and the like; organic carboxylic acids such as formic acid, acetic acid and the like; and water. These solvents may be used singly or as a mixture thereof.

The reaction is carried out at usually −100° C. to 200° C., preferably −60° C. to 120° C., for 10 minutes to 20 hours.

The acid used in each of the above production methods may be used also as a solvent, depending on its properties.

(5-2) The compound of the general formula [1c] can be converted to the compound of the general formula [1b] by subjecting it to any of conventional reactions for protection of a hydroxyl group and an amino group and the alkylation of an amino group.

The reaction for protecting a hydroxyl group may be carried out by a per se well-known method, for example, the method described in Theodora W. Green, "Protective Groups in Organic Synthesis" pages 10-118 (1991), John Wiley & Sons. Inc., or a method based thereon, namely, the reaction may be carried out by the same method as in the above item (1-2).

The reaction for protecting an amino group may be carried out by a per se well-known method, for example, the method described in Theodora W. Green, "Protective Groups in Organic Synthesis" pages 309-405 (1991), John Wiley & Sons. Inc., or a method based thereon.

A compound used in the reaction for protecting an amino group includes, for example, acid anhydrides such as acetic anhydride and the like; and acid halides such as acetyl chloride, benzoyl chloride, mesyl chloride, tosyl chloride and the like. The amount of the compound used is 1 mole or more, preferably 1 to 2 moles, per mole of the compound of the general formula [1c].

This reaction is usually carried out in the presence of a base, and the base includes, for example, organic or inorganic bases such as triethylamine, diisopropylethylamine, 1,8-diazabicyclo[5,4,0]undec-7-ene (DBU), pyridine, potassium tert-butoxide, sodium carbonate, sodium hydrogencarbonate, potassium carbonate, sodium hydride and the like.

The amount of the base used is 0.5 mole or more, preferably 1 to 10 moles, per mole of the compound of the general formula [1c].

In the reaction, any solvent may be used so long as it has no undesirable influence on the reaction. The solvent includes, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitrites such as acetonitrile and the like; alcohols such as methanol, ethanol and the like; and water. These solvents may be used singly or as a mixture thereof.

The reaction is carried out at usually −100° C. to 200° C., preferably −60° C. to 100° C., for 10 minutes to 20 hours.

The alkylation of an amino group may be carried out by a per se well-known method, for example, the method described in Japanese Chemical Association, "Shin Jikken Kagaku Koza" vol. 14, [III], pages 1332-1399 (1977), Maruzen Co., Ltd. or a method based thereon.

A compound used in the alkylation of an amino group includes, for example, carbonyl compounds such as formaldehyde, paraformaldehyde, acetaldehyde, acetone and the like.

The amount of this compound used is 1 mole or more, preferably 1 to 5 moles, per mole of the compound of the general formula [1c].

This reaction is usually carried out in the presence of a reducing agent, and the reducing agent includes boron hydrides such as sodium borohydride and the like.

The amount of the reducing agent used is 0.5 mole or more, preferably 1 to 10 moles, per mole of the carbonyl compound.

In the reaction, any solvent may be used so long as it has no undesirable influence on the reaction. The solvent includes, for example, water; halogenated hydrocarbons such as methylene chloride, chloroform and the like; aromatic hydrocarbons such as benzene, toluene, xylene and the like; ethers such as tetrahydrofuran, dioxane and the like; and alcohols such as methanol, ethanol and the like. These solvents may be used singly or as a mixture thereof.

The reaction is carried out at usually −100° C. to 200° C., preferably 0° C. to 100° C., for 10 minutes to 30 hours.

The reactants used in each of the above production methods may be used also as a solvent, depending on their properties.

In the above production processes, each of the compounds of the general formulas [2] to [9] can be used in the form of a salt. As the salt, there are exemplified the same salts as in the case of the compound of the general formula [1]. As salts of the compounds of the general formulas [1a], [1b] and [1c], there are exemplified the same salts as in the case of the compound of the general formula [1].

When any of the compounds of the general formulas [1a], [1b], [1c] and [2] to [9] has isomers (for example, optical isomers, geometrical isomers and tautomers), each of these isomers can be used. In addition, any of the compounds may be used in the form of a hydrate or solvate or in any crystal form.

Each of the compounds of the general formulas [1a], [1b], [1c] and [2] to [9] may be used as it is in the subsequent reaction without isolation.

When any of the compounds of the general formulas [1], [1a], [1b], [1c] and [2] to [9] has a hydroxyl group, an amino group or a carboxyl group, it is possible to previously protect the hydroxyl group, the amino group or the carboxyl group with a conventional protecting group and, if necessary, remove the protecting group by a per se well-known method after completion of the reaction.

In addition, each of the alkyl ether derivatives of the general formulas [1], [1a], [1b] and [1c] or its salt can be converted to another alkyl ether derivative of the general formula [1] or its salt by a proper combination of per se well-known methods such as oxidation, reduction, alkylation, halogenation, sulfonylation, substitution, dehydration, hydrolysis and the like.

The alkyl ether derivatives of the general formulas [1], [1a], [1b] and [1c] or their salts can be isolated and separated according to one or more conventional operations which may be selected from extraction, crystallization, distillation, column chromatography and the like.

Processes for producing each of the compounds of the general formulas [2] and [5], which is a starting material for producing the compound of the present invention, are explained below.

The compound of the general formula [2] can be produced, for example, by the following production process A by adopting one or a proper combination of per se well-known methods.

Production process A.

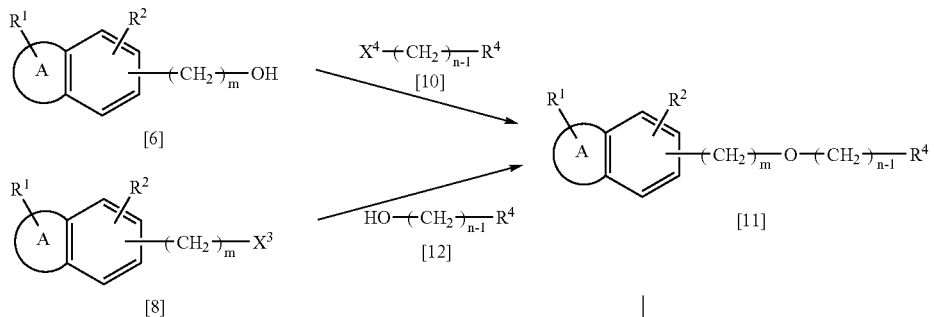

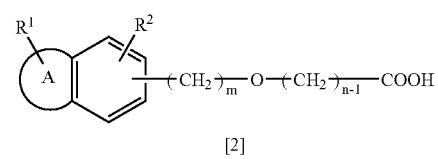

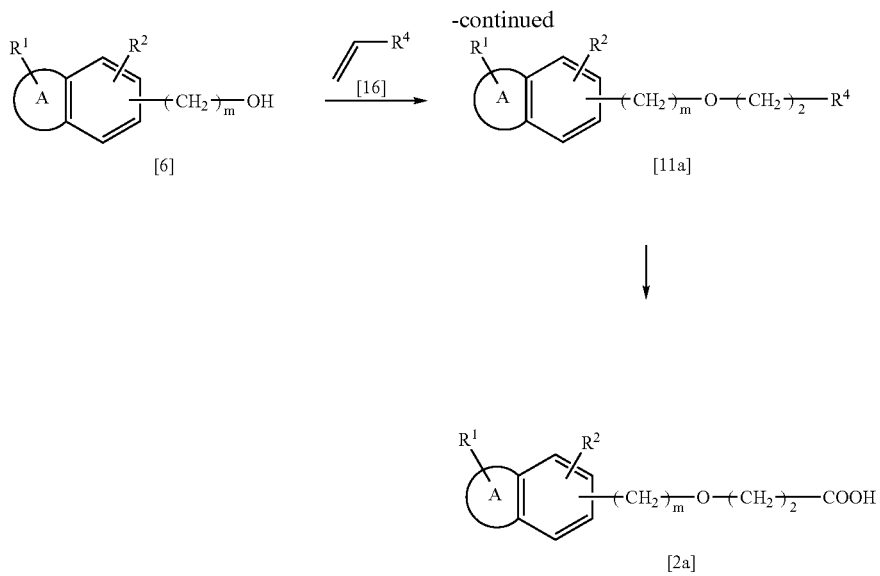

wherein $R^1$, $R^2$, A, $X^3$, m and n are as defined above; $R^4$ is a cyano group, a lower alkoxycarbonyl group, a dialkylaminocarbonyl group or a cyclic aminocarbonyl group; and $X^4$ is a leaving group.

(A-1) A compound of the general formula [11] can be produced by reacting a compound of the general formula [6] with a compound of the general formula [10] in the presence of a base.

This reaction may be carried out by a per se well-known method, for example, the method described in Japanese Chemical Association, "Shin Jikken Kagaku Koza" vol. 14, [I], pages 567-611 (1977), Maruzen Co., Ltd. or a method based thereon.

(A-2) A compound of the general formula [11] can be produced by reacting a compound of the general formula [8] with a compound of the general formula [12] in the presence of a base.

This reaction may be carried out by a per se well-known method, for example, the same method as in the production process (A-1).

(A-3) The compound of the general formula [2] can be produced by subjecting the compound of the general formula [11] to a conventional hydrolysis of nitrile, ester or amide.

This reaction may be carried out by a per se well-known method, for example, the method described in Japanese Chemical Association, "Shin Jikken Kagaku Koza" vol. 14, [II], pages 930-950 (1977), Maruzen Co., Ltd. and Theodora W. Green, "Protective Groups in Organic Synthesis" pages 152-192 (1981), John Wiley & Sons. Inc. or a method based thereon.

(A-4) A compound of the general formula [11a] can be produced by subjecting a compound of the general formula [6] to Michael addition with a compound of the general formula [16] in the presence of a base.

This reaction may be carried out by a per se well-known method, for example, the method described in any of "Chemical & Pharmaceutical Bulletin" vol. 41, pages 1659-1663 (1993), Japanese Chemical Association, "Shin Jikken Kagaku Koza" vol. 14, [I], pages 585-587 (1977), Maruzen Co., Ltd. and JP-A-3-99038, or a method based thereon.

(A-5) A compound of the general formula [2a] can be produced by subjecting the compound of the general formula [11a] to a conventional hydrolysis of nitrile, ester or amide.

This reaction may be carried out by a per se well-known method, for example, the same method as in (A-3).

The compound of the general formula [5] can be produced, for example, by the following production process B by adopting one or a proper combination of per se well-known methods.

Production process B.

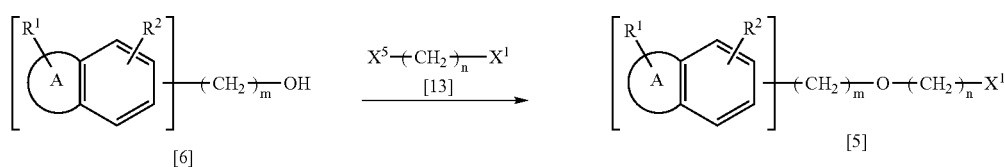

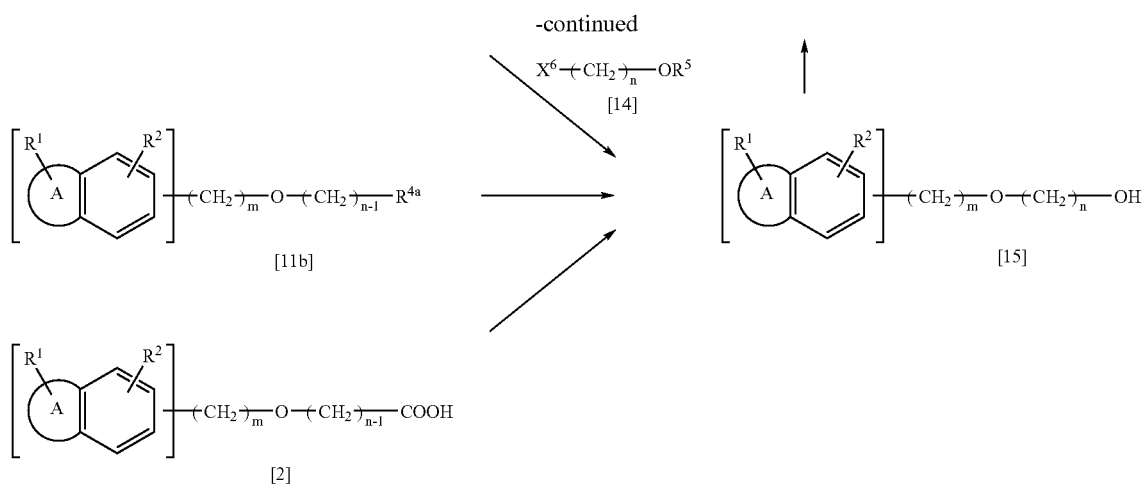

wherein $R^1$, $R^2$, $X^1$, A, m and n are as defined above; $R^{4a}$ is an alkoxycarbonyl group; $R^5$ is a hydroxyl-protecting group which is stable under basic conditions; and each of $X^5$ and $X^6$ is a leaving group.

The hydroxyl-protecting group stable under basic conditions includes, for example, lower alkyl groups such as tert-butyl and the like; lower alkenyl groups such as allyl and the like; ar-lower alkyl groups such as benzyl, 4-methoxybenzyl, 3,4-dimethoxybenzyl, diphenylmethyl, trityl and the like; oxygen-containing or sulfur-containing heterocyclic groups such as tetrahydrofuryl, tetrahydropyranyl, tetrahydrothiopyranyl and the like; lower alkoxy-lower alkyl groups such as methoxymethyl, 2-(trimethylsilyl)ethoxymethyl, 1-methyl-1-methoxyethyl and the like; and substituted silyl groups such as tert-butyldimethylsilyl, diphenylmethylsilyl and the like.

(B-1) The compound of the general formula [5] can be produced by reacting a compound of the general formula [6] with a compound of the general formula [13].

This reaction may be carried out by a per se well-known method, for example, the method described in Tetrahedron Letters, vol. 38, pages 3251-3254 (1975) and Japanese Chemical Association, "Shin Jikken Kagaku Koza" vol. 14, [I], pages 567-611 (1977), Maruzen Co., Ltd. or a method based thereon.

(B-2) A compound of the general formula [15] can be produced by reacting a compound of the general formula [6] with a compound of the general formula [14], and then removing the protecting group.

This reaction may be carried out by a per se well-known method, for example, the same method as in production process 3, and then the protecting group may be removed.

(B-3) A compound of the general formula [15] can be produced by subjecting a compound of the general formula [2] or a compound of the general formula [11b] to a conventional reduction.

This reduction may be carried out by a per se well-known method, for example, the method described in "Shin Jikken Kagaku Koza" vol. 15, pages 26-244 (1977), Maruzen Co., Ltd. or a method based thereon.

(B-4) The compound of the general formula [5] can be produced by reacting the compound of the general formula [15] with a halogenating agent or a sulfonylating agent in the presence or absence of a base.

A solvent used in this reaction includes, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; and nitriles such as acetonitrile and the like. These solvents may be used singly or as a mixture thereof.

The base optionally used includes, for example, organic or inorganic bases such as triethylamine, diisopropylethylamine, 1,8-diazabicyclo[5,4,0]undec-7-ene, pyridine, potassium tert-butoxide, sodium carbonate, potassium carbonate, sodium hydride and the like.

The halogenating agent includes, for example, phosphorus oxychloride, phosphorus oxybromide, phosphorus trichloride, phosphorus pentachloride, carbon tetrabromide-triphenylphosphine, and thionyl chloride.

The sulfonylating agent includes, for example, methanesulfonyl chloride and p-toluenesulfonyl chloride.

The amount of each of the halogenating agent or sulfonylating agent and the base used is 1 mole or more, preferably 1 to 2 moles, per mole of the compound of the general formula [15].

The reaction is carried out at usually −50° C. to 200° C., preferably 0° C. to 50° C., for 10 minutes to 30 hours.

When any of the compounds of the general formulas [2], [2a], [6], [8], [10] to [16], [11a] and [11b] in production processes A and B has a hydroxyl group, an amino group or a carboxyl group, it is possible to previously protect the hydroxyl group, the amino group or the carboxyl group with a conventional protecting group and, if necessary, remove the protecting group by a per se well-known method after completion of the reaction.

When any of the compounds of the general formulas [2], [2a], [6], [8], [10] to [16], [11a] and [11b] has isomers (for example, optical isomers, geometrical isomers and tautomers), each of these isomers can be used. In addition, any of the compounds may be used in the form of a hydrate or solvate or in any crystal form.

Each of the compounds of the general formulas [2], [2a], [6], [8], [10] to [16], [11a] and [11b] may be used as it is in the subsequent reaction without isolation.

The compound of the present invention can be formulated into pharmaceutical preparations such as oral preparations (e.g. tablets, capsules, powders, granules, fine granules, pills, suspensions, emulsions, solutions and syrups), injections, suppositories, external preparations (e.g. ointments and patches), aerosols and the like by blending therewith various pharmaceutical additives such as excipients, binders, disintegrators, disintegration inhibitors, consolidation.adhesion inhibitors, lubricants, absorption.adsorption carriers, solvents, fillers, isotonicity agents, solubilizers, emulsifying agents, suspending agents, thickening agents, coating agents, absorption accelerators, gelation.coagulation accelerators, light stabilizers, preservatives, dehumidifiers, emulsion.suspension.dispersion stabilizers, color protectors, deoxygenation.oxidation inhibitors, sweetening.flavoring agents, coloring agents, foaming agents, defoaming agents, soothing agents, antistatic agents, buffering and pH-adjusting agents, etc.

The above various pharmaceuticals are prepared by conventional methods.

The oral solid pharmaceuticals such as tablets, powders and granules are prepared by a conventional method by using pharmaceutical additives for solid preparation, for example, excipients such as lactose, sucrose, sodium chloride, glucose, starch, calcium carbonate, kaolin, crystalline cellulose, anhydrous calcium secondary phosphate, partly pregelatinized starch, corn starch, alginic acid and the like; binders such as simple syrup, a glucose solution, a starch solution, a gelatin solution, polyvinyl alcohols, polyvinyl ethers, polyvinylpyrrolidones, carboxymethyl cellulose, shellac, methyl cellulose, ethyl cellulose, sodium alginate, gum arabic, hydroxypropylmethyl cellulose, hydroxypropyl cellulose, water, ethanol and the like; disintegrators such as dried starch, alginic acid, agar powder, starch, crosslinked polyvinylpyrrolidones, crosslinked carboxymethyl cellulose sodium salt, carboxymethyl cellulose calcium salt, starch sodium glycolate and the like; disintegration inhibitors such as stearyl alcohol, stearic acid, cacao butter, hydrogenated oil and the like; consolidation.adhesion inhibitors such as aluminum silicate, calcium hydrogenphosphate, magnesium oxide, talc, silicic acid anhydride and the like; lubricants such as carnauba wax, light silicic acid anhydride, aluminum silicate, magnesium silicate, hydrogenated oil, hydrogenated vegetable oil derivatives, sesame oil, white beeswax, titanium oxide, dried aluminum hydroxide gel, stearic acid, calcium stearate, magnesium stearate, talc, calcium hydrogenphosphate, sodium lauryl sulfate, polyethylene glycols and the like; absorption accelerators such as quaternary ammonium salts, sodium lauryl sulfate, urea, enzymes and the like; and absorption•adsorption carriers such as starch, lactose, kaolin, bentonite, silicic acid anhydride, hydrated silicon dioxide, magnesium aluminate metasilicate, colloidal silica and the like.

If necessary, tablets can be made into tablets having a conventional coating, such as sugar coated tablets, gelatin coated tablets, gastric coated tablets, enteric coated tablets and water-soluble-film coated tablets.

The capsules are prepared by mixing the compound of the present invention with the above-exemplified various pharmaceutical additives and packing the resulting mixture into hard gelatin capsules, soft capsules or the like.

The compound of the present invention can be formulated into an aqueous or oily suspension, solution, syrup or elixir by a conventional method by using the above-exemplified various additives for liquid preparation, such as solvents, fillers, isotonicity agents, solubilizers, emulsifying agents, suspending agents, thickening agents and the like.

The suppositories are prepared by adding a suitable absorption accelerator to, for example, a polyethylene glycol, cacao butter, lanolin, a higher alcohol, a higher alcohol ester, gelatin, a semi-synthesized glyceride or Witepsol.

The injections are prepared by a conventional method by using pharmaceutical additives for liquid preparation, for example, diluents such as water, ethanol, Macrogol, propylene glycol, citric acid, acetic acid, phosphoric acid, lactic acid, sodium lactate, sulfuric acid, sodium hydroxide and the like; pH adjustors and buffers, such as sodium citrate, sodium acetate, sodium phosphate and the like; stabilizers such as sodium pyrosulfite, ethylenediaminetetraacetic acid, thioglycolic acid, thiolactic acid and the like; isotonicity agents such as sodium chloride, glucose, mannitol, glycerol and the like; solubilizers such as carboxymethyl cellulose sodium salt, propylene glycol, sodium benzoate, benzyl benzoate, urethane, ethanolamine, glycerol and the like; soothing agents such as calcium gluconate, chlorobutanol, glucose, benzyl alcohol and the like; and local anesthetics.

The ointments in the form of paste, cream or gel are prepared by mixing and formulation according to a conventional method by using pharmaceutical additives, for example, base ingredients such as white soft paraffin, polyethylenes, paraffin, glycerol, cellulose derivatives, polyethylene glycols, silicone, bentonite and the like; preservatives such as methyl p-oxybenzoate, ethyl p-oxybenzoate, propyl p-oxybenzoate and the like; stabilizers; and wetting agents.

When the patch is prepared, the above-mentioned ointment, cream, gel or paste is applied on a conventional support by a conventional method. As the support, there can be used woven or nonwoven fabrics made of cotton, staple fiber or chemical fiber; and films or foamed sheets of soft vinyl chloride, a polyethylene, a polyurethane or the like.

A method for administering the above-mentioned pharmaceutical preparation is not particularly limited and is properly determined depending on the pharmaceutical form, the age, sex and other conditions of a patient, and the symptom of the patient.

The dose of active ingredient of the pharmaceutical preparation of the present invention is properly chosen depending on administration route, the age, sex and pathosis of a patient, and other conditions. Usually, the active ingredient may be administered to an adult in a dose of 0.1 to 500 mg per day in one portion or several portions.

BEST MODE FOR CARRYING OUT THE INVENTION

The present invention is illustrated with reference to the following examples, reference examples and test examples, which should not be construed as limiting the scope of the invention.

In the examples and reference examples, the mixing ratios in the eluents are all by volume, and B.W. Silica gel, BW-127ZH or FL-100DX (mfd. by FUJI SILYSIA CHEMICAL LTD.) was used as a carrier in the column chromatography.

The symbols used in the reaction schemes have the following meanings:

Ac: acetyl, Boc: tert-butoxycarbonyl,

Bz: benzoyl,

Piv: pivaloyl, Bn: benzyl, Tr: trityl,

MOM: methoxymethyl, BOM: benzyloxymethyl,

TES: triethylsilyl, THP: tetrahydropyranyl,

Ms: mesyl, Me: methyl, Et: ethyl, Ph: phenyl, t-Bu: tert-butyl.

EXAMPLE 1

Production of 1-{2-[2-(1-benzothiophen-5-yl)ethoxy]ethyl}-3-azetidinol

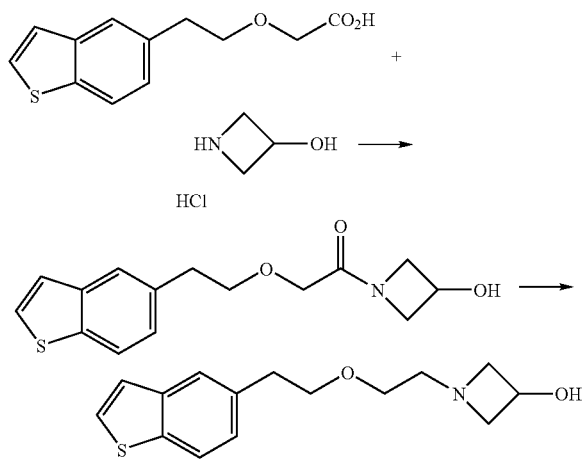

(1) In 12 mL of methylene chloride was dissolved 1.20 g of 2-[2-(1-benzothiophen-5-yl)ethoxy]acetic acid, and 2.3 mL of triethylamine and 0.38 g of imidazole were added to the solution. The resulting mixture was cooled to 5° C. and 0.41 mL of thionyl chloride was added dropwise thereto, followed by stirring at the same temperature for 1 hour. After the reaction mixture was cooled to −60° C., 0.82 mL of triethylamine and 0.72 g of 3-azetidinol hydrochloride were added thereto, and the resulting mixture was stirred at the same temperature for 1 hour and then at room temperature for 1.5 hours. Water was added to the reaction mixture and the pH was adjusted to 1.0 with 6 mol/L hydrochloric acid, after which the organic layer was separated. The organic layer was washed with a saturated aqueous sodium chloride solution and then dried over anhydrous magnesium sulfate. The solvent was distilled off under reduced pressure to obtain 2-[2-(1-benzothiophen-5-yl)ethoxy]-1-(3-hydroxy-1-azetidinyl)-1-ethanone as a yellow oil.

(2) The aforesaid 2-[2-(1-benzothiophen-5-yl)ethoxy]-1-(3-hydroxy-1-azetidinyl)-1-ethanone was dissolved in 12 mL of tetrahydrofuran and the resulting solution was cooled to 5° C., after which 12.7 mL of a 1 mol/L solution of a borane-tetrahydrofuran complex in tetrahydrofuran was added dropwise thereto and the resulting mixture was stirred at room temperature for 17 hours. To the reaction mixture was added 10 mL of acetone, and stirred for 30 minutes, followed by adding thereto 6.0 mL of 6 mol/L hydrochloric acid, and the resulting mixture was heated under reflux for 2 hours. After the reaction mixture was cooled, water and ethyl acetate were added thereto and the pH was adjusted to 13 with a 2 mol/L aqueous sodium hydroxide solution, and the organic layer was separated. The organic layer was washed with a saturated aqueous sodium chloride solution and then dried over anhydrous magnesium sulfate. The solvent was distilled off under reduced pressure to obtain 1.13 g of 1-{2-[2-(1-benzothiophen-5-yl)ethoxy]ethyl}-3-azetidinol as a yellow oil.

IR (neat) cm$^{-1}$: 3378, 2943, 1438, 1198, 1119, 703 NMR (CDCl$_3$) δ values: 2.66 (2H, t, J=6 Hz), 2.9-3.1 (2H, m), 2.99 (2H, t, J=7 Hz), 3.46 (2H, t, J=6 Hz), 3.6-3.7 (2H, m), 3.67 (2H, t, J=7 Hz), 4.41 (1H, qn, J=6 Hz), 7.20 (1H, dd, J=2, 8 Hz), 7.27 (1H, d, J=5 Hz), 7.41 (1H, d, J=5 Hz), 7.66 (1H, d, J=2 Hz), 7.78 (1H, d, J=8 Hz)

EXAMPLE 2

Production of 1-{2-[2-(1-benzothiophen-5-yl)ethoxy]ethyl}-3-azetidinol hydrochloride

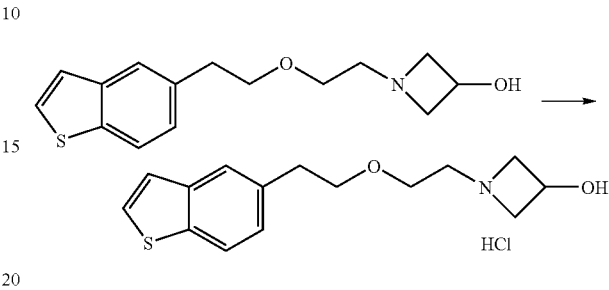

In 4.2 mL of ethyl acetate was dissolved 1.03 g of 1-{2-[2-(1-benzothiophen-5-yl)ethoxy]ethyl}-3-azetidinol, and to the solution was added 0.86 mL of a 4.76 mol/L dried hydrogen chloride-ethyl acetate solution. The resulting mixture was stirred at room temperature for 1 hour and then at 5° C. for 1 hour. The crystals precipitated were collected by filtration, washed with ethyl acetate and then dried to obtain 0.98 g of 1-{2-[2-(1-benzothiophen-5-yl)ethoxy]ethyl}-3-azetidinol hydrochloride.

Melting point: 101-102° C. IR (KBr) cm$^{-1}$: 3132, 2952, 1423, 1340, 1158, 814, 701 NMR (CDCl$_3$) δ values: 2.97 (2H, t, J=7 Hz), 3.2-3.3 (2H, m), 3.69 (2H, t, J=7 Hz), 3.6-3.8 (2H, m), 3.9-4.1 (2H, m), 4.2-4.4 (2H, m), 4.6-4.8 (1H, m), 7.18 (1H, dd, J=1, 8 Hz), 7.29 (1H, d, J=5 Hz), 7.41 (1H, d, J=5 Hz), 7.65 (1H, d, J=1 Hz), 7.78 (1H, d, J=8 Hz)

EXAMPLE 3

Production of 1-{3-[2-(1-benzothiophen-6-yl)ethoxy]propyl}-3-azetidinol

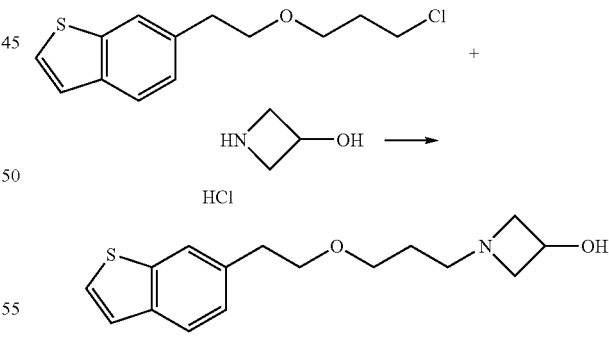

In 5 mL of dimethyl sulfoxide was dissolved 1.00 g of 6-[2-(3-chloropropoxy)ethyl]-1-benzothiophene, and 0.86 g of 3-azetidinol hydrochloride and 1.63 g of potassium carbonate were added to the solution. The resulting mixture was stirred at 75° C. for 2.5 hours and then at 95° C. for 1.5 hours. After the reaction mixture was cooled, water and ethyl acetate were added thereto and the pH was adjusted to 1 with 6 mol/L hydrochloric acid, and the aqueous layer was separated. Ethyl acetate was added to the aqueous layer and the pH was adjusted to 10 with a 2 mol/L aqueous sodium hydroxide solution, after which the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=30:1 to 5:1) to obtain 0.28 g of 1-{3-[2-(1-benzothiophen-6-yl)ethoxy]propyl}-3-azetidinol as a colorless oil.

IR (neat) cm$^{-1}$: 3398, 2940, 2867, 1197, 1107, 820, 757 NMR (CDCl$_3$) δ values: 1.60 (2H, qn, J=7 Hz), 2.45 (2H, t, J=7 Hz), 2.7-2.8 (2H, m), 2.99 (2H, t, J=7 Hz), 3.45 (2H, t, J=7 Hz), 3.5-3.6 (2H, m), 3.66 (2H, t, J=7 Hz), 4.37 (1H, qn, J=6 Hz), 7.23 (1H, dd, J=1, 8 Hz), 7.29 (1H, d, J=5 Hz), 7.37 (1H, d, J=5 Hz), 7.73 (1H, d, J=1 Hz), 7.74 (1H, d, J=8 Hz)

EXAMPLE 4

Production of 1-{3-[2-(1-benzothiophen-6-yl)ethoxy]propyl}-3-azetidinol hydrochloride

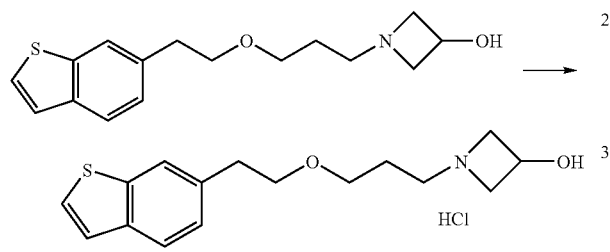

In 3.0 mL of ethyl acetate was dissolved 0.28 g of 1-{3-[2-(1-benzothiophen-6-yl)ethoxy]propyl}-3-azetidinol, and to the solution was added 0.35 mL of a 3.25 mol/L dried hydrogen chloride-ethyl acetate solution, after which the resulting mixture was stirred at room temperature for 1 hour. Then, the solvent was distilled off under reduced pressure to obtain 0.30 g of 1-{3-[2-(1-benzothiophen-6-yl)ethoxy]propyl}-3-azetidinol hydrochloride as a light-yellow oil.

IR (neat) cm$^{-1}$: 3264, 2866, 2596, 1398, 1109, 1048, 821 NMR (CDCl$_3$) δ values: 1.81 (2H, qn, J=6 Hz), 2.92 (2H, t, J=6 Hz), 2.98 (2H, t, J=6 Hz), 3.46 (2H, t, J=6 Hz), 3.68 (2H, t, J=6 Hz), 3.8-3.9 (2H, m), 3.8-4.0 (2H, m), 4.4-4.6 (1H, m), 7.23 (1H, dd, J=1, 8 Hz), 7.31 (1H, d, J=5 Hz), 7.39 (1H, d, J=5 Hz), 7.74 (1H, d, J=1 Hz), 7.76 (1H, d, J=8 Hz)

EXAMPLE 5

Production of 1-{3-[2-(1-benzothiophen-2-yl)ethoxy]propyl}-3-azetidinol

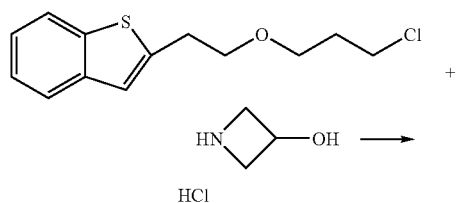

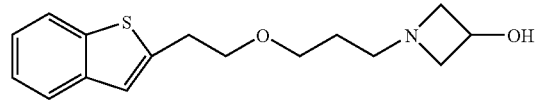

In the same manner as in Example 3, 1-{3-[2-(1-benzothiophen-2-yl)ethoxy]propyl}-3-azetidinol was obtained as a colorless oil.

IR (neat) cm$^{-1}$: 3366, 2942, 2856, 1458, 1436, 1113, 750 NMR (CDCl$_3$) δ values: 1.64 (2H, qn=7 Hz), 2.49 (2H, t, J=7 Hz), 2.7-2.8 (2H, m), 3.15 (2H, t, J=7 Hz), 3.50 (2H, t, J=7 Hz), 3.5-3.7 (2H, m), 3.71 (2H, t, J=7 Hz), 4.3-4.4 (1H, m), 7.06 (1H, s), 7.2-7.4 (2H, m), 7.67 (1H, dd, J=1, 7 Hz), 7.77 (1H, dd, J=1, 7 Hz)

EXAMPLE 6

Production of 1-{3-[2-(1-benzothiophen-2-yl)ethoxy]propyl}-3-azetidinol hydrochloride

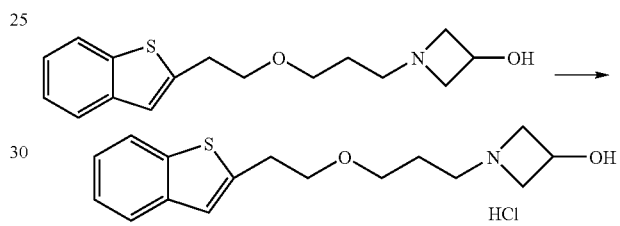

In the same manner as in Example 4, 1-{3-[2-(1-benzothiophen-2-yl)ethoxy]propyl}-3-azetidinol hydrochloride was obtained as a light-yellow oil.

IR (neat) cm$^{-1}$: 3290, 2868, 1457, 1436, 1113, 751 NMR (CDCl$_3$) δ values: 1.83 (2H, qn, J=6 Hz), 2.91 (2H, t, J=6 Hz), 3.16 (2H, t, J=6 Hz), 3.52 (2H, t, J=6 Hz), 3.74 (2H, t, J=6 Hz), 3.7-3.8 (2H, m), 3.7-3.9 (2H, m), 4.3-4.5 (1H, m), 7.09 (1H, s), 7.27 (1H, dt, J=1, 8 Hz), 7.33 (1H, dt, J=1, 8 Hz), 7.69 (1H, dd, J=1, 8 Hz), 7.78 (1H, dd, J=1, 8 Hz)

EXAMPLE 7

Production of 1-{3-[2-(1-benzothiophen-7-yl)ethoxy]propyl}-3-azetidinol

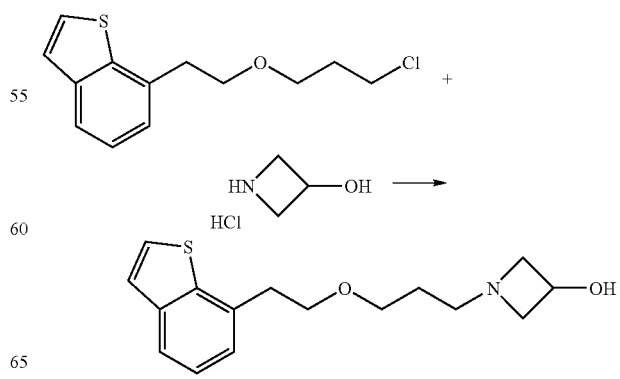

In the same manner as in Example 3, 1-{3-[2-(1-benzothiophen-7-yl)ethoxy]propyl}-3-azetidinol was obtained as a colorless oil.

IR (neat) cm$^{-1}$: 3386, 2942, 2856, 1458, 1105, 796, 755, 700 NMR (CDCl$_3$) δ values: 1.61 (2H, qn, J=7 Hz), 2.45 (2H, t, J=7 Hz), 2.7-2.8 (2H, m), 3.17 (2H, t, J=7 Hz), 3.48 (2H, t, J=7 Hz), 3.5-3.7 (2H, m), 3.79 (2H, t, J=7 Hz), 4.3-4.5 (1H, m), 7.20 (1H, dd, J=1, 8 Hz), 7.32 (1H, t, J=8 Hz), 7.36 (1H, d, J=5 Hz), 7.43 (1H, d, J=5 Hz), 7.70 (1H, dd, J=1, 8 Hz)

EXAMPLE 8

Production of 1-{3-[2-(1-benzothiophen-7-yl)ethoxy]propyl}-3-azetidinol hydrochloride

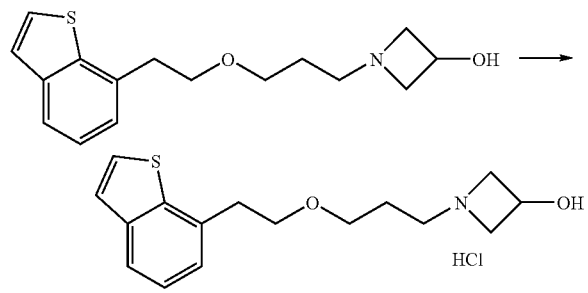

In the same manner as in Example 2, 1-{3-[2-(1-benzothiophen-7-yl)ethoxy]propyl}-3-azetidinol hydrochloride was obtained as colorless crystals.

Melting point: 105-106° C. IR (KBr) cm$^{-1}$: 3252, 2806, 2620, 1398, 1130, 1106, 811, 708 NMR (CDCl$_3$) δ values: 1.82 (2H, qn, J=6 Hz), 2.8-3.0 (2H, m), 3.16 (2H, t, J=6 Hz), 3.47 (2H, t, J=6 Hz), 3.83 (2H, t, J=6 Hz), 3.7-4.1 (4H, m), 4.5-4.7 (1H, m), 7.21 (1H, d, J=8 Hz), 7.36 (1H, t, J=8 Hz), 7.38 (1H, d, J=5 Hz), 7.46 (1H, d, J=5 Hz), 7.73 (1H, d, J=8 Hz)

EXAMPLE 9

(a) Production of 1-{3-[2-(1-benzothiophen-5-yl)ethoxy]propyl}-3-azetidinol 1

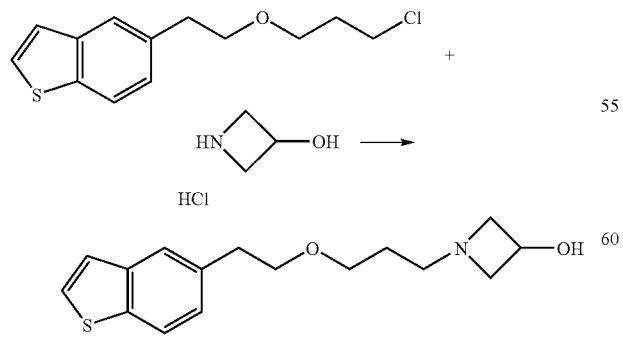

In 30 mL of dimethyl sulfoxide was dissolved 6.50 g of 5-[2-(3-chloropropoxy)ethyl]-1-benzothiophene, and to the solution were added 5.60 g of 3-azetidinol hydrochloride and 15.3 mL of a 5 mol/L aqueous sodium hydroxide solution, after which the resulting mixture was stirred at 65° C. for 3.5 hours. After the reaction mixture was cooled, water and ethyl acetate were added thereto and the pH was adjusted to 1 with 6 mol/L hydrochloric acid, and the aqueous layer was separated. Ethyl acetate was added to the aqueous layer and the pH was adjusted to 10 with a 5 mol/L aqueous sodium hydroxide solution, after which the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=30:1 to 10:1) to obtain 4.77 g of 1-{3-[2-(1-benzothiophen-5-yl)ethoxy]propyl}-3-azetidinol.

(b) Production of 1-{3-[2-(1-benzothiophen-5-yl)ethoxy]propyl}-3-azetidinol 2

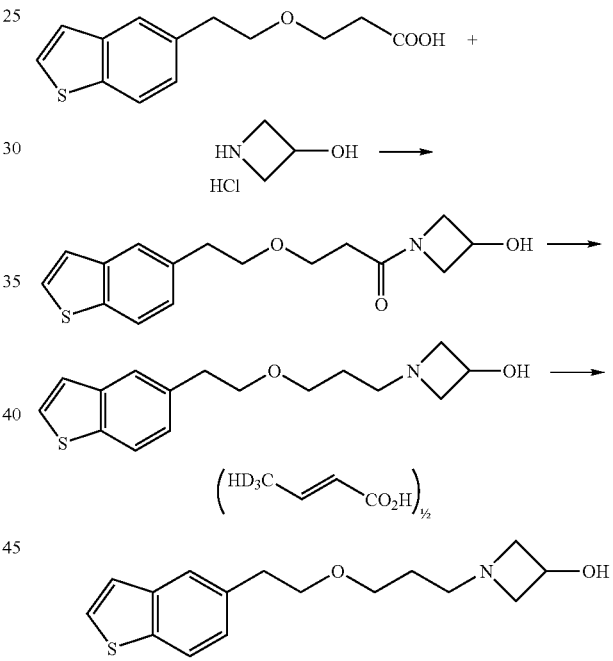

(1) In 300 mL of tetrahydrofuran was dissolved 100 g of 3-[2-(1-benzothiophen-5-yl)ethoxy]propionic acid, and 0.1 mL of N,N-dimethylformamide was added thereto, after which 41.8 mL of oxalyl chloride was added thereto over a period of 10 minutes and the resulting mixture was stirred at room temperature for 1.5 hours. The resulting solution was added dropwise to a solution of 65.7 g of 3-hydroxyazetidine hydrochloride and 59.5 g of sodium hydroxide in 600 mL of water at 10° C., followed by stirring at room temperature for 1 hour. To the reaction solution were added 600 mL of water, 500 mL of ethyl acetate and sodium chloride, and the organic layer was separated. To the aqueous layer was added 100 mL of ethyl acetate and the organic layer was separated. The organic layers thus obtained were combined. To the combined organic layer was added 100 mL of water and the pH was adjusted to 3.5 with 6 mol/L hydrochloric acid, after which the organic layer was separated. The organic layer was concentrated to a volume of about 200 mL, washed with a saturated aqueous sodium hydrogen-carbonate solution and then a saturated aqueous sodium chloride solution, dried over anhydrous magnesium sulfate, and then distilled under reduced pressure to remove the solvent. To the residue was added 300 mL of toluene, and the resulting mixture was heated at 50° C. to effect dissolution, after which seed crystals were added at 40° C. and the resulting mixture was slowly cooled and then stirred under ice-cooling for 30 minutes. The crystals precipitated were collected by filtration to obtain 96.6 g of 3-[2-(1-benzothiophen-5-yl) ethoxy]-1-(3-hydroxy-1-azetidinyl)-1-propanone as light-brown crystals.

(2) In 60 mL of tetrahydrofuran was dissolved 30.0 g of 3-[2-(1-benzothiophen-5-yl)ethoxy]-1-(3-hydroxy-1-azetidinyl)-1-propanone, followed by adding dropwise thereto 275 mL of a 1 mol/L solution of a borane-tetrahydrofuran complex in tetrahydrofuran, and the resulting mixture was stirred at room temperature for 5 hours. To the reaction solution was added dropwise 81.9 mL of 6 mol/L hydrochloric acid, and the resulting mixture was refluxed for 1.5 hours. After cooling, the solvent was concentrated to be reduced by about 290 mL, and the insoluble materials were filtered off. To the filtrate were added 120 mL of water and 60 mL of toluene, and the aqueous layer was separated and then washed with 60 mL of toluene. To the aqueous layer was added 90 mL of ethyl acetate, and the pH was adjusted to 9.5 with a 5 mol/L aqueous sodium hydroxide solution, after which the organic layer was separated. The organic layer was washed with a saturated aqueous sodium chloride solution and dried over anhydrous magnesium sulfate. The solvent was distilled off under reduced pressure and 5.35 g of fumaric acid and 54 mL of ethanol were added to the resulting residue. The resulting mixture was heated at 74° C. to effect dissolution, and then 161 mL of ethyl acetate was added dropwise thereto. The mixture thus obtained was slowly cooled and then stirred at 5 to 10° C. for 30 minutes, and the crystals precipitated were collected by filtration to obtain 22.7 g of 1-{3-[2-(1-benzothiophen-5-yl)ethoxy]propyl}-3-azetidinol ½ fumarate as light-brown crystals.

(3) In 45 mL of water was suspended 22.7 g of 1-{3-[2-(1-benzothiophen-5-yl)ethoxy]propyl}-3-azetidinol ½ fumarate, and 68 mL of ethyl acetate was added thereto, after which the pH was adjusted to 9.5 with a 1 mol/L aqueous sodium hydroxide solution and then the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; chloroform:methanol=20:1 to 10:1) and crystallized from 40 mL of diisopropyl ether to obtain 16.0 g of 1-{3-[2-(1-benzothiophen-5-yl)ethoxy]propyl}-3-azetidinol as a solid.

Melting point: 60-62° C. IR (KBr) cm$^{-1}$: 3095, 2944, 2769, 1361, 1191, 1098, 810, 709 NMR (CDCl$_3$) δ values: 1.61 (2H, qn, J=7 Hz), 2.45 (2H, t, J=7 Hz), 2.7-2.9 (2H, m), 2.99 (2H, t, J=7 Hz), 3.45 (2H, t, J=7 Hz), 3.5-3.6 (2H, m), 3.66 (2H, t, J=7 Hz), 4.3-4.4 (1H, m), 7.22 (1H, dd, J=1, 8 Hz), 7.28 (1H, d, J=5 Hz), 7.41 (1H, d, J=5 Hz), 7.67 (1H, d, J=1 Hz), 7.79 (1H, d, J=8 Hz)

EXAMPLE 10

Production of 1-{3-[2-(1-benzothiophen-5-yl) ethoxy]propyl}-3-azetidinol hydrochloride

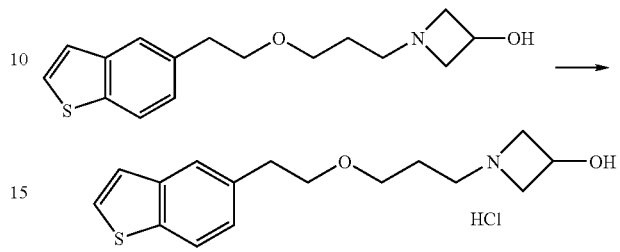

In the same manner as in Example 2, 1-{3-[2-(1-benzothiophen-5-yl)ethoxy]propyl}-3-azetidinol hydrochloride was obtained as colorless crystals.

Melting point: 71-73° C. IR (KBr) cm$^{-1}$: 3301, 2937, 2809, 2631, 1125, 1099, 818, 765, 710 NMR (CDCl$_3$) δ values: 1.8-1.9 (2H, m), 2.98 (2H, t, J=7 Hz), 2.9-3.1 (2H, m), 3.48 (2H, t, J=6 Hz), 3.69 (2H, t, J=7 Hz), 3.6-4.4 (4H, m), 4.5-4.7 (1H, m), 7.22 (1H, dd, J=1, 8 Hz), 7.31 (1H, d, J=5 Hz), 7.44 (1H, d, J=5 Hz), 7.68 (1H, d, J=1 Hz), 7.81 (1H, d, J=8 Hz)

EXAMPLE 11

Production of 1-{3-[2-(1-benzothiophen-4-yl) ethoxy]propyl}-3-azetidinol

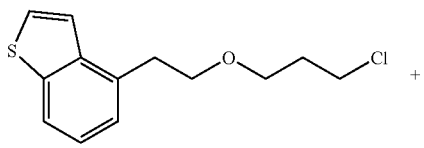

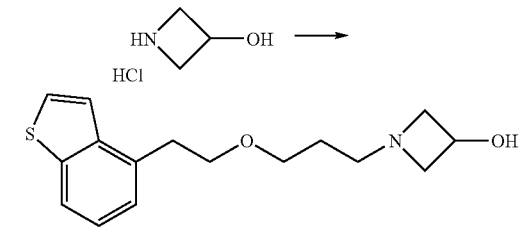

In the same manner as in Example 3, 1-{3-[2-(1-benzothiophen-4-yl)ethoxy]propyl}-3-azetidinol was obtained as a colorless oil.

IR (neat) cm$^{-1}$: 3368, 2946, 2856, 1457, 1107, 759 NMR (CDCl$_3$) δ values: 1.60 (2H, qn, J=7 Hz), 2.44 (2H, t, J=7 Hz), 2.7-2.9 (2H, m), 3.22 (2H, t, J=7 Hz), 3.45 (2H, t, J=7 Hz), 3.5-3.6 (2H, m), 3.70 (2H, t, J=7 Hz), 4.3-4.5 (1H, m), 7.19 (1H, d, J=7 Hz), 7.28 (1H, t, J=7 Hz), 7.44 (1H, d, J=6 Hz), 7.46 (1H, d, J=6 Hz), 7.76 (1H, d, J=7 Hz)

EXAMPLE 12

Production of 1-{3-[2-(1-benzothiophen-4-yl)ethoxy]propyl}-3-azetidinol hydrochloride

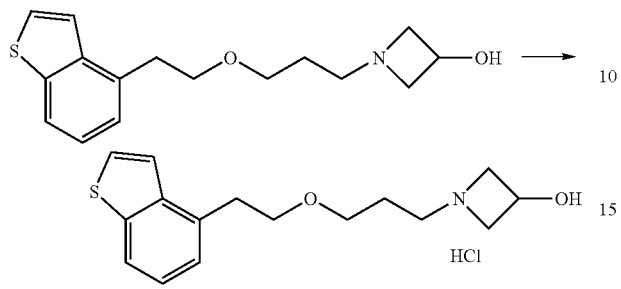

In the same manner as in Example 4, 1-{3-[2-(1-benzothiophen-4-yl)ethoxy]propyl}-3-azetidinol hydrochloride was obtained as a light-yellow oil.

IR (neat) cm$^{-1}$: 3302, 2966, 2877, 2594, 1412, 1108, 766 NMR (CDCl$_3$) δ values: 1.78 (2H, qn, J=6 Hz), 2.82 (2H, t, J=7 Hz), 3.21 (2H, t, J=6 Hz), 3.43 (2H, t, J=6 Hz), 3.73 (2H, t, J=6 Hz), 3.7-3.9 (2H, m), 3.8-4.0 (2H, m), 4.5-4.7 (1H, m), 7.21 (1H, d, J=7 Hz), 7.30 (1H, t, J=7 Hz), 7.49 (2H, s), 7.78 (1H, d, J=7 Hz)

EXAMPLE 13

Production of 1-{3-[2-(1-benzothiophen-3-yl)ethoxy]propyl}-3-azetidinol

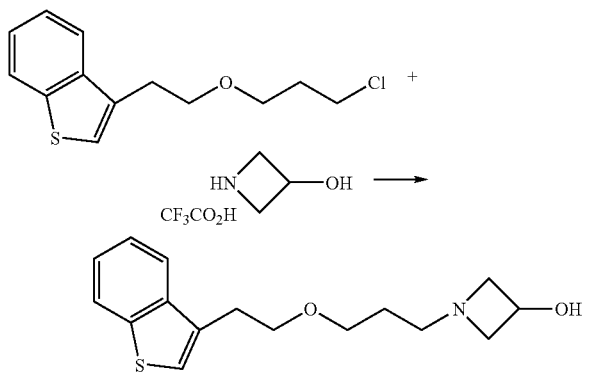

In 5 mL of dimethyl sulfoxide was dissolved 1.00 g of 3-[2-(3-chloropropoxy)ethyl]-1-benzothiophene, and 1.10 g of 3-azetidinol trifluoroacetate and 1.63 g of potassium carbonate were added to the solution, after which the resulting mixture was stirred at 70° C. for 2 hours. After the reaction mixture was cooled, water and ethyl acetate were added thereto and the pH was adjusted to 1 with 6 mol/L hydrochloric acid, and the aqueous layer was separated. Ethyl acetate was added to the aqueous layer and the pH was adjusted to 10 with a 2 mol/L aqueous sodium hydroxide solution, after which the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=30:1 to 10:1) to obtain 0.55 g of 1-{3-[2-(1-benzothiophen-3-yl)ethoxy]propyl}-3-azetidinol as a colorless oil.

IR (neat) cm$^{-1}$: 3368, 2942, 2845, 1427, 1191, 1109, 759 NMR (CDCl$_3$) δ values: 1.62 (2H, qn, J=7 Hz), 2.47 (2H, t, J=7 Hz), 2.7-2.9 (2H, m), 3.11 (2H, t, J=7 Hz), 3.48 (2H, t, J=6 Hz), 3.5-3.7 (2H, m), 3.74 (2H, t, J=7 Hz), 4.3-4.5 (1H, m), 7.18 (1H, s), 7.33 (1H, dt, J=1, 7 Hz), 7.39 (1H, dt, J=1, 7 Hz), 7.77 (1H, dd, J=1, 7 Hz), 7.86 (1H, dd, J=1, 7 Hz)

EXAMPLE 14

Production of 1-{3-[2-(1-benzothiophen-3-yl)ethoxy]propyl}-3-azetidinol hydrochloride

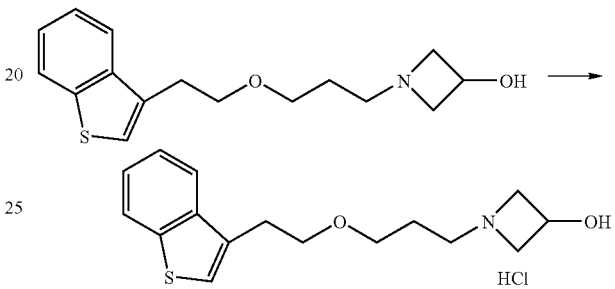

In the same manner as in Example 4, 1-{3-[2-(1-benzothiophen-3-yl)ethoxy]propyl}-3-azetidinol hydrochloride was obtained as a light-yellow oil.

IR (neat) cm$^{-1}$: 3284, 2966, 2596, 1428, 1112, 1049, 765, 734 NMR (CDCl$_3$) δ values: 1.83 (2H, qn, J=6 Hz), 2.96 (2H, t, J=6 Hz), 3.12 (2H, t, J=6 Hz), 3.48 (2H, t, J=6 Hz), 3.76 (2H, t, J=6 Hz), 3.8-3.9 (2H, m), 3.9-4.1 (2H, m), 4.5-4.7 (1H, m), 7.21 (1H, s), 7.35 (1H, dt, J=1, 7 Hz), 7.40 (1H, dt, J=1, 7 Hz), 7.78 (1H, dd, J=1.7 Hz), 7.86 (1H, dd, J=1, 7 Hz)

EXAMPLE 15

Production of N-(1-{3-[2-(1-benzothiophen-5-yl)ethoxy]propyl}-3-azetidinyl)acetamide

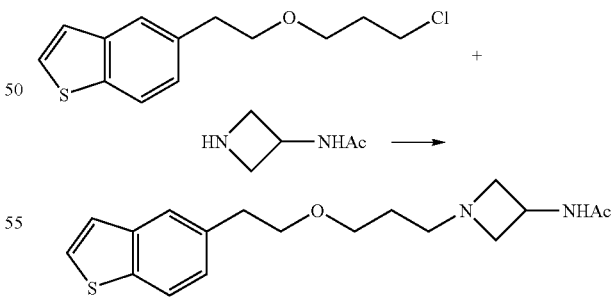

In 8 mL of N,N-dimethylformamide was dissolved 0.80 g of 5-[2-(3-chloropropoxy)ethyl]-1-benzothiophene, and 1.20 g of N-(3-azetidinyl)acetamide was added to the solution, after which the resulting mixture was stirred at 90° C. for 12 hours. After the reaction mixture was cooled, water and ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=7:1) to obtain 0.39 g of N-(1-{3-[2-(1-benzothiophen-5-yl)ethoxy]propyl}-3-azetidinyl)acetamide as a light-yellow oil.

IR (neat) cm$^{-1}$: 3276, 2941, 2860, 1654, 1559, 1111, 756, 703 NMR (CDCl$_3$) δ values: 1.59 (2H, qn, J=7 Hz), 1.97 (3H, s), 2.42 (2H, t, J=7 Hz), 2.7-2.9 (2H, m), 2.98 (2H, t, J=7 Hz), 3.45 (2H, t, J=7 Hz), 3.4-3.6 (2H, m), 3.66 (2H, t, J=7 Hz), 4.4-4.5 (1H, m), 7.22 (1H, dd, J=1, 8 Hz), 7.29 (1H, d, J=5 Hz), 7.42 (1H, d, J=5 Hz), 7.67 (1H, d, J=1 Hz), 7.80 (1H, d, J=8 Hz)

EXAMPLE 16

Production of 1-{2-[2-(1-benzothiophen-6-yl)ethoxy]ethyl}-3-pyrrolidinol

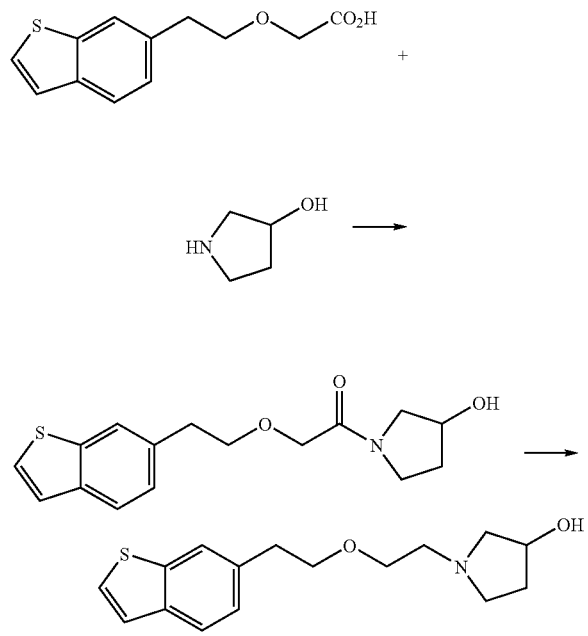

(1) In 7.4 mL of methylene chloride was dissolved 0.74 g of 2-[2-(1-benzothiophen-6-yl)ethoxy]acetic acid, and 1.36 mL of triethylamine and 0.22 g of imidazole were added to the solution. Then, the resulting mixture was cooled to 5° C., after which 0.24 mL of thionyl chloride was added dropwise thereto, followed by stirring at the same temperature for 1 hour. After the reaction mixture was cooled to −50° C., 0.45 mL of triethylamine and 0.32 mL of 3-pyrrolidinol were added thereto, and the resulting mixture was stirred at the same temperature for 1 hour and then at room temperature for 1 hour. Water was added to the reaction mixture and the organic layer was separated. The organic layer was washed successively with 1 mol/L hydrochloric acid, a 2 mol/L aqueous sodium hydroxide solution and a saturated aqueous sodium chloride solution, and then dried over anhydrous magnesium sulfate. Subsequently, the solvent was distilled off under reduced pressure to obtain 2-[2-(1-benzothiophen-6-yl)ethoxy]-1-(3-hydroxy-1-pyrrolidinyl)-1-ethanone as a light-yellow oil.

IR (neat) cm$^{-1}$: 3386, 2942, 1636, 1106, 758

(2) The aforesaid 2-[2-(1-benzothiophen-6-yl)ethoxy]-1-(3-hydroxy-1-pyrrolidinyl)-1-ethanone was dissolved in 7.4 mL of tetrahydrofuran, and 7.4 mL of a 1 mol/L solution of a borane-tetrahydrofuran complex in tetrahydrofuran was added dropwise thereto under ice-cooling, followed by stirring at room temperature for 17 hours. To the reaction mixture was added 10 mL of acetone, and stirred for 30 minutes, after which 1.5 mL of 6 mol/L hydrochloric acid was added thereto and the resulting mixture was heated under reflux for 2 hours. After the reaction mixture was cooled, water and ethyl acetate were added thereto and the aqueous layer was separated. Ethyl acetate was added to the aqueous layer and the pH was adjusted to 9.5 with a 2 mol/L aqueous sodium hydroxide solution, after which the organic layer was separated. The organic layer was washed with water and a saturated aqueous sodium chloride solution, dried over anhydrous magnesium sulfate, and then distilled under reduced pressure to remove the solvent. The residue was purified by a column chromatography (eluent; chloroform:methanol=30:1 to 20:1) to obtain 0.53 g of 1-{2-[2-(1-benzothiophen-6-yl)ethoxy]ethyl}-3-pyrrolidinol as a yellow oil.

IR (neat) cm$^{-1}$: 3386, 2940, 2867, 1110, 820, 756 NMR (CDCl$_3$) δ values: 1.6-1.8 (1H, m), 2.0-2.2 (1H, m), 2.31 (1H, dt, J=7, 9 Hz), 2.53 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.73 (1H, s)

EXAMPLE 17

Production of 1-{2-[2-(1-benzothiophen-6-yl)ethoxy]ethyl}-3-pyrrolidinol oxalate

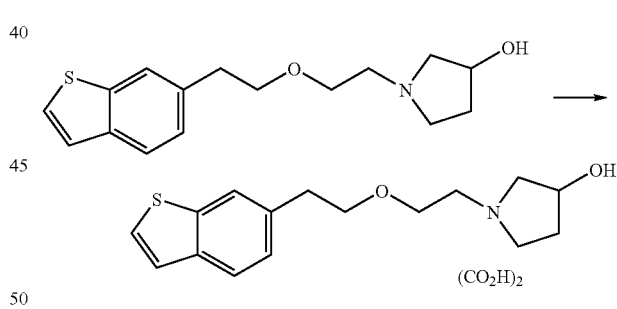

In 2.0 mL of ethyl acetate was dissolved 0.48 g of 1-{2-[2-(1-benzothiophen-6-yl)ethoxy]ethyl}-3-pyrrolidinol, and to the solution was added a solution of 0.15 g of oxalic acid in 2.8 mL of ethyl acetate. The resulting mixture was stirred at room temperature for 1 hour and then at 5° C. for 1 hour. The crystals precipitated were collected by filtration, washed with ethyl acetate and then dried to obtain 0.42 g of 1-{2-[2-(1-benzothiophen-6-yl)ethoxy]ethyl}-3-pyrrolidinol oxalate as colorless crystals.

IR (KBr) cm$^{-1}$: 3384, 2862, 2687, 1717, 1636, 1400, 1200, 1114, 720 NMR (DMSO-d$_6$) δ values: 1.7-1.8 (1H, m), 1.9-2.1 (1H, m), 2.96 (2H, t, J=7 Hz), 3.0-3.2 (1H, m), 3.1-3.4 (5H, m), 3.6-3.8 (4H, m), 4.3-4.4 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

EXAMPLE 18

Production of 1-{2-[2-(1-benzothiophen-5-yl)ethoxy]ethyl}-3-pyrrolidinol

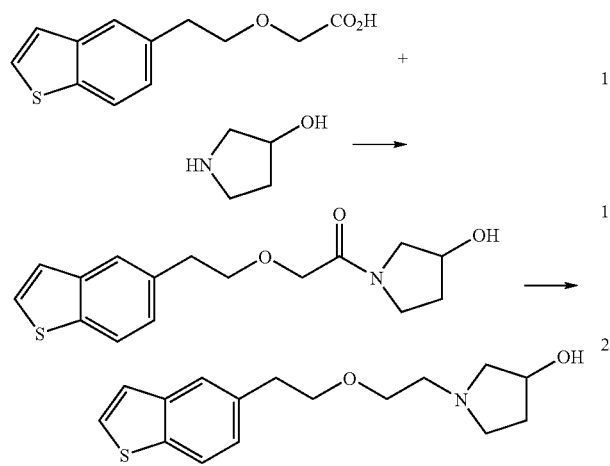

In the same manner as in Example 16 (1), 2-[2-(1-benzothiophen-5-yl)ethoxy]-1-(3-hydroxy-1-pyrrolidinyl)-1-ethanone was obtained.

NMR (CDCl$_3$) δ values: 1.6-2.2 (2H, m), 2.9-4.0 (8H, m), 4.0-4.2 (2H, m), 4.2-4.5 (1H, m), 7.1-7.4 (2H, m), 7.42 (1H, d, J=5 Hz), 7.69 (1H, s), 7.79 (1H, d, J=8 Hz)

Then, 1-{2-[2-(1-benzothiophen-5-yl)ethoxy]ethyl}-3-pyrrolidinol was obtained as a light-yellow oil in the same manner as in Example 16 (2).

IR (neat) cm$^{-1}$: 3386, 2941, 2864, 1438, 1112, 755, 702
NMR (CDCl$_3$) δ values: 1.5-2.0 (1H, m), 2.0-2.9 (7H, m), 3.00 (2H, t, J=7 Hz), 3.58 (2H, t, J=6 Hz), 3.71 (2H, t, J=7 Hz), 4.2-4.4 (1H, m), 7.21 (1H, d, J=8 Hz), 7.28 (1H, d, J=5 Hz), 7.42 (1H, d, J=5 Hz), 7.67 (1H, s), 7.79 (1H, d, J=8 Hz)

EXAMPLE 19

Production of 1-{2-[2-(1-benzothiophen-5-yl)ethoxy]ethyl}-3-pyrrolidinol oxalate

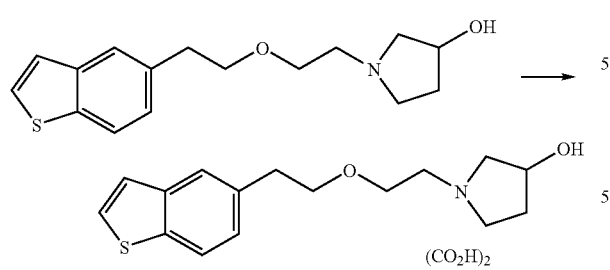

In the same manner as in Example 17, 1-{2-[2-(1-benzothiophen-5-yl)ethoxy]ethyl}-3-pyrrolidinol oxalate was obtained as colorless crystals.

IR (KBr) cm$^-$: 3347, 2943, 2687, 1719, 1404, 1119, 720
NMR (CDCl$_3$) δ values: 1.7-2.2 (2H, m), 2.9-3.8 (6H, m), 2.94 (2H, t, J=6 Hz), 3.68 (4H, t, J=6 Hz), 4.2-4.5 (1H, m), 7.17 (1H, d, J=8 Hz), 7.26 (1H, d, J=5 Hz), 7.42 (1H, d, J=5 Hz), 7.62 (1H, s), 7.78 (1H, d, J=8 Hz)

EXAMPLE 20

Production of 1-{2-[2-(1-benzothiophen-4-yl)ethoxy]ethyl}-3-pyrrolidinol

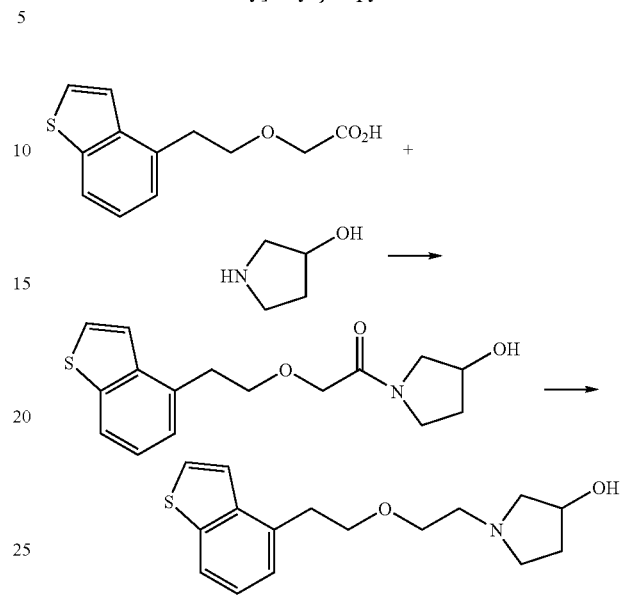

In the same manner as in Example 16 (1), 2-[2-(1-benzothiophen-4-yl)ethoxy]-1-(3-hydroxy-1-pyrrolidinyl)-1-ethanone was obtained as an oil.

IR (neat) cm$^{-1}$: 3374, 2944, 1637, 1107, 761

Then, 1-{2-[2-(1-benzothiophen-4-yl)ethoxy]ethyl}-3-pyrrolidinol was obtained as a light-yellow oil in the same manner as in Example 16 (2).

IR (neat) cm$^{-1}$: 3376, 2939, 2867, 1452, 1413, 1111, 760
NMR (CDCl$_3$) δ values: 1.6-1.8 (1H, m), 2.1-2.2 (1H, m), 2.30 (1H, dt, J=6, 9 Hz), 2.53 (1H, dd, J=5, 10 Hz), 2.6-2.7 (3H, m), 2.85 (1H, dt, J=5, 9 Hz), 3.25 (2H, t, J=7 Hz), 3.58 (2H, t, J=6 Hz), 3.75 (2H, t, J=7 Hz), 4.2-4.4 (1H, m), 7.20 (1H, d, J=7 Hz), 7.27 (1H, t, J=7 Hz), 7.44 (1H, d, J=6 Hz), 7.46 (1H, d, J=6 Hz), 7.75 (1H, d, J=7 Hz)

EXAMPLE 21

Production of 1-{2-[2-(1-benzothiophen-4-yl)ethoxy]ethyl}-3-pyrrolidinol hydrochloride

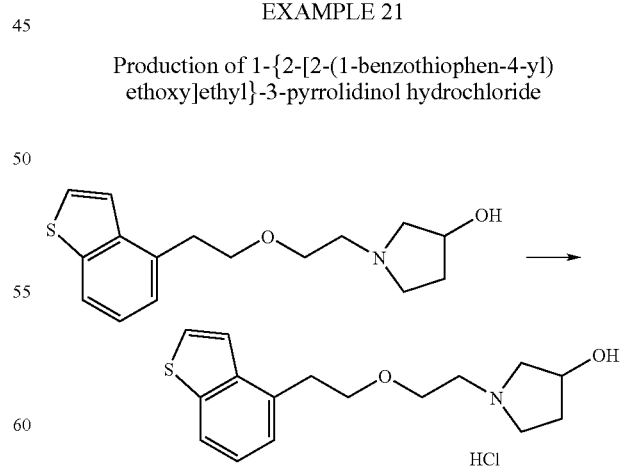

In 5.0 mL of ethyl acetate was dissolved 0.63 g of 1-{2-[2-(1-benzothiophen-4-yl)ethoxy]ethyl}-3-pyrrolidinol, and to the solution was added 0.80 mL of a 3.25 mol/L dried hydrogen chloride-ethyl acetate solution. The resulting mixture was stirred at room temperature for 1 hour and then at 5° C. for 1 hour, after which the crystals precipitated were collected by filtration. The crystals precipitated were washed with ethyl acetate and then dried to obtain 0.43 g of 1-{2-[2-(1-benzothiophen-4-yl)ethoxy]ethyl}-3-pyrrolidinol hydrochloride as colorless crystals.

IR (KBr) cm$^{-1}$: 3229, 2872, 2625, 1451, 1413, 1119, 771 NMR (DMSO-d$_6$) δ values: 1.7-2.2 (2H, m), 2.9-3.6 (6H, m), 3.22 (2H, t, J=7 Hz), 3.74 (4H, t, J=7 Hz), 4.3-4.4 (1H, m), 7.27 (1H, d, J=8 Hz), 7.30 (1H, t, J=8 Hz), 7.61 (1H, d, J=5 Hz), 7.77 (1H, d, J=5 Hz), 7.86 (1H, d, J=8 Hz)

EXAMPLE 22

Production of 1-{2-[2-(1-benzothiophen-7-yl)ethoxy]ethyl}-3-pyrrolidinol

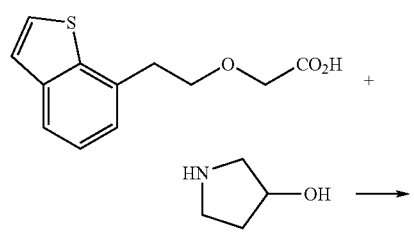

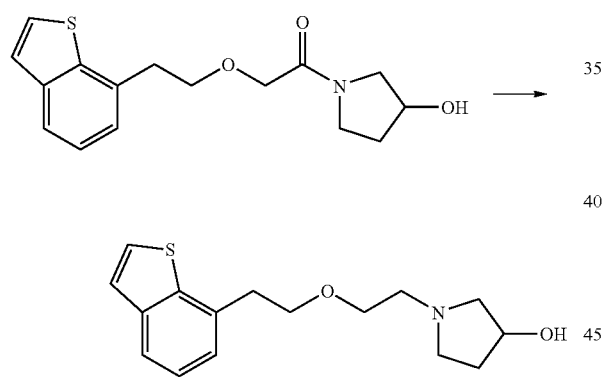

In the same manner as in Example 16 (1), 2-[2-(1-benzothiophen-7-yl)ethoxy]-1-(3-hydroxy-1-pyrrolidinyl)-1-ethanone was obtained as an oil.

NMR (CDCl$_3$) δ values: 1.8-2.0 (2H, m), 3.1-3.3 (3H, m), 3.3-3.6 (3H, m) 3.8-4.0 (2H, m), 4.0-4.2 (2H, m), 4.3-4.5 (1H, m), 7.23 (1H, d, J=7 Hz), 7.3-7.4 (2H, m), 7.4-7.5 (1H, m), 7.6-7.8 (1H, m)

Then, 1-{2-[2-(1-benzothiophen-7-yl)ethoxy]ethyl}-3-pyrrolidinol was obtained as a colorless oil in the same manner as in Example 16 (2).

IR (neat) cm$^{-1}$: 3385, 2941, 2867, 1459, 1395, 1106, 795, 754, 701 NMR (CDCl$_3$) δ values: 1.6-1.8 (1H, m), 2.1-2.2 (1H, m), 2.30 (1H, dt, J=7, 9 Hz), 2.52 (1H, dd, J=5, 10 Hz), 2.6-2.7 (3H, m), 2.85 (1H, dt, J=5, 9 Hz), 3.19 (2H, t, J=7 Hz), 3.59 (2H, t, J=6 Hz), 3.84 (2H, t, J=7 Hz), 4.2-4.4 (1H, m), 7.20 (1H, d, J=8 Hz), 7.32 (1H, t, J=8 Hz), 7.35 (1H, d, J=5 Hz,), 7.42 (1H, d, J=5 Hz), 7.69 (1H, d, J=8 Hz)

EXAMPLE 23

Production of 1-{2-[2-(1-benzothiophen-7-yl)ethoxy]ethyl}-3-pyrrolidinol hydrochloride

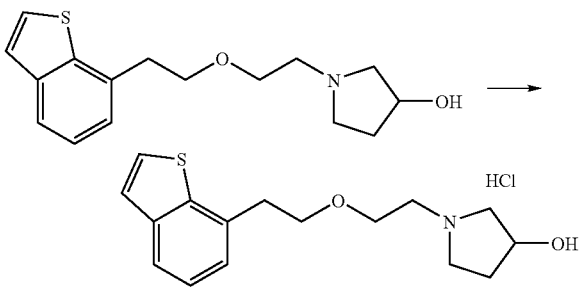

In the same manner as in Example 21, 1-{2-[2-(1-benzothiophen-7-yl)ethoxy]ethyl}-3-pyrrolidinol hydrochloride was obtained as colorless crystals.

IR (KBr) cm$^{-1}$: 3283, 2938, 2706, 1395, 1358, 1125, 810, 720 NMR (DMSO-d$_6$) δ values: 1.7-2.2 (2H, m), 2.8-3.7 (6H, m), 3.12 (2H, t, J=7 Hz), 3.7-3.8 (2H, m), 3.82 (2H, t, J=7 Hz), 4.3-4.4 (1H, m), 7.29 (1H, d, J=7 Hz), 7.36 (1H, t, J=7 Hz), 7.49 (1H, d, J=5 Hz), 7.76 (1H, d, J=5 Hz), 7.77 (1H, d, J=7 Hz)

EXAMPLE 24

Production of 1-{2-[2-(1-benzothiophen-2-yl)ethoxy]ethyl}-3-pyrrolidinol

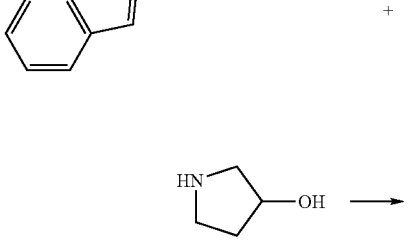

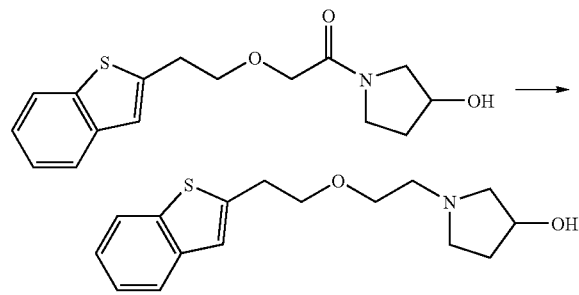

In the same manner as in Example 16 (1), 2-[2-(1-benzothiophen-2-yl)ethoxy]-1-(3-hydroxy-1-pyrrolidinyl)-1-ethanone was obtained.

NMR (CDCl$_3$) δ values: 1.8-2.0 (2H, m), 3.1-3.3 (3H, m), 3.3-3.7 (3H, m), 3.8-4.0 (2H, m), 4.1-4.2 (2H, m), 4.2-4.5 (1H, m), 7.10 (1H, s), 7.2-7.4 (2H, m), 7.6-7.7 (1H, m), 7.7-7.8 (1H, m)

Then, 1-{2-[2-(1-benzothiophen-2-yl)ethoxy]ethyl}-3-pyrrolidinol was obtained as a light-yellow oil in the same manner as in Example 16 (2).

IR (neat) cm$^{-1}$: 3396, 2939, 1458, 1438, 1113, 747, 727 NMR (CDCl$_3$) δ values: 1.6-1.8 (1H, m), 2.1-2.2 (1H, m), 2.34 (1H, dt, J=6, 9 Hz), 2.55 (1H, dd, J=5, 10 Hz), 2.6-2.8 (3H, m), 2.85 (1H, dt, J=5, 9 Hz), 3.18 (2H, dt, J=1, 7 Hz), 3.62 (2H, t, J=6 Hz), 3.77 (2H, t, J=7 Hz), 4.2-4.4 (1H, m), 7.07 (1H, s), 7.26 (1H, dt, J=1, 8 Hz), 7.31 (1H, dt, J=1, 8 Hz), 7.67 (1H, dd, J=1, 8 Hz), 7.76 (1H, dd, J=1, 8 Hz)

EXAMPLE 25

Production of 1-{2-[2-(1-benzothiophen-2-yl)ethoxy]ethyl}-3-pyrrolidinol oxalate

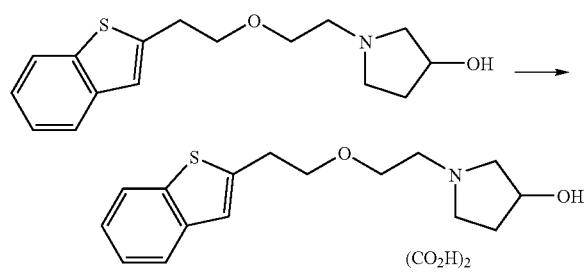

In the same manner as in Example 17, 1-{2-[2-(1-benzothiophen-2-yl)ethoxy]ethyl}-3-pyrrolidinol oxalate was obtained as colorless crystals.

IR (KBr) cm$^{-1}$: 3432, 2871, 1716, 1436, 1127, 827, 760, 706 NMR (DMSO-d$_6$) δ values: 1.7-1.8 (1H, m), 1.9-2.2 (1H, m), 3.0-3.4 (8H, m), 3.73 (4H, t, J=6 Hz), 4.2-4.4 (1H, m), 7.23 (1H, s), 7.28 (1H, t, J=7 Hz), 7.33 (1H, t, J=7 Hz), 7.74 (1H, d, J=7 Hz), 7.87 (1H, d, J=7 Hz)

EXAMPLE 26

Production of 1-{2-[2-(1-benzothiophen-3-yl)ethoxy]ethyl}-3-pyrrolidinol

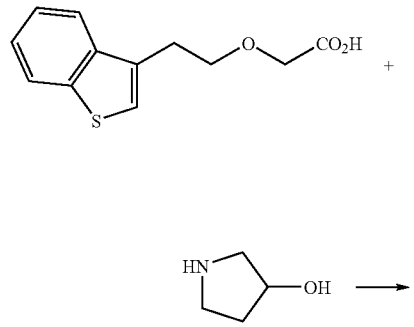

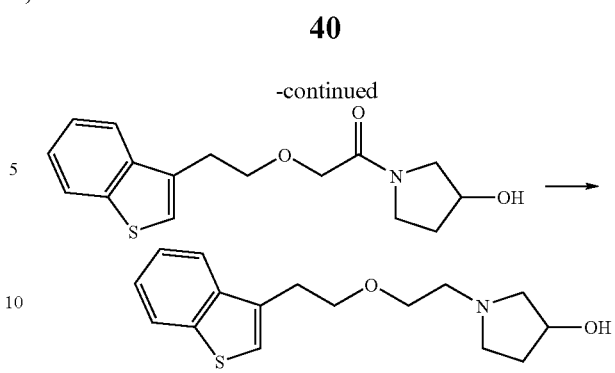

In the same manner as in Example 16 (1), 2-[2-(1-benzothiophen-3-yl)ethoxy]-1-(3-hydroxy-1-pyrrolidinyl)-1-ethanone was obtained as an oil.

NMR (CDCl$_3$) δ values: 1.8-1.9 (1H, m), 1.9-2.0 (1H, m), 3.1-3.6 (6H, m), 3.8-4.0 (2H, m), 4.09 (1H, s), 4.13 (1H, s), 4.3-4.5 (1H, m), 7.26 (1H, s), 7.3-7.4 (2H, m), 7.77 (1H, d, J=8 Hz), 7.85 (1H, d, J=8 Hz)

Then, 1-{2-[2-(1-benzothiophen-3-yl)ethoxy]ethyl}-3-pyrrolidinol was obtained as a light-yellow oil in the same manner as in Example 16 (2).

IR (neat) cm$^{-1}$: 3388, 2934, 1426, 1112, 761, 733 NMR (CDCl$_3$) δ values: 1.6-1.8 (1H, m), 2.1-2.2 (1H, m), 2.33 (1H, dt, J=6, 9 Hz), 2.56 (1H, dd, J=5, 10 Hz), 2.6-2.8 (3H, m), 2.87 (1H, dt, J=5, 9 Hz), 3.14 (2H, dt, J=1, 7 Hz), 3.61 (2H, t, J=6 Hz), 3.80 (2H, t, J=7 Hz), 4.3-4.4 (1H, m), 7.20 (1H, s), 7.34 (1H, dt, J=1, 7 Hz), 7.38 (1H, dt, J=1, 7 Hz), 7.77 (1H, dd, J=1, 7 Hz), 7.85 (1H, dd, J=1, 7 Hz)

EXAMPLE 27

Production of 1-{2-[2-(1-benzothiophen-3-yl)ethoxy]ethyl}-3-pyrrolidinol oxalate

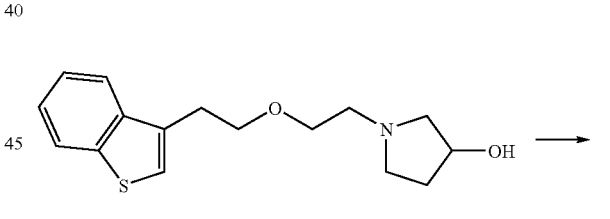

In the same manner as in Example 17, 1-{2-[2-(1-benzothiophen-3-yl)ethoxy]ethyl}-3-pyrrolidinol oxalate was obtained as colorless crystals.

IR (KBr) cm$^{-1}$: 3363, 2922, 2691, 1718, 1636, 1427, 1404, 1119, 767, 721 NMR (DMSO-d$_6$) δ values: 1.7-1.8 (1H, m), 2.0-2.2 (1H, m), 3.10 (2H, t, J=7 Hz), 3.1-3.4 (6H, m), 3.72 (2H, t, J=5 Hz), 3.78 (2H, t, J=7 Hz), 4.3-4.4 (1H, m), 7.37 (1H, t, J=8 Hz), 7.42 (1H, t, J=8 Hz), 7.51 (1H, s), 7.85 (1H, d, J=8 Hz), 7.98 (1H, d, J=8 Hz)

EXAMPLE 28

Production of 1-{2-[2-(1-naphthyl)ethoxy]-ethyl}-3-pyrrolidinol

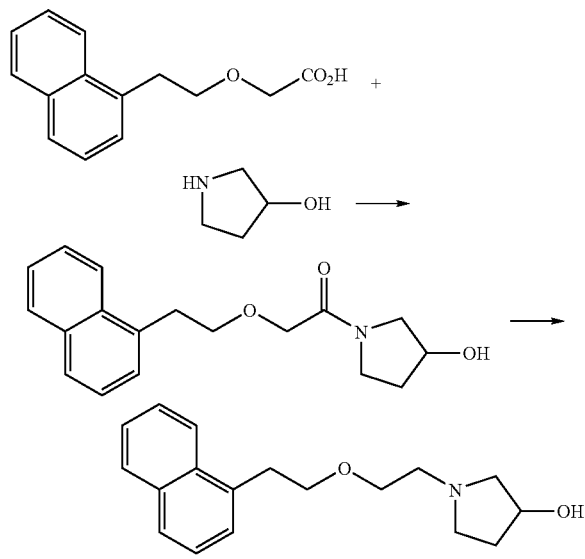

In the same manner as in Example 16 (1), 2-[2-(1-naphthyl)ethoxy]-1-(3-hydroxy-1-pyrrolidinyl)-1-ethanone was obtained as a yellow oil.

IR (neat) cm$^{-1}$: 3392, 2946, 1645, 1133, 800, 779

Then, 1-{2-[2-(1-naphthyl)ethoxy]ethyl}-3-pyrrolidinol was obtained as a light-yellow oil in the same manner as in Example 16 (2).

IR (neat) cm$^{-1}$: 3395, 2944, 1107, 778 NMR (CDCl$_3$) δ values: 1.5-1.9 (1H, m), 2.0-2.5 (3H, m), 2.5-3.0 (4H, m), 3.37 (2H, t, J=7 Hz), 3.59 (2H, t, J=6 Hz), 3.80 (2H, t, J=7 Hz), 4.2-4.4 (1H, m), 7.4-7.6 (4H, m), 7.6-8.0 (2H, m), 8.0-8.2 (1H, m)

EXAMPLE 29

Production of 1-{2-[2-(1-naphthyl)ethoxy]-ethyl}-3-pyrrolidinol oxalate

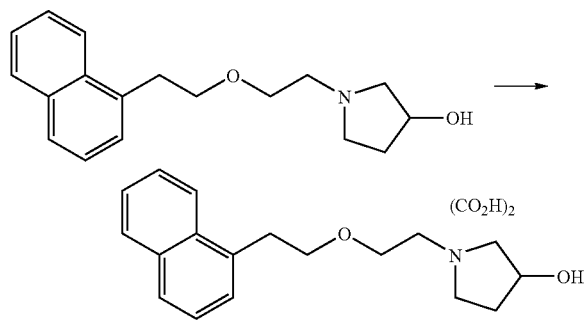

In the same manner as in Example 17, 1-{2-[2-(1-naphthyl)ethoxy]ethyl}-3-pyrrolidinol oxalate was obtained as colorless crystals.

IR (KBr) cm$^{-1}$: 3366, 1400, 1116, 780, 720 NMR (DMSO-d$_6$) δ values: 1.6-2.3 (2H, m), 2.7-3.5 (8H, m), 3.5-3.9 (4H, m), 4.2-4.5 (1H, m), 7.4-7.6 (4H, m), 7.7-8.0 (2H, m), 8.0-8.2 (1H, m)

EXAMPLE 30

Production of (3S)-1-{2-[2-(1-benzothiophen-5-yl)ethoxy]ethyl}-3-pyrrolidinol

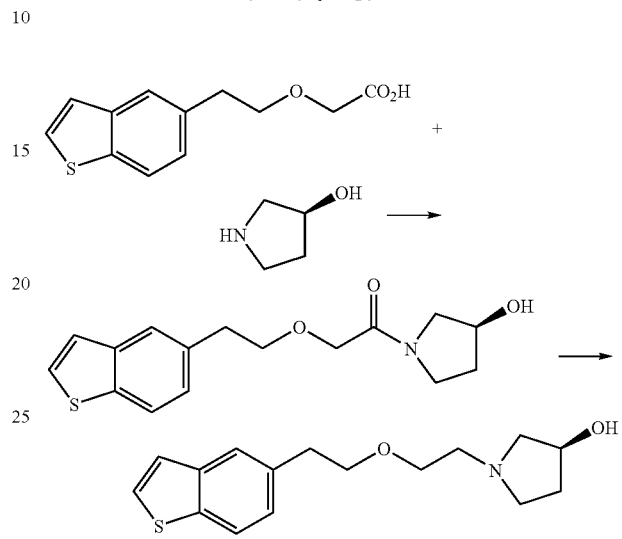

In the same manner as in Example 16 (1), 2-[2-(1-benzothiophen-5-yl)ethoxy]-1-[(3S)-3-hydroxy-1-pyrrolidinyl]-1-ethanone was obtained as a light-yellow oil.

Then, (3S)-1-{2-[2-(1-benzothiophen-5-yl)ethoxy]ethyl}-3-pyrrolidinol was obtained as a light-yellow oil in the same manner as in Example 16 (2).

IR (neat) cm$^{-1}$: 3386, 2936, 2867, 1438, 1111, 755, 702 NMR (CDCl$_3$) δ values: 1.5-2.0 (1H, m), 2.0-3.0 (5H, m), 2.66 (2H, t, J=6 Hz), 3.00 (2H, t, J=7 Hz), 3.58 (2H, t, J=6 Hz), 3.71 (2H, t, J=7 Hz), 4.2-4.4 (1H, m), 7.21 (1H, d, J=8 Hz), 7.28 (1H, d, t=5 Hz), 7.42 (1H, d, J=5 Hz), 7.67 (1H, s), 7.79 (1H, d, J=8 Hz)

EXAMPLE 31

Production of (3S)-1-{2-[2-(1-benzothiophen-5-yl)ethoxy]ethyl}-3-pyrrolidinol oxalate

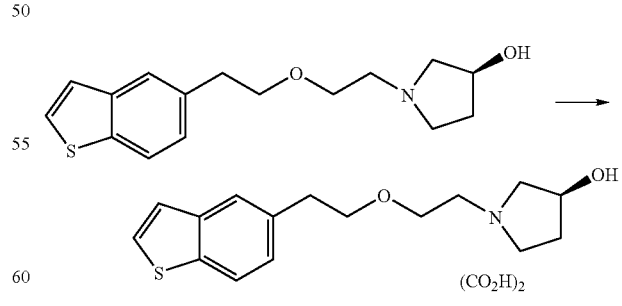

In the same manner as in Example 17, (3S)-1-{2-[2-(1-benzothiophen-5-yl)ethoxy]ethyl}-3-pyrrolidinol oxalate was obtained as colorless crystals.

IR (KBr) cm$^{-1}$: 3366, 2941, 2867, 2686, 1718, 1701, 1404, 1114, 720 NMR (DMSO-d$_6$) δ values: 1.5-2.2 (2H, m), 2.8-

3.5 (8H, m), 3.70 (4H, t, J=6 Hz), 4.2-4.5 (1H, m), 7.28 (1H, d, J=8 Hz), 7.40 (1H, d, J=5 Hz), 7.73 (1H, d, J=5 Hz), 7.76 (1H, s), 7.91 (1H, d, J=8 Hz)

EXAMPLE 32

Production of (3R)-1-{2-[2-(1-benzothiophen-5-yl)ethoxy]ethyl}-3-pyrrolidinol

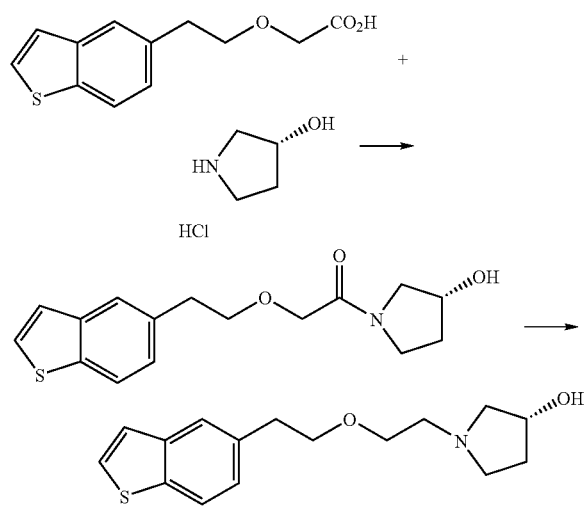

In the same manner as in Example 16 (1), 2-[2-(1-benzothiophen-5-yl)ethoxy]-1-[(3R)-3-hydroxy-1-pyrrolidinyl]-1-ethanone was obtained as colorless crystals.

IR (KBr) cm$^{-1}$: 3408, 2937, 1637, 1137, 1108, 812, 703

Then, (3R)-1-{2-[2-(1-benzothiophen-5-yl)ethoxy]ethyl}-3-pyrrolidinol was obtained as a light-yellow oil in the same manner as in Example 16 (2).

IR (neat) cm$^{-1}$: 3373, 2940, 1438, 1111, 755, 702 NMR (CDCl$_3$) δ values: 1.5-2.0 (1H, m), 2.0-3.0 (5H, m), 2.68 (2H, t, J=6 Hz), 3.01 (2H, t, J=7 Hz), 3.59 (2H, t, J=6 Hz), 3.71 (2H, t, J=7 Hz), 4.2-4.4 (1H, m), 7.21 (1H, d, J=8 Hz), 7.28 (1H, d, J=5 Hz), 7.42 (1H, d, J=5 Hz), 7.67 (1H, s), 7.79 (1H, d, J=8 Hz)

EXAMPLE 33

Production of (3R)-1-{2-[2-(1-benzothiophen-5-yl)ethoxy]ethyl}-3-pyrrolidinol oxalate

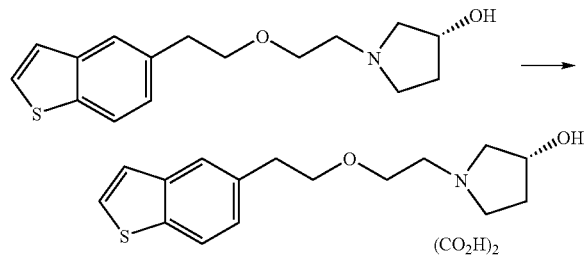

In the same manner as in Example 17, (3R)-1-{2-[2-(1-benzothiophen-5-yl)ethoxy]ethyl}-3-pyrrolidinol oxalate was obtained as colorless crystals.

IR (KBr) cm$^{-1}$: 3318, 2870, 1718, 1114, 720 NMR (DMSO-d$_6$) δ values: 1.5-2.2 (2H, m), 2.8-3.5 (8H, m), 3.70 (4H, t, J=6 Hz), 4.2-4.5 (1H, m), 7.28 (1H, d, J=8 Hz), 7.40 (1H, d, J=5 Hz), 7.73 (1H, d, J=5 Hz), 7.76 (1H, s), 7.91 (1H, d, J=8 Hz)

EXAMPLE 34

Production of (3S)-1-{2-[2-(1-benzothiophen-6-yl)ethoxy]ethyl}-3-pyrrolidinol

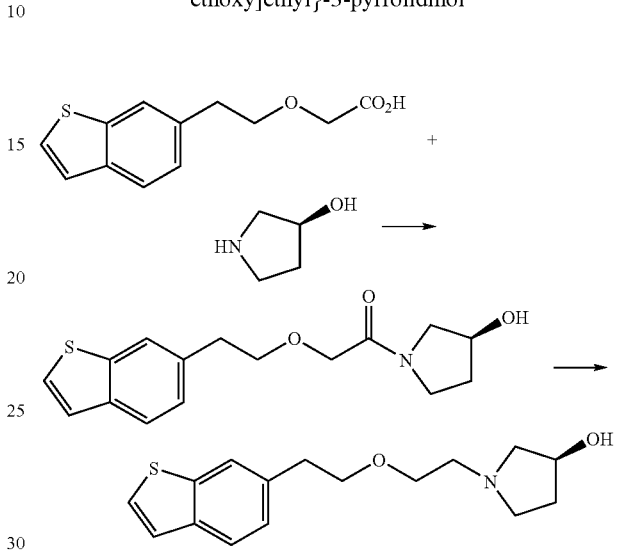

In the same manner as in Example 16 (1), 2-[2-(1-benzothiophen-6-yl)ethoxy]-1-[(3S)-3-hydroxy-1-pyrrolidinyl]-1-ethanone was obtained as a colorless oil.

IR (neat) cm$^{-1}$: 3385, 2944, 1637, 1133, 820, 699

Then, (3S)-1-{2-[2-(1-benzothiophen-6-yl)ethoxy]ethyl}-3-pyrrolidinol was obtained as a colorless oil in the same manner as in Example 16 (2).

IR (neat) cm$^{-1}$: 3385, 2940, 2867, 1110, 820, 757 NMR (CDCl$_3$) δ values: 1.6-1.8 (1H, m), 2.1-2.2 (1H, m), 2.32 (1H, dt, J=6, 9 Hz), 2.54 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.74 (1H, s)

EXAMPLE 35

Production of (3S)-1-{2-[2-(1-benzothiophen-6-yl)ethoxy]ethyl}-3-pyrrolidinol oxalate

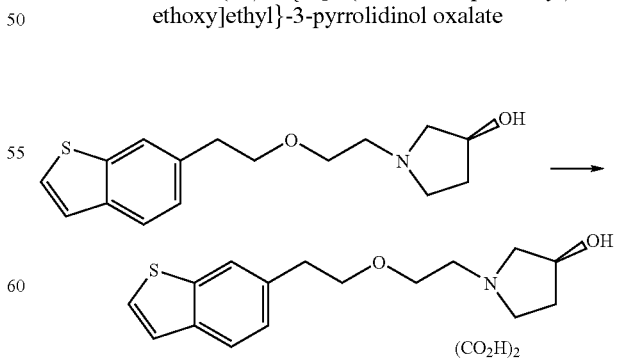

In the same manner as in Example 17, (3S)-1-{2-[2-(1-benzothiophen-6-yl)ethoxy]ethyl}-3-pyrrolidinol oxalate was obtained as colorless crystals.

IR (KBr) cm$^{-1}$: 3364, 2938, 2692, 1718, 1400, 1201, 1114, 720 NMR (DMSO-d$_6$) δ values: 1.7-1.8 (1H, m), 1.9-2.1 (1H, m), 2.96 (2H, t, J=7 Hz) 3.0-3.1 (1H, m), 3.1-3.3 (5H, m), 3.70 (4H, t, J=7 HZ), 4.2-4.3 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

EXAMPLE 36

Production of (3R)-1-{2-[2-(1-benzothiophen-6-yl)ethoxy]ethyl}-3-pyrrolidinol

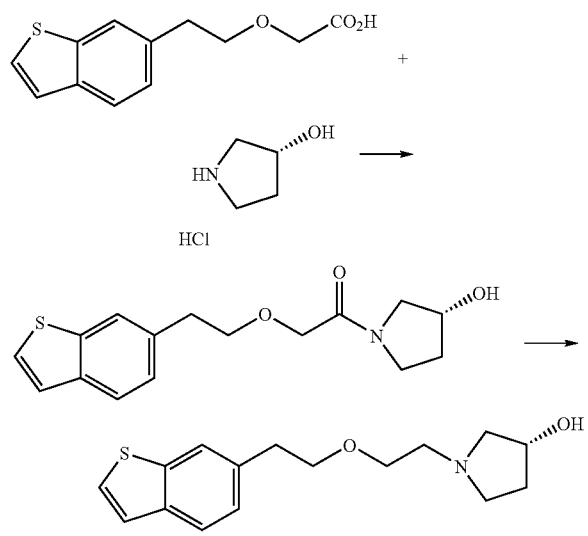

In the same manner as in Example 16 (1), 2-[2-(1-benzothiophen-6-yl)ethoxy]-1-[(3R)-3-hydroxy-1-pyrrolidinyl]-1-ethanone was obtained as an oil.

IR (neat) cm$^{-1}$: 3386, 2940, 1637, 1107, 820, 758

Then, (3R)-1-{2-[2-(1-benzothiophen-6-yl)ethoxy]ethyl}-3-pyrrolidinol was obtained as a colorless oil in the same manner as in Example 16 (2).

IR (neat) cm$^{-1}$: 3385, 2940, 2867, 1110, 820, 757 NMR (CDCl$_3$) δ values: 1.6-1.8 (1H, m), 2.1-2.2 (1H, m), 2.32 (1H, dt, J=6, 9 Hz), 2.54 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.74 (1H, s)

EXAMPLE 37

Production of (3R)-1-{2-[2-(1-benzothiophen-6-yl)ethoxy]ethyl}-3-pyrrolidinol oxalate

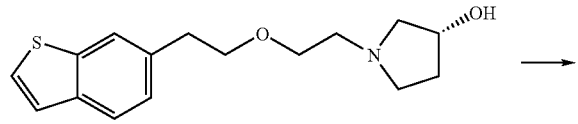

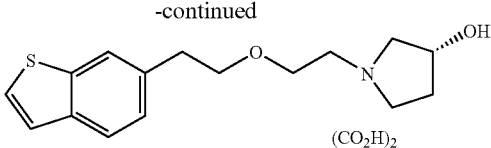

(CO$_2$H)$_2$

In the same manner as in Example 17, (3R)-1-{2-[2-(1-benzothiophen-6-yl)ethoxy]ethyl}-3-pyrrolidinol oxalate was obtained as colorless crystals.

IR (KBr) cm$^{-1}$: 3364, 2938, 2688, 1718, 1400, 1201, 1114, 720 NMR (DMSO-d$_6$) δ values: 1.7-1.8 (1H, m), 1.9-2.1 (1H, m), 2.96 (2H, t, J=7 Hz), 3.0-3.1 (1H, m), 3.1-3.3 (5H, m), 3.70 (4H, t, J=7 Hz), 4.2-4.3 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

EXAMPLE 38

Production of (3R)-1-{2-[2-(1-benzothiophen-3-yl)ethoxy]ethyl}-3-pyrrolidinol

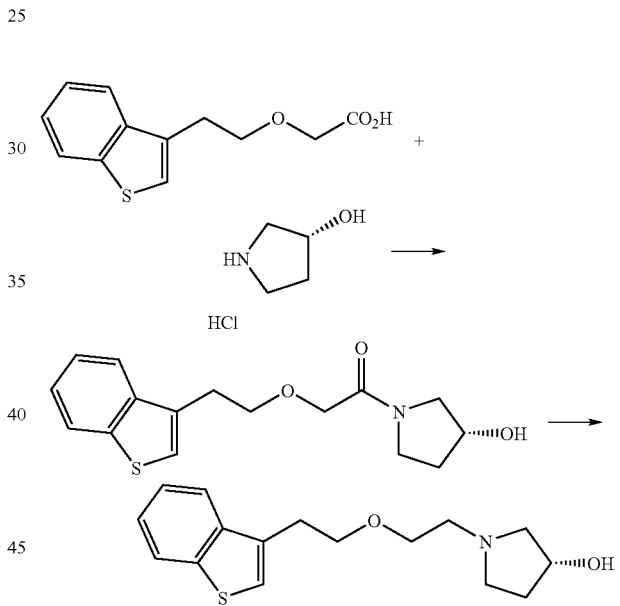

In the same manner as in Example 16 (1), 2-[2-(1-benzothiophen-3-yl)ethoxy]-1-[(3R)-3-hydroxy-1-pyrrolidinyl]-1-ethanone was obtained.

NMR (CDCl$_3$) δ values: 1.8-1.9 (1H, m), 1.9-2.0 (1H, m), 3.1-3.4 (3H, m), 3.3-3.7 (3H, m), 3.8-4.0 (2H, m), 4.0-4.2 (2H, m), 4.3-4.5 (1H, m), 7.27 (1/2H, s), 7.28 (1/2H, s), 7.3-7.5 (2H, m), 7.7-7.8 (1H, m), 7.8-7.9 (1H, m)

Then, (3R)-1-{2-[2-(1-benzothiophen-3-yl)ethoxy]ethyl}-3-pyrrolidinol was obtained as a yellow oil in the same manner as in Example 16 (2).

IR (neat) cm$^{-1}$: 3386, 2942, 1458, 1429, 1113, 759, 733 NMR (CDCl$_3$) δ values: 1.6-1.8 (1H, m), 2.1-2.2 (1H, m), 2.34 (1H, dt, J=6, 9 Hz), 2.55 (1H, dd, J=5, 10 Hz), 2.6-2.8 (3H, m), 2.85 (1H, dt, J=5, 9 Hz), 3.14 (2H, t, J=7 Hz), 3.61 (2H, t, J=6 Hz), 3.80 (2H, t, J=7 Hz), 4.2-4.4 (1H, m), 7.21 (1H, s), 7.34 (1H, dt, J=1, 7 Hz), 7.38 (1H, dt, J=1, 7 Hz), 7.76 (1H, dd, J=1, 7 Hz), 7.85 (1H, dd, J=1, 7 Hz)

EXAMPLE 39

Production of (3R)-1-{2-[2-(1-benzothiophen-3-yl)ethoxy]ethyl}-3-pyrrolidinol hydrochloride

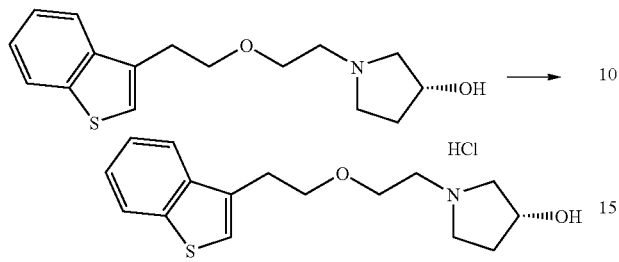

In 5.0 mL of ethyl acetate was dissolved 0.99 g of (3R)-1-{2-[2-(1-benzothiophen-3-yl)ethoxy]ethyl}-3-pyrrolidinol, and to the solution was added 1.10 mL of a 3.25 mol/L dried hydrogen chloride-ethyl acetate solution, after which the resulting mixture was stirred at room temperature for 1 hour. Then, the solvent was distilled off under reduced pressure to obtain 1.05 g of (3R)-1-{2-[2-(1-benzothiophen-3-yl)ethoxy]ethyl}-3-pyrrolidinol hydrochloride as a light-yellow oil.

IR (neat) $cm^{-1}$: 3368, 2946, 1560, 1430, 1121, 765, 734 NMR ($CDCl_3$) δ values: 1.9-2.1 (1H, m), 2.1-2.3 (1H, m), 2.8-3.0 (2H, m), 3.1-3.2 (4H, m), 3.29 (1H, d, J=12 Hz), 3.3-3.5 (1H, m), 3.8-3.9 (4H, m), 4.3-4.4 (1H, m), 7.24 (1H, s), 7.35 (1H, t, J=8 Hz), 7.40 (1H, t, J=8 Hz), 7.76 (1H, d, J=8 Hz), 7.86 (1H, d, J=8 Hz)

EXAMPLE 40

Production of 1-{2-[2-(1-benzothiophen-5-yl)ethoxy]ethyl}-4-piperidinol

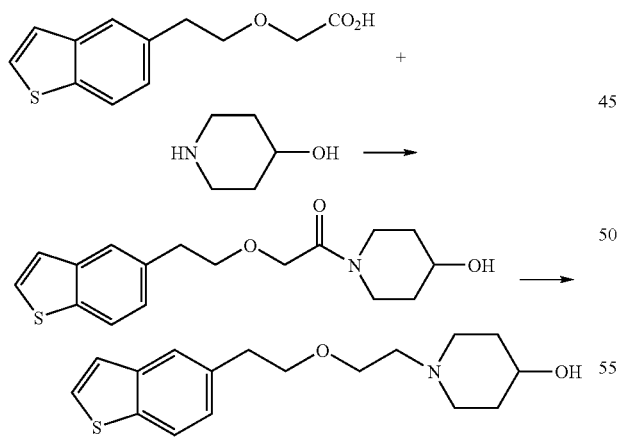

In the same manner as in Example 16 (1), 2-[2-(1-benzothiophen-5-yl)ethoxy]-1-(4-hydroxy-1-piperidinyl)-1-ethanone was obtained as an oil.

Then, 1-{2-[2-(1-benzothiophen-5-yl)ethoxy]ethyl}-4-piperidinol was obtained as a yellow oil in the same manner as in Example 16 (2).

IR (neat) $cm^{-1}$: 3386, 2939, 1110, 1071, 754, 701 NMR ($CDCl_3$) δ values: 1.5-2.3 (6H, m), 2.5-3.0 (2H, m), 2.56 (2H, t, J=6 Hz), 3.00 (2H, t, J=7 Hz), 3.5-3.9 (1H, m), 3.58 (2H, t, J=6 Hz), 3.70 (2H, t, J=7 Hz), 7.19 (1H, d, J=8 Hz), 7.27 (1H, d, J=5 Hz), 7.41 (1H, d, J=5 Hz), 7.65 (1H, s), 7.78 (1H, d, J=8 Hz)

EXAMPLE 41

Production of 1-{2-[2-(1-benzothiophen-5-yl)ethoxy]ethyl}-4-piperidinol hydrochloride

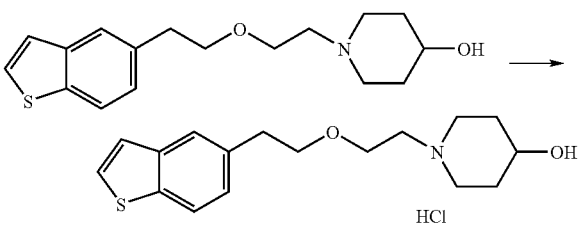

In the same manner as in Example 21, 1-{2-[2-(1-benzothiophen-5-yl)ethoxy]ethyl}-4-piperidinol hydrochloride was obtained as light-brown crystals.

IR (KBr) $cm^{-1}$: 3312, 2946, 2691, 1457, 1124, 1043, 769, 712 NMR ($CDCl_3$) δ values: 1.5-2.5 (4H, m), 2.8-3.2 (6H, m), 2.99 (2H, t, J=6 Hz), 3.76 (2H, t, J=6 Hz), 3.8-4.2 (3H, m), 7.19 (1H, d, J=8 Hz), 7.30 (1H, d, J=5 Hz), 7.44 (1H, d, J=5 Hz), 7.67 (1H, s), 7.80 (1H, d, J=8 Hz)

EXAMPLE 42

Production of 1-{2-[2-(1-benzothiophen-5-yl)ethoxy]ethyl}-3-piperidinol

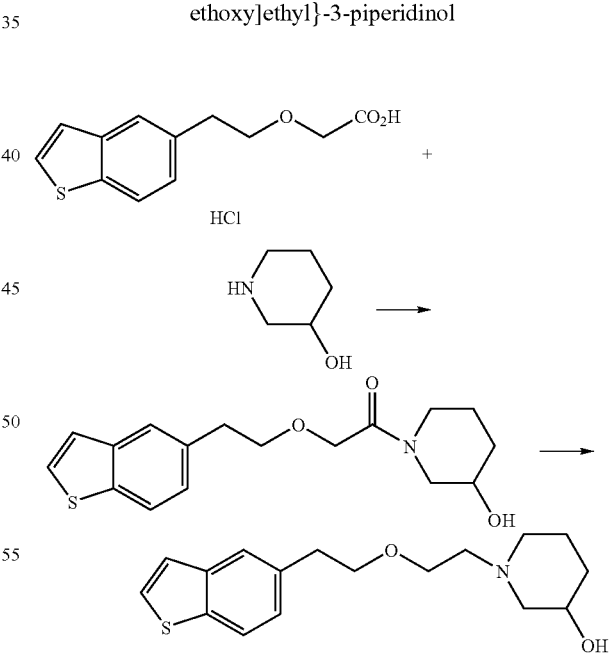

In the same manner as in Example 16 (1), 2-[2-(1-benzothiophen-5-yl)ethoxy]-1-(3-hydroxy-1-piperidinyl)-1-ethanone was obtained as a yellow oil.

IR (neat) $cm^{-1}$: 3408, 2938, 1637, 1114, 704

Then, 1-{2-[2-(1-benzothiophen-5-yl)ethoxy]ethyl}-3-piperidinol was obtained as a yellow oil in the same manner as in Example 16 (2).

IR (neat) cm$^{-1}$: 3387, 2937, 1438, 1109, 703 NMR (CDCl$_3$) δ values: 1.4-2.0 (4H, m), 2.0-2.7 (6H, m), 2.57 (2H, t, J=6 Hz), 3.00 (2H, t, J=7 Hz), 3.56 (2H, t, J=6 Hz), 3.6-3.9 (1H, m), 3.70 (2H, t, J=7 Hz), 7.20 (1H, d, J=8 Hz), 7.28 (1H, d, J=5 Hz), 7.42 (1H, d, J=5 Hz), 7.66 (1H, s), 7.79 (1H, d, J=8 Hz)

EXAMPLE 43

Production of 1-{2-[2-(1-benzothiophen-5-yl)ethoxy]ethyl}-3-piperidinol hydrochloride

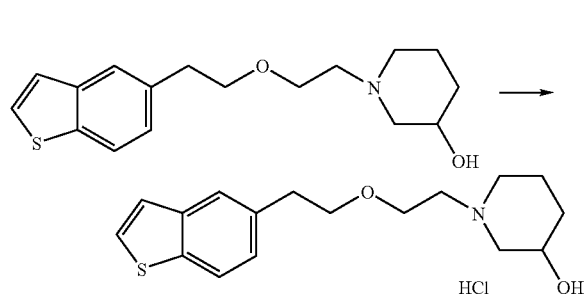

In the same manner as in Example 21, 1-{2-[2-(1-benzothiophen-5-yl)ethoxy]ethyl}-3-piperidinol hydrochloride was obtained as colorless crystals.

IR (KBr) cm$^{-1}$: 3260, 2949, 2638, 1433, 1129, 1045, 702, 668 NMR (CDCl$_3$) δ values: 1.5-2.0 (4H, m), 2.1-2.8 (2H, m), 2.99 (2H, t, J=6 Hz), 3.1-3.6 (4H, m), 3.76 (2H, t, J=6 Hz), 3.8-4.1 (3H, m), 7.20 (1H, d, J=8 Hz), 7.30 (1H, d, J=5 Hz), 7.44 (1H, d, J=5 Hz), 7.67 (1H, s), 7.80 (1H, d, J=8 Hz)

EXAMPLE 44

Production of 1-{2-[2-(1-benzofuran-5-yl)ethoxy]ethyl}-4-piperidinol

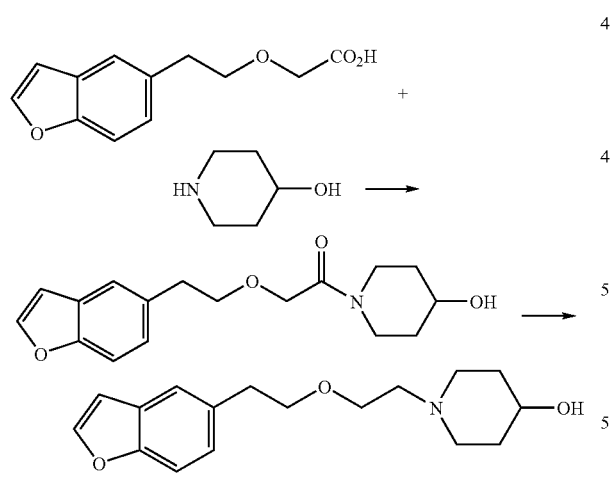

In the same manner as in Example 16 (1), 2-[2-(1-benzofuran-5-yl)ethoxy]-1-(4-hydroxy-1-piperidinyl)-1-ethanone was obtained.

IR (neat) cm$^{-1}$: 3406, 2931, 1636, 1110, 771, 740

Then, 1-{2-[2-(1-benzofuran-5-yl)ethoxy]ethyl}-4-piperidinol was obtained as a colorless oil in the same manner as in Example 16 (2).

IR (neat) cm$^{-1}$: 3359, 2939, 1468, 1111, 1073, 882, 768, 739 NMR (CDCl$_3$) δ values: 1.5-2.3 (6H, m), 2.5-3.0 (2H, m), 2.57 (2H, t, J=6 Hz), 2.97 (2H, t, J=7 Hz), 3.5-3.8 (1H, m), 3.58 (2H, t, J=6 Hz), 3.68 (2H, t, J=7 Hz), 6.71 (1H, dd, J=1, 2 Hz), 7.13 (1H, dd, J=2, 8 Hz), 7.40 (1H, d, J=8 Hz), 7.42 (1H, dd, J=1, 2), 7.55 (1H, d, J=2 Hz)

EXAMPLE 45

Production of 1-{2-[2-(1-benzofuran-5-yl)ethoxy]ethyl}-4-piperidinol hydrochloride

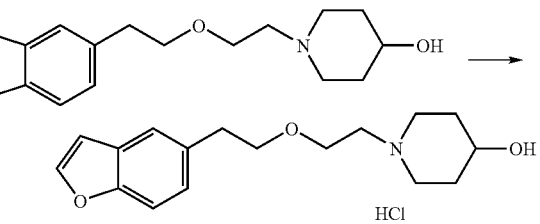

In the same manner as in Example 21, 1-{2-[2-(1-benzofuran-5-yl)ethoxy]ethyl}-4-piperidinol hydrochloride was obtained as a light-yellow oil.

IR (neat) cm$^{-1}$: 3366, 2938, 2638, 1458, 1126, 776, 742 NMR (CDCl$_3$) δ values: 1.6-2.4 (4H, m), 2.8-3.2 (8H, m), 3.71 (2H, t, J=6 Hz), 3.7-4.1 (3H, m), 6.72 (1H, dd, J=1, 2 Hz), 7.12 (1H, dd, J=2, 8 Hz), 7.44 (1H, d, J=8 Hz), 7.42 (1H, dd, J=1, 2), 7.60 (1H, d, J=2 Hz)

EXAMPLE 46

Production of 1-{2-[2-(1-benzofuran-5-yl)ethoxy]ethyl}-3-pyrrolidinol

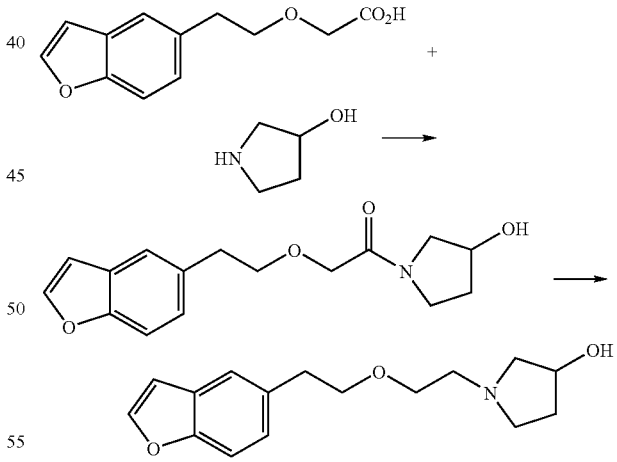

(1) In 13.0 mL of tetrahydrofuran was dissolved 1.28 g of 2-[2-(1-benzofuran-5-yl)ethoxy]acetic acid and the solution was cooled to 5° C., after which 1.41 g of 1,1'-carbonyldiimidazole was added thereto and the resulting mixture was stirred at room temperature for 2 hours. To the reaction mixture were added 1.22 mL of triethylamine and 0.72 mL of 3-pyrrolidinol, followed by stirring at room temperature for 2 hours. Water and ethyl acetate were added to the reaction mixture and the pH was adjusted to 1 with 6 mol/L hydrochloric acid, after which the organic layer was separated. The organic layer was washed with a saturated aqueous sodium hydrogencarbonate solution and then a saturated aqueous sodium chloride solution, and dried over anhydrous magnesium sulfate. Then, the solvent was distilled off under reduced pressure to obtain 1.39 g of 2-[2-(1-benzofuran-5-yl)ethoxy]-1-(3-hydroxy-1-pyrrolidinyl)-1-ethanone as a colorless oil.

IR (neat) cm$^{-1}$: 3398, 2943, 1637, 1467, 1128, 1030, 771, 741

(2) In 14.0 mL of tetrahydrofuran was dissolved 1.39 g of 2-[2-(1-benzofuran-5-yl)ethoxy]-1-(3-hydroxy-1-pyrrolidinyl)-1-ethanone, and 14.4 mL of a 1 mol/L solution of a borane-tetrahydrofuran complex in tetrahydrofuran was added dropwise thereto under ice-cooling, after which the resulting mixture was stirred at room temperature for 17 hours. To the reaction mixture was added 8.0 mL of 6 mol/L hydrochloric acid, and the resulting mixture was heated under reflux for 1 hour. After the reaction mixture was cooled, water and ethyl acetate were added thereto and the pH was adjusted to 10 with a 2 mol/L aqueous sodium hydroxide solution, and then the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=30:1 to 10:1) to obtain 0.96 g of 1-{2-[2-(1-benzofuran-5-yl)ethoxy]ethyl}-3-pyrrolidinol as a colorless oil.

IR (neat) cm$^{-1}$: 3386, 2941, 1468, 1261, 1110, 1030, 882, 769, 738 NMR (CDCl$_3$) δ values: 1.5-2.0 (1H, m), 1.9-3.0 (5H, m), 2.68 (2H, t, J=6 Hz), 2.98 (2H, t, J=7 Hz), 3.58 (2H, t, J=6 Hz), 3.70 (2H, t, J=7 Hz), 4.2-4.4 (1H, m), 6.71 (1H, dd, J=1, 2 Hz), 7.14 (1H, d, J=8 Hz), 7.42 (1H, d, J=8 Hz), 7.4-7.5 (1H, m), 7.59 (1H, d, J=2 Hz)

EXAMPLE 47

Production of 1-{2-[2-(1-benzofuran-5-yl)ethoxy]ethyl}-3-pyrrolidinol oxalate

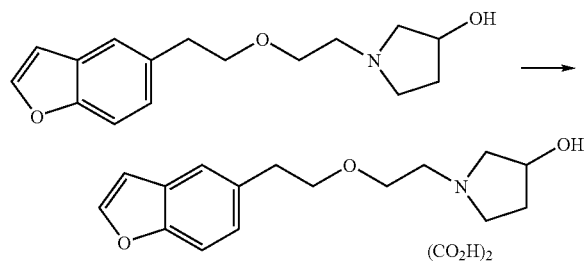

In the same manner as in Example 17, 1-{2-[2-(1-benzofuran-5-yl)ethoxy]ethyl}-3-pyrrolidinol oxalate was obtained as colorless crystals.

IR (KBr) cm$^{-1}$: 3418, 2945, 2698, 1715, 1197, 1111, 720 NMR (DMSO-d$_6$) δ values: 1.6-2.3 (2H, m), 2.92 (2H, t, J=7 Hz), 3.0-3.5 (6H, m), 3.5-3.8 (4H, m), 4.2-4.5 (1H, m), 6.89 (1H, dd, J=1, 2 Hz), 7.19 (1H, dd, J=1, 8 Hz), 7.50 (1H, d, J=8 Hz), 7.5-7.6 (1H, m), 7.94 (1H, d, J=2 Hz)

EXAMPLE 48

Production of (3R*,4R*)-1-{2-[2-(1-benzothiophen-5-yl)ethoxy]ethyl}-3,4-pyrrolidinediol

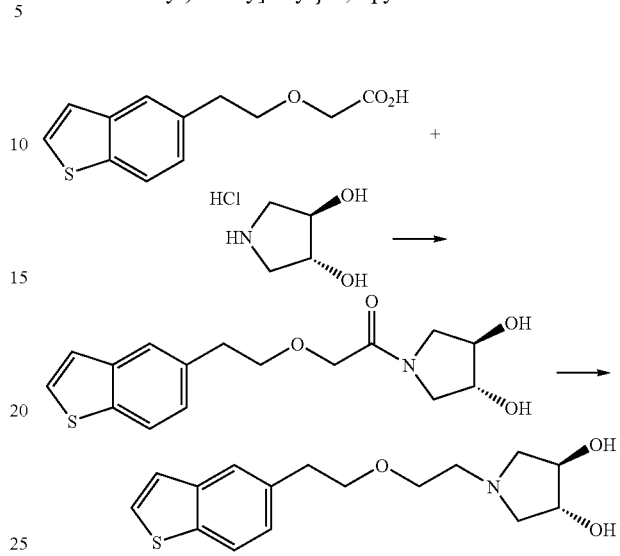

In the same manner as in Example 46 (1), 2-[2-(1-benzothiophen-5-yl)ethoxy]-1-[(3R*,4R*)-3,4-dihydroxy-1-pyrrolidinyl]-1-ethanone was obtained as a yellow oil.

IR (neat) cm$^{-1}$: 3370, 2935, 2874, 1636, 1131, 756, 701

Then, (3R*,4R*)-1-{2-[2-(1-benzothiophen-5-yl)ethoxy]ethyl}-3,4-pyrrolidinediol was obtained as a yellow oil in the same manner as in Example 46 (2).

IR (neat) cm$^{-1}$: 3386, 2938, 2866, 1438, 1113, 756, 703 NMR (CDCl$_3$) δ values: 2.5-3.0 (5H, m), 3.00 (2H, t, J=7 Hz), 3.2-3.7 (1H, m), 3.56 (2H, t, J=6 Hz), 3.71 (2H, t, J=7 Hz), 3.9-4.4 (2H, m), 7.20 (1H, d, J=8 Hz), 7.28 (1H, d, J=5 Hz), 7.43 (1H, d, J=5 Hz), 7.66 (1H, s), 7.80 (1H, d, J=8 Hz)

EXAMPLE 49

Production of (3R*,4R*)-1-{2-[2-(1-benzothiophen-5-yl)ethoxy]ethyl}-3,4-pyrrolidinediol oxalate

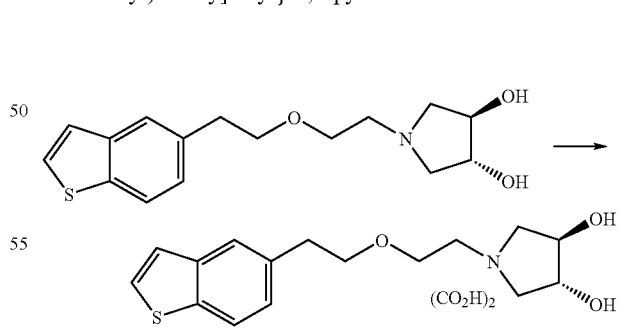

In the same manner as in Example 17, (3R*,4R*)-1-{2-[2-(1-benzothiophen-5-yl)ethoxy]ethyl}-3,4-pyrrolidinediol oxalate was obtained as colorless crystals.

IR (KBr) cm$^{-1}$: 3309, 2929, 1718, 1617, 1199, 1104, 702 NMR (DMSO-d$_6$) δ values: 2.8-3.2 (6H, m), 3.2-3.8 (6H, m), 4.1-4.4 (2H, m), 7.26 (1H, d, J=8 Hz), 7.39 (1H, d, J=5 Hz), 7.72 (1H, d, J=5 Hz), 7.75 (1H, s), 7.90 (1H, d, J=8 Hz)

EXAMPLE 50

Production of 1-{2-[2-(5-methoxy-1-benzofuran-6-yl)ethoxy]ethyl}-3-pyrrolidinol

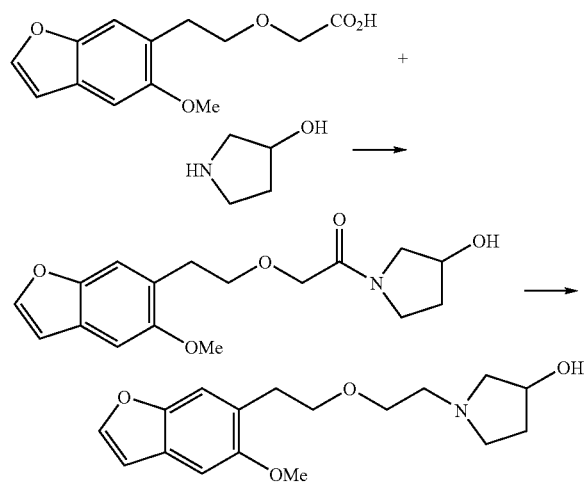

In the same manner as in Example 46 (1), 2-[2-(5-methoxy-1-benzofuran-6-yl)ethoxy]-1-(3-hydroxy-1-pyrrolidinyl)-1-ethanone was obtained as a colorless oil.

IR (neat) cm$^{-1}$: 3394, 2941, 1637, 1465, 1197, 1131, 1015, 841, 759

Then, 1-{2-[2-(5-methoxy-1-benzofuran-6-yl)ethoxy]ethyl}-3-pyrrolidinol was obtained as a colorless oil in the same manner as in Example 46 (2).

IR (neat) cm$^{-1}$: 3386, 2940, 1466, 1430, 1198, 1131, 1015, 837, 762 NMR (CDCl$_3$) δ values: 1.5-2.4 (3H, m), 2.5-3.0 (5H, m), 2.99 (2H, t, J=7 Hz), 3.59 (2H, t, J=6 Hz), 3.67 (2H, t, J=7 Hz), 3.85 (3H, s), 4.2-4.4 (1H, m), 6.68 (1H, d, J=2 Hz), 6.99 (1H, s), 7.34 (1H, s), 7.54 (1H, d, J=2 Hz)

EXAMPLE 51

Production of 1-{2-[2-(5-methoxy-1-benzofuran-6-yl)ethoxy]ethyl}-3-pyrrolidinol oxalate

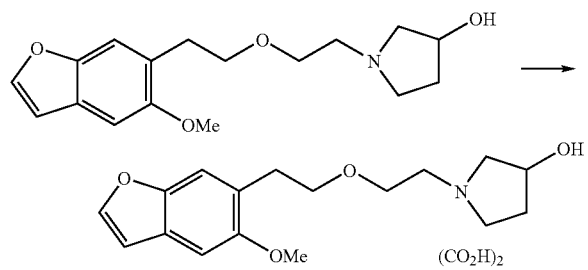

In the same manner as in Example 17, 1-{2-[2-(5-methoxy-1-benzofuran-6-yl)ethoxy]ethyl}-3-pyrrolidinol oxalate was obtained as colorless crystals.

IR (KBr) cm$^{-1}$: 3396, 2942, 2691, 1718, 1636, 1465, 1198, 1130, 720 NMR (DMSO-d$_6$) δ values: 1.7-2.3 (2H, m), 2.8-3.6 (6H, m), 2.91 (2H, t, J=6 Hz), 3.5-3.9 (4H, m), 3.83 (3H, s), 4.2-4.5 (1H, m), 6.86 (1H, d, J=2 Hz), 7.17 (1H, s), 7.43 (1H, s), 7.88 (1H, d, J=2 Hz)

EXAMPLE 52

Production of 1-{2-[2-(6-methoxy-1-benzofuran-5-yl)ethoxy]ethyl}-3-pyrrolidinol

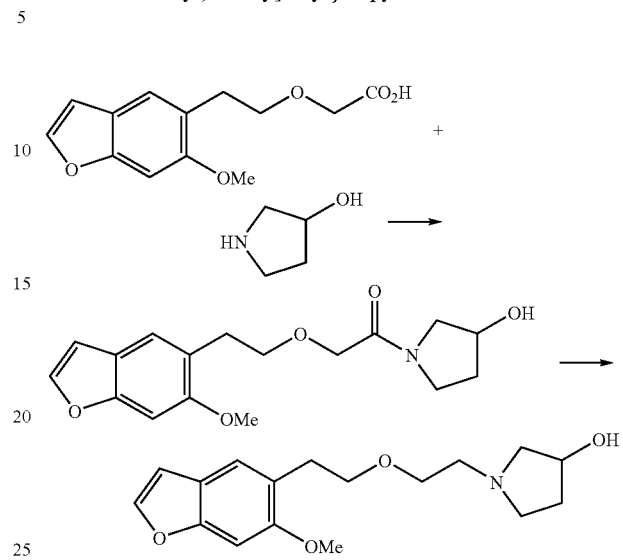

In the same manner as in Example 46 (1), 2-[2-(6-methoxy-1-benzofuran-5-yl)ethoxy]-1-(3-hydroxy-1-pyrrolidinyl)-1-ethanone was obtained as a colorless oil.

IR (neat) cm$^{-1}$: 3381, 2944, 1638, 1475, 1201, 1125, 1011, 758

Then, 1-{2-[2-(6-methoxy-1-benzofuran-5-yl)ethoxy]ethyl}-3-pyrrolidinol was obtained as a colorless oil in the same manner as in Example 46 (2).

IR (neat) cm$^{-1}$: 3398, 2938, 1475, 1202, 1094, 757, 730 NMR (CDCl$_3$) δ values: 1.5-2.4 (3H, m), 2.5-3.0 (5H, m), 2.98 (2H, t, J=7 Hz), 3.59 (2H, t, J=6 Hz), 3.68 (2H, t, J=7 Hz), 3.86 (3H, s), 4.2-4.4 (1H, m), 6.65 (1H, d, J=2 Hz), 7.00 (1H, s), 7.35 (1H, s), 7.50 (1H, d, J=2 Hz)

EXAMPLE 53

Production of 1-{2-[2-(6-methoxy-1-benzofuran-5-yl)ethoxy]ethyl}-3-pyrrolidinol hydrochloride

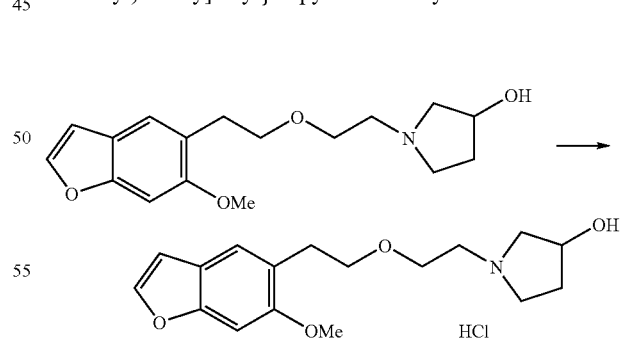

In the same manner as in Example 21, 1-{2-[2-(6-methoxy-1-benzofuran-5-yl)ethoxy]ethyl}-3-pyrrolidinol hydrochloride was obtained as a colorless oil.

IR (neat) cm$^{-1}$: 3377, 2938, 2694, 1475, 1202, 1124, 1093, 1011 NMR (CDCl$_3$) δ values: 1.7-2.2 (2H, m), 2.8-3.6 (6H, m), 2.96 (2H, t, J=6 Hz), 3.5-4.2 (4H, m), 3.86 (3H, s), 4.3-4.6 (1H, m), 6.6-6.7 (1H, m), 7.01 (1H, s), 7.34 (1H, d, J=1 Hz), 7.51 (1H, d, J=2 Hz)

EXAMPLE 54

Production of 1-{2-[2-(1-benzothiophen-5-yl)ethoxy]ethyl}-3-pyrrolidinamine

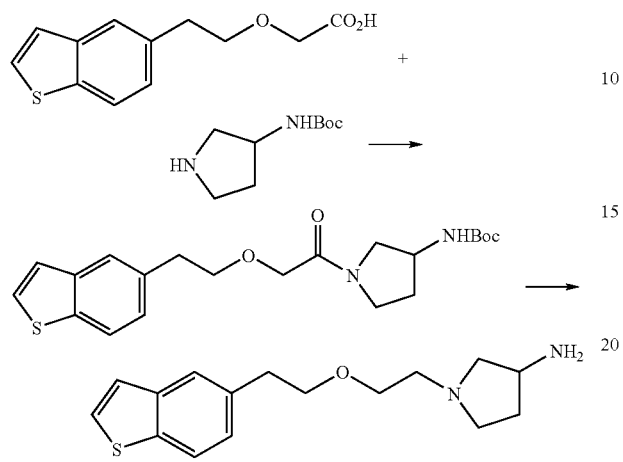

(1) In 10.0 mL of tetrahydrofuran was dissolved 1.00 g of 2-[2-(1-benzothiophen-5-yl)ethoxy]acetic acid, and the solution was cooled to 5° C., after which 1.03 g of 1,1'-carbonyldiimidazole was added thereto and the resulting mixture was stirred at room temperature for 1 hour. After the reaction mixture was cooled to 5° C., 0.88 mL of triethylamine and 1.18 g of tert-butyl=3-pyrrolidinylcarbamate were added thereto, followed by stirring at room temperature for 1 hour. Water and ethyl acetate were added to the reaction mixture and the pH was adjusted to 4 with 6 mol/L hydrochloric acid, after which the organic layer was separated. The organic layer was washed with a saturated aqueous sodium hydrogencarbonate solution and then a saturated aqueous sodium chloride solution, and dried over anhydrous magnesium sulfate. Then, the solvent was distilled off under reduced pressure to obtain 2.00 g of tert-butyl=1-{2-[2-(1-benzothiophen-5-yl)ethoxy]acetyl}-3-pyrrolidinylcarbamate as a light-yellow oil.

(2) In 2.0 mL of tetrahydrofuran was dissolved 2.00 g of the aforesaid tert-butyl=1-{2-[2-(1-benzothiophen-5-yl)ethoxy]acetyl}-3-pyrrolidinyl-carbamate, and the resulting solution was cooled to 5° C., after which 10.6 mL of a 1 mol/L solution of a boranetetrahydrofuran complex in tetrahydrofuran was added dropwise thereto and the resulting mixture was stirred at room temperature for 17 hours. To the reaction mixture was added 3.5 mL of 6 mol/L hydrochloric acid, and the resulting mixture was heated under reflux for 3 hours. After the reaction mixture was cooled, water and ethyl acetate were added thereto and the pH was adjusted to 10 with a 5 mol/L aqueous sodium hydroxide solution, and then the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; chloroform:methanol=30:1 to 15:1) to obtain 1.01 g of 1-{2-[2-(1-benzothiophen-5-yl)ethoxy]ethyl}-3-pyrrolidinamine as a light-yellow oil.

IR (neat) cm$^{-1}$: 3358, 2938, 2861, 1438, 1112, 1052, 755, 703 NMR (CDCl$_3$) δ values: 1.2-1.7 (1H, m), 1.9-3.0 (7H, m), 2.01 (2H, s), 3.00 (2H, t, J=7 Hz), 3.3-3.7 (1H, m), 3.57 (2H, t, J=6 Hz), 3.71 (2H, t, J=7 Hz), 7.20 (1H, d, J=8 Hz), 7.28 (1H, d, J=5 Hz), 7.41 (1H, d, J=5 Hz), 7.66 (1H, s), 7.78 (1H, d, J=8 Hz)

EXAMPLE 55

Production of 1-{2-[2-(1-Benzothiophen-5-yl)ethoxy]ethyl}-3-pyrrolidinamine dioxalate

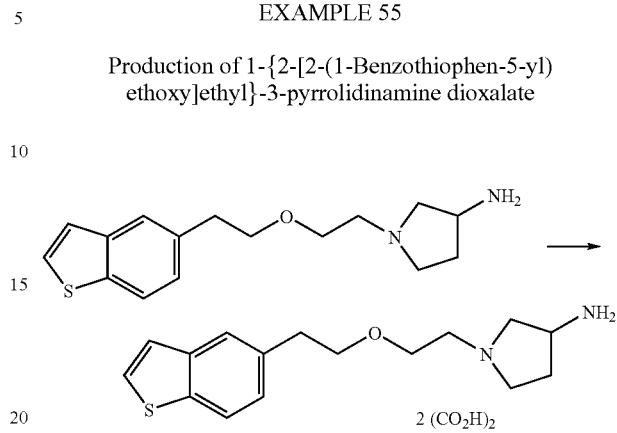

In 3.0 mL of ethyl acetate was dissolved 0.71 g of 1-{2-[2-(1-benzothiophen-5-yl)ethoxy]ethyl}-3-pyrrolidinamine, and to the solution was added a solution of 0.44 g of oxalic acid in 4.0 mL of ethyl acetate. The resulting mixture was stirred at room temperature for 1 hour and then at 5° C. for 1 hour. The crystals precipitated were collected by filtration, washed with ethyl acetate and then dried to obtain 1.03 g of 1-{2-[2-(1-benzothiophen-5-yl)ethoxy]ethyl}-3-pyrrolidinamine dioxalate as colorless crystals.

IR (KBr) cm$^{-1}$: 3447, 2938, 1406, 1279, 1115, 720 NMR (DMSO-d$_6$) δ values: 1.7-2.5 (2H, m), 2.8-3.5 (8H, m), 3.5-4.0 (5H, m), 7.27 (1H, d, J=8 Hz), 7.40 (1H, d, J=5 Hz), 7.72 (1H, d, J=5 Hz), 7.75 (1H, s), 7.90 (1H, d, J=8 Hz)

EXAMPLE 56

Production of 1-{2-[2-(1-benzofuran-5-yl)ethoxy]ethyl}-3-pyrrolidinamine

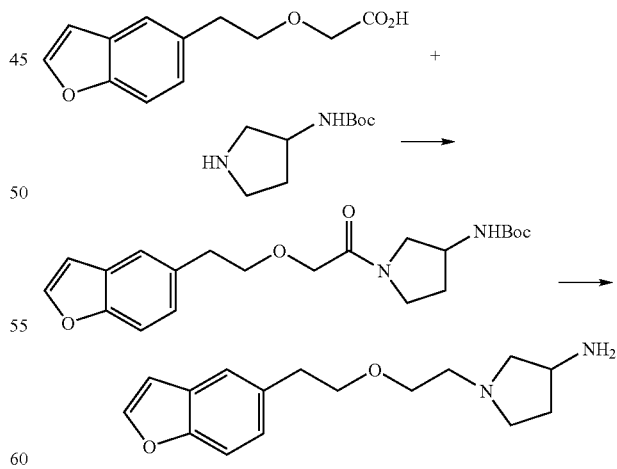

In the same manner as in Example 54 (1), tert-butyl=1-{2-[2-(1-benzofuran-5-yl)ethoxy]acetyl}-3-pyrrolidinylcarbamate was obtained.

Then, 1-{2-[2-(1-benzofuran-5-yl)ethoxy]ethyl}-3-pyrrolidinamine was obtained as a yellow oil in the same manner as in Example 54 (2).

IR (neat) cm$^{-1}$: 3356, 2938, 1467, 1261, 1111, 1030, 882, 769, 740 NMR (CDCl$_3$) δ values: 1.2-1.7 (1H, m), 2.02 (2H, s), 2.1-3.0 (7H, m), 2.98 (2H, t, J=7 Hz), 3.3-3.7 (1H, m), 3.57 (2H, t, J=6 Hz), 3.69 (2H, t, J=7 Hz), 6.71 (1H, dd, J=1, 2 Hz), 7.15 (1H, dd, J=1, 7 Hz), 7.40 (1H, d, J=7 Hz), 7.4-7.5 (1H, m), 7.59 (1H, d, J=2 Hz)

EXAMPLE 57

Production of 1-{2-[2-(1-benzofuran-5-yl)ethoxy]ethyl}-3-pyrrolidinamine oxalate

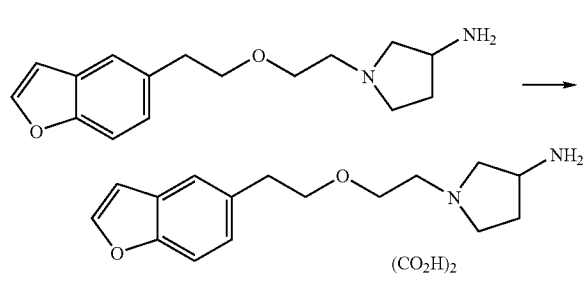

In the same manner as in Example 17, 1-{2-[2-(1-benzofuran-5-yl)ethoxy]ethyl}-3-pyrrolidinamine oxalate was obtained as colorless crystals.

IR (KBr) cm$^{-1}$: 3408, 2952, 1615, 1311, 1127, 769 NMR (DMSO-d$_6$) δ values: 1.5-1.9 (1H, m), 1.8-2.4 (1H, m), 2.1-3.0 (6H, m), 2.89 (2H, t, J=7 Hz), 3.4-3.8 (5H, m), 6.89 (1H, dd, J=1, 2 Hz), 7.18 (1H, d, J=8 Hz), 7.50 (1H, d, J=8 Hz), 7.4-7.6 (1H, m), 7.94 (1H, d, J=2 Hz)

EXAMPLE 58

Production of 1-{3-[2-(1-benzothiophen-5-yl)ethoxy]propyl}-3-pyrrolidinol

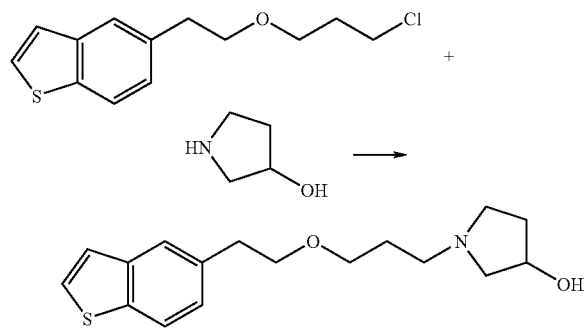

In 12 mL of N,N-dimethylformamide was dissolved 1.20 g of 5-[2-(3-chloropropoxy)ethyl]-1-benzothiophene, and 0.82 g of 3-pyrrolidinol and 1.30 g of potassium carbonate were added to the solution, after which the resulting mixture was stirred at 85° C. for 2.5 hours. After the reaction mixture was cooled, water and ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform : methanol 20:1 to 10:1) to obtain 0.78 g of 1-{3-[2-(1-benzothiophen-5-yl)ethoxy]propyl}-3-pyrrolidinol as a colorless oil.

IR (neat) cm$^{-1}$: 3386, 2943, 1438, 1106, 1052, 755, 701 NMR (CDCl$_3$) δ values: 1.5-2.0 (3H, m), 2.0-3.0 (7H, m), 2.98 (2H, t, J=7 Hz), 3.49 (2H, t, J=6 Hz), 3.67 (2H, t, J=7 Hz), 4.2-4.4 (1H, m), 7.1-7.3 (2H, m), 7.41 (1H, d, J=6 Hz), 7.66 (1H, s), 7.78 (1H, d, J=8 Hz)

EXAMPLE 59

Production of 1-{3-[2-(1-benzothiophen-5-yl)ethoxy]propyl}-3-pyrrolidinol hydrochloride

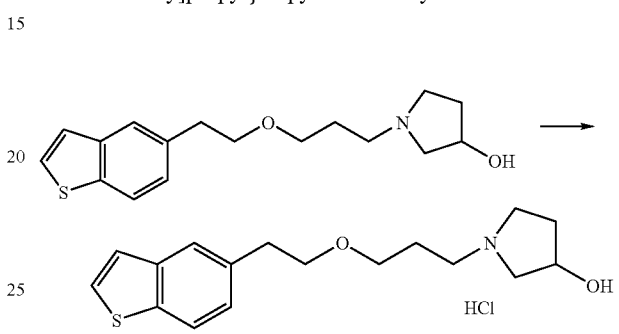

In the same manner as in Example 21, 1-{3-[2-(1-benzothiophen-5-yl)ethoxy]propyl}-3-pyrrolidinol hydrochloride was obtained as colorless crystals.

IR (KBr) cm$^{-1}$: 3368, 2937, 2695, 1438, 1108, 821, 764, 708 NMR (CDCl$_3$) δ values: 1.8-2.3 (4H, m), 2.3-3.6 (6H, m), 2.96 (2H, t, J=6 Hz), 3.50 (2H, t, J=6 Hz), 3.68 (2H, t, J=7 Hz), 4.3-4.7 (1H, m), 7.21 (1H, d, J=8 Hz), 7.30 (1H, d, J=5 Hz), 7.43 (1H, d, J=5 Hz), 7.67 (1H, s), 7.80 (1H, d, J=8 Hz)

EXAMPLE 60

Production of 1-{3-[2-(1-benzofuran-5-yl)ethoxy]propyl}-3-pyrrolidinol

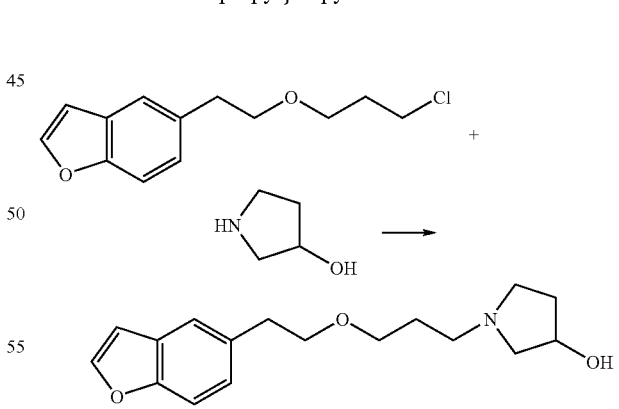

In the same manner as in Example 58, 1-{3-[2-(1-benzofuran-5-yl)ethoxy]propyl}-3-pyrrolidinol was obtained as a light-yellow oil.

IR (neat) cm$^{-1}$: 3386, 2942, 1467, 1261, 1108, 1030, 883, 740 NMR (CDCl$_3$) δ values: 1.5-2.0 (3H, m), 2.0-3.0 (7H, m), 2.95 (2H, t, J=7 Hz), 3.49 (2H, t, J=6 Hz), 3.65 (2H, t, J=7 Hz), 4.2-4.4 (1H, m), 6.71 (1H, dd, J=1, 2 Hz), 7.14 (1H, dd, J=1, 8 Hz), 7.3-7.5 (2H, m), 7.58 (1H, d, J=2 Hz)

EXAMPLE 61

Production of 1-{3-[2-(1-benzofuran-5-yl)ethoxy]propyl}-3-pyrrolidinol hydrochloride

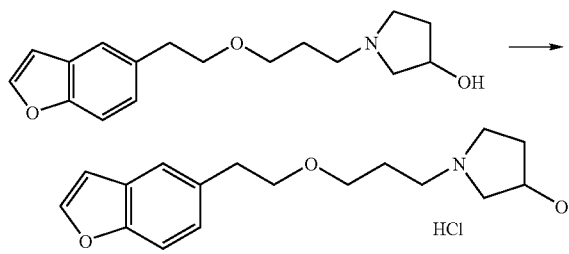

In the same manner as in Example 39, 1-{3-[2-(1-benzofuran-5-yl)ethoxy]propyl}-3-pyrrolidinol hydrochloride was obtained as a light-yellow oil.

IR (neat) cm$^{-1}$: 3339, 2941, 2605, 1468, 1262, 1110, 773, 742 NMR (CDCl$_3$) δ values: 1.6-2.4 (4H, m), 2.4-4.0 (12H, m), 4.4-4.8 (1H, m), 6.72 (1H, d, J=2 Hz), 7.12 (1H, d, J=8 Hz), 7.3-7.6 (2H, m), 7.59 (1H, d, J=2 Hz)

EXAMPLE 62

Production of 1-{3-[2-(6-fluoro-1-benzothiophen-5-yl)ethoxy]propyl}-3-pyrrolidinol

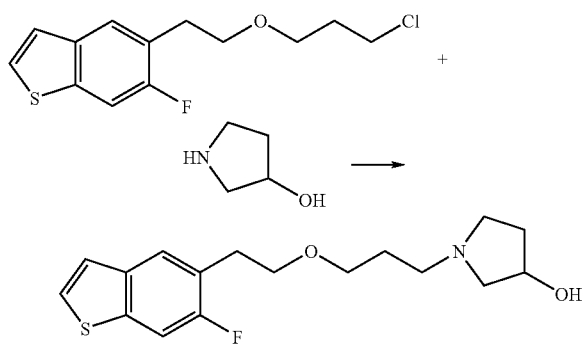

In the same manner as in Example 58, 1-{3-[2-(6-fluoro-1-benzothiophen-5-yl)ethoxy]propyl}-3-pyrrolidinol was obtained as a yellow oil.

IR (neat) cm$^{-1}$: 3422, 2952, 1458, 1257, 1106, 838, 747, 711 NMR (CDCl$_3$) δ values: 1.5-3.0 (10H, m), 3.00 (2H, t, J=7 Hz), 3.4-3.6 (2H, m), 3.68 (2H, t, J=7 Hz), 4.2-4.4 (1H, m), 7.23 (1H, d, J=5 Hz), 7.36 (1H, d, J=5 Hz), 7.51 (1H, d, J=10 Hz), 7.66 (1H, d, J=7 Hz)

EXAMPLE 63

Production of 1-{3-[2-(6-fluoro-1-benzothiophen-5-yl)ethoxy]propyl}-3-pyrrolidinol hydrochloride

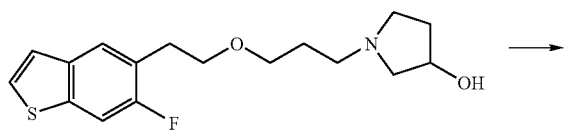

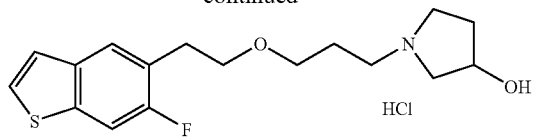

In the same manner as in Example 39, 1-{3-[2-(6-fluoro-1-benzothiophen-5-yl)ethoxy]propyl}-3-pyrrolidinol hydrochloride was obtained as a yellow oil.

IR (neat) cm$^{-1}$: 3377, 2954, 2702, 1458, 1257, 1107, 750, 712 NMR (CDCl$_3$) δ values: 1.8-2.3 (4H, m), 2.8-3.6 (8H, m), 3.53 (2H, t, J=6 Hz), 3.69 (2H, t, J=7 Hz), 4.3-4.4 (1H, m), 7.27 (1H, d, J=5 Hz), 7.39 (1H, d, J=5 Hz), 7.52 (1H, d, J=10 Hz), 7.67 (1H, d, J=7 Hz)

EXAMPLE 64

Production of (3R, 4S)-1-{3-[2-(1-benzothiophen-5-yl)ethoxy]propyl}-3,4-pyrrolidinediol

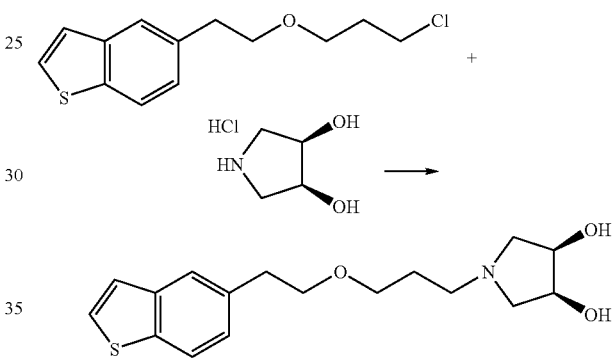

In the same manner as in Example 58, (3R, 4S)-1-{3-[2-(1-benzothiophen-5-yl)ethoxy]propyl}-3,4-pyrrolidinediol was obtained as a colorless oil.

IR (neat) cm$^{-1}$: 3387, 2940, 1438, 1159, 1108, 1051, 703 NMR (CDCl$_3$) δ values: 1.5-1.9 (2H, m), 2.4-2.8 (6H, m), 2.98 (2H, t, J=7 Hz), 3.47 (2H, t, J=6 Hz), 3.67 (2H, t, J=7 Hz), 4.1-4.3 (2H, m), 7.20 (1H, dd, J=1, 8 Hz), 7.27 (1H, d, J=5 Hz), 7.42 (1H, d, J=5 Hz), 7.65 (1H, d, J=1 Hz), 7.79 (1H, d, J=8 Hz)

EXAMPLE 65

Production of (3R, 4S)-1-{3-[2-(1-benzothiophen-5-yl)ethoxy]propyl}-3,4-pyrrolidinediol hydrochloride

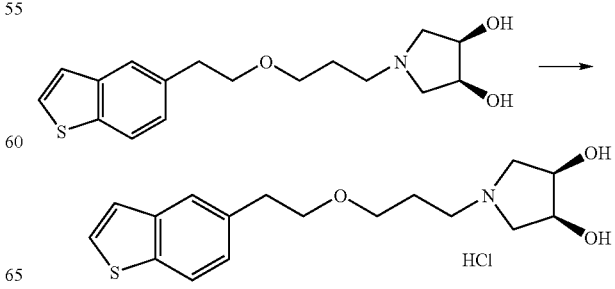

In the same manner as in Example 21, (3R, 4S)-1-{3-[2-(1-benzothiophen-5-yl)ethoxy]propyl}-3,4-pyrrolidinediol hydrochloride was obtained as colorless crystals.

IR (KBr) cm$^{-1}$: 3381, 2871, 2602, 1120, 808, 768, 718 NMR (DMSO-d$_6$) δ values: 1.8-2.0 (2H, m), 2.8-3.8 (12H, m), 3.9-4.3 (2H, m), 7.25 (1H, dd, J=2, 8 Hz), 7.39 (1H, d, J=5 Hz), 7.72 (1H, d, J=5 Hz), 7.73 (1H, d, J=2 Hz), 7.90 (1H, d, J=8 Hz)

EXAMPLE 66

Production of 1-{3-[2-(1-benzothiophen-5-yl)ethoxy]propyl}-4-piperidinol

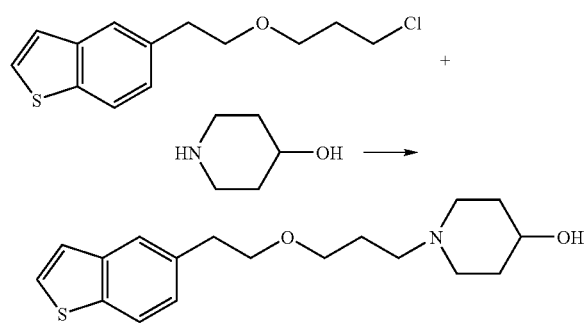

In the same manner as in Example 58, 1-{3-[2-(1-benzothiophen-5-yl)ethoxy]propyl}-4-piperidinol was obtained as a light-yellow oil.

IR (neat) cm$^{-1}$: 3385, 2935, 1438, 1364, 1111, 755, 701 NMR (CDCl$_3$) δ values: 1.4-2.2 (8H, m), 2.1-2.5 (2H, m), 2.5-3.0 (2H, m), 2.98 (2H, t, J=7 Hz), 3.48 (2H, t, J=6 Hz), 3.5-3.8 (1H, m), 3.67 (2H, t, J=7 Hz), 7.1-7.3 (2H, m), 7.42 (1H, d, J=5 Hz), 7.66 (1H, s), 7.79 (1H, d, J=8 Hz)

EXAMPLE 67

Production of 1-{3-[2-(1-benzothiophen-5-yl)ethoxy]propyl}-4-piperidinol oxalate

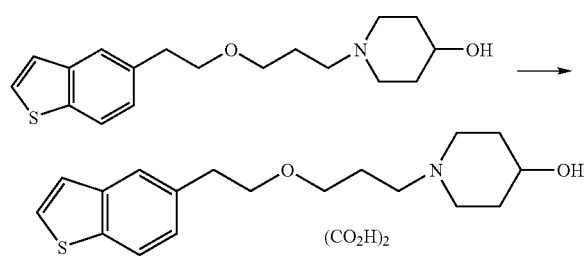

In the same manner as in Example 17, 1-{3-[2-(1-benzothiophen-5-yl)ethoxy]propyl}-4-piperidinol oxalate was obtained as colorless crystals.

IR (KBr) cm$^{-1}$: 3420, 2866, 1718, 1616, 1190, 1120, 705 NMR (DMSO-d$_6$) δ values: 1.5-2.0 (6H, m), 2.8-3.1 (8H, m), 3.4-3.8 (1H, m), 3.44 (2H, t, J=6 Hz), 3.64 (2H, t, J=6 Hz), 7.24 (1H, d, J=8 Hz), 7.40 (1H, d, J=5 Hz), 7.6-7.8 (2H, m), 7.91 (1H, d, J=8 Hz)

EXAMPLE 68

Production of 1-{2-[2-(2-naphthyl)ethoxy]ethyl}-3-pyrrolidinol

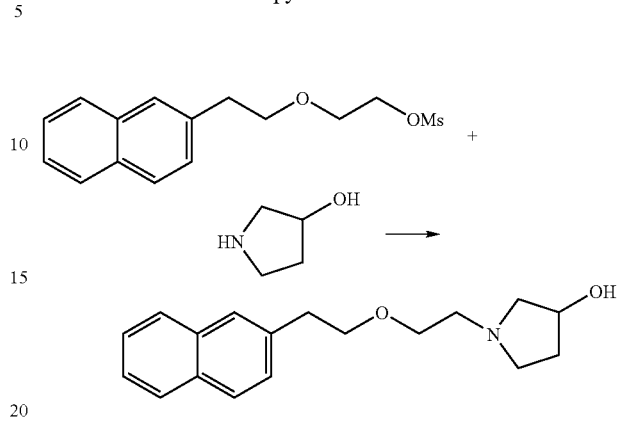

In 8 mL of N,N-dimethylformamide was dissolved 0.80 g of 2-[2-(2-naphthyl)ethoxy]-ethyl=methanesulfonate, and 0.45 mL of 3-pyrrolidinol and 0.75 g of potassium carbonate were added to the solution, after which the resulting mixture was stirred at 90° C. for 2 hours. After the reaction mixture was cooled, water and ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=8:1 to 5:1) to obtain 0.51 g of 1-{2-[2-(2-naphthyl)ethoxy]ethyl}-3-pyrrolidinol as a colorless oil.

IR (neat) cm$^{-1}$: 3422, 2938, 1112, 820, 749 NMR (CDCl$_3$) δ values: 1.5-1.9 (1H, m), 2.0-2.5 (3H, m), 2.5-3.0 (4H, m), 3.05 (2H, t, J=7 Hz), 3.59 (2H, t, J=6 Hz), 3.75 (2H, t, J=7 Hz), 4.2-4.4 (1H, m), 7.2-7.6 (4H, m), 7.6-8.0 (3H, m)

EXAMPLE 69

Production of 1-{2-[2-(2-naphthyl)ethoxy]ethyl}-3-pyrrolidinol oxalate

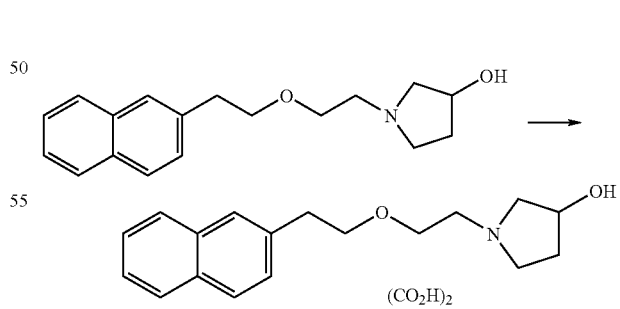

In the same manner as in Example 17, 1-{2-[2-(2-naphthyl)ethoxy]ethyl}-3-pyrrolidinol oxalate was obtained as colorless crystals.

IR (KBr) cm$^{-1}$: 3366, 2945, 1405, 1113, 820, 720 NMR (DMSO-d$_6$) δ values: 1.6-2.3 (2H, m), 2.7-3.5 (8H, m), 3.5-3.9 (4H, m), 4.2-4.5 (1H, m), 7.4-7.6 (3H, m), 7.7-8.0 (4H, m)

EXAMPLE 70

Production of (3R, 4S)-1-{2-[2-(1-benzothiophen-5-yl)ethoxy]ethyl}-3,4-pyrrolidinediol

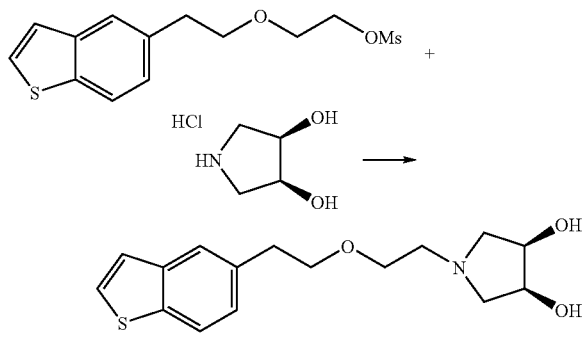

In 25 mL of N,N-dimethylformamide was dissolved 2.50 g of 2-[2-(1-benzothiophen-5-yl)ethoxy]ethyl=methanesulfonate, and 1.40 g of (3R, 4S)-3,4-pyrrolidinediol hydrochloride and 4.70 mL of triethylamine were added to the solution, after which the resulting mixture was stirred at 90° C. for 1 hour. After the reaction mixture was cooled, water and ethyl acetate were added thereto and the pH was adjusted to 10 with a 2 mol/L aqueous sodium hydroxide solution, and the organic layer was separated. The organic layer was washed with water and then a saturated aqueous sodium chloride solution, and dried over anhydrous magnesium sulfate. The solvent was distilled off under reduced pressure and the residue was purified by a column chromatography (eluent; chloroform:methanol=8:1 to 5:1) to obtain 0.84 g of (3R, 4S)-1-{2-[2-(1-benzothiophen-5-yl)ethoxy]ethyl}-3,4-pyrrolidinediol as a yellow oil.

IR (neat) cm$^{-1}$: 3390, 2940, 1438, 1111, 1050, 703 NMR (CDCl$_3$) δ values: 2.5-3.0 (6H, m), 3.00 (2H, t, J=7 Hz), 3.55 (2H, t, J=6 Hz), 3.70 (2H, t, J=7 Hz), 4.0-4.3 (2H, m), 7.21 (1H, dd, J=1, 8 Hz), 7.28 (1H, d, J=5 Hz), 7.43 (1H, d, J=5 Hz), 7.66 (1H, d, J=1 Hz), 7.80 (1H, d, J=8 Hz)

EXAMPLE 71

Production of (3R, 4S)-1-{2-[2-(1-benzothiophen-5-yl)ethoxy]ethyl}-3,4-pyrrolidinediol hydrochloride

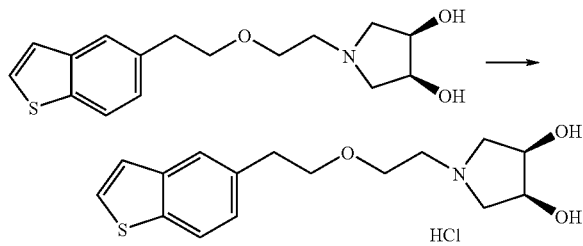

In the same manner as in Example 21, (3R, 4S)-1-{2-[2-(1-benzothiophen-5-yl)ethoxy]ethyl}-3,4-pyrrolidinediol hydrochloride was obtained as colorless crystals.

IR (KBr) cm$^{-1}$: 3194, 2854, 1365, 1348, 1130, 1111, 820, 712 NMR (DMSO-d$_6$) δ values: 2.8-4.0 (12H, m), 3.9-4.3 (2H, m), 7.2-7.5 (2H, m), 7.7-8.2 (3H, m)

EXAMPLE 72

Production of Tert-butyl=1-{3-[2-(1-benzothiophen-5-yl)ethoxy]propyl}-3-pyrrolidinylcarbamate

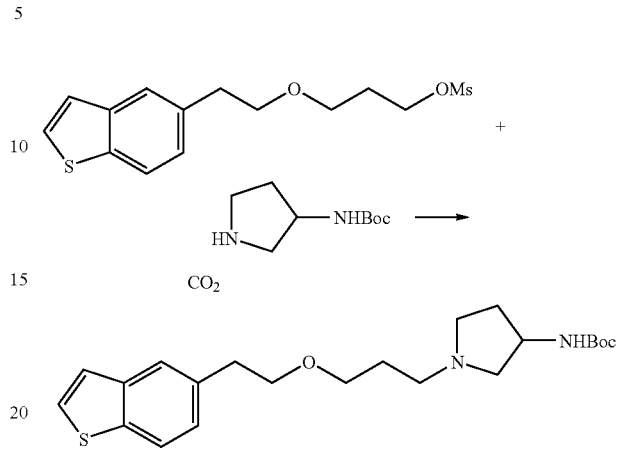

In 7 mL of N,N-dimethylformamide was dissolved 0.70 g of 3-[2-(1-benzothiophen-5-yl)ethoxy]propyl=methanesulfonate, and 1.03 g of tert-butyl=3-pyrrolidinylcarbamate carbonate and 1.86 mL of triethylamine were added to the solution, after which the resulting mixture was stirred at 90° C. for 2 hours. After the reaction mixture was cooled, water and ethyl acetate were added thereto and the pH was adjusted to 10 with 6 mol/L hydrochloric acid, and the organic layer was separated. The organic layer was washed with water and then a saturated aqueous sodium chloride solution, and dried over anhydrous magnesium sulfate. Subsequently, the solvent was distilled off under reduced pressure to obtain 1.12 g of tert-butyl=1-{3-[2-(1-benzothiophen-5-yl)ethoxy]propyl}-3-pyrrolidinylcarbamate as a yellow oil.

NMR (CDCl$_3$) δ values: 1.2-1.9 (3H, m), 1.44 (9H, s), 1.9-3.0 (7H, m), 2.99 (2H, t, J=7 Hz), 3.49 (2H, t, J=6 Hz), 3.67 (2H, t, J=7 Hz), 4.0-4.3 (1H, m), 7.19 (1H, d, J=8 Hz), 7.27 (1H, d, J=5 Hz), 7.42 (1H, d, J=5 Hz), 7.66 (1H, s), 7.79 (1H, d, J=8 Hz)

EXAMPLE 73

Production of 1-{3-[2-(1-benzothiophen-5-yl)ethoxy]propyl}-3-pyrrolidinamine

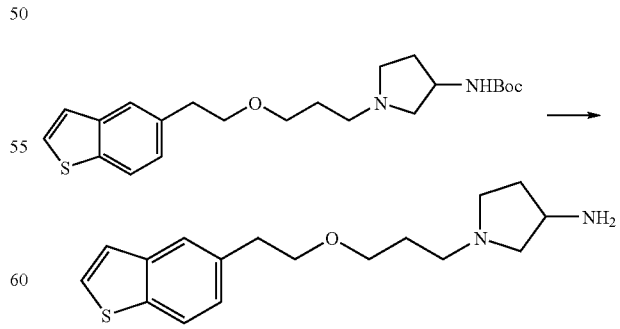

In 7.0 mL of ethyl acetate was dissolved 1.12 g of tert-butyl=1-{3-[2-(1-benzothiophen-5-yl)ethoxy]propyl}-3-pyrrolidinylcarbamate, and 1.86 mL of 6 mol/L hydrochloric acid was added to the solution, after which the resulting mixture was heated under reflux for 1 hour. After the reaction mixture was cooled, water and ethyl acetate were added thereto and the pH was adjusted to 10 with a 2 mol/L aqueous sodium hydroxide solution, and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=30:1 to 20:1) to obtain 0.38 g of 1-{3-[2-(1-benzothiophen-5-yl)ethoxy]propyl}-3-pyrrolidinamine as a light-yellow oil.

IR (neat) cm$^{-1}$: 3357, 2937, 2861, 2796, 1146, 1108, 755, 701 NMR (CDCl$_3$) δ values: 1.2-1.9 (4H, m), 1.9-2.8 (7H, m), 2.97 (2H, t, J=7 Hz), 3.48 (2H, t, J=6 Hz), 3.66 (2H, t, J=7 Hz), 7.19 (1H, d, J=8 Hz), 7.23 (1H, d, J=5 Hz), 7.39 (1H, d, J=5 Hz), 7.64 (1H, s), 7.77 (1H, d, J=8 Hz)

EXAMPLE 74

Production of 1-{3-[2-(1-benzothiophen-5-yl)ethoxy]propyl}-3-pyrrolidinamine oxalate

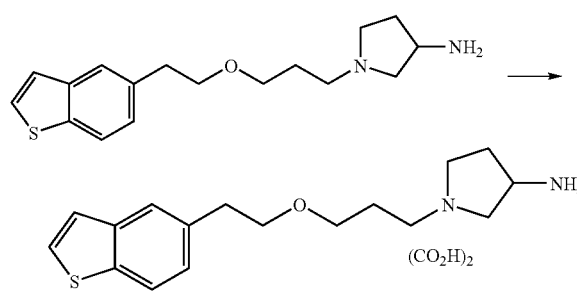

In the same manner as in Example 17, 1-{3-[2-(1-benzothiophen-5-yl)ethoxy]propyl}-3-pyrrolidinamine oxalate was obtained as colorless crystals.

IR (KBr) cm$^{-1}$: 3390, 2871, 1614, 1310, 1122, 766 NMR (DMSO-d$_6$) δ values: 1.5-1.9 (2H, m), 1.9-2.9 (8H, m), 2.92 (2H, t, J=7 Hz), 3.3-3.7 (1H, m), 3.43 (2H, t, J=6 Hz), 3.62 (2H, t, J=7 Hz), 7.25 (1H, d, J=8 Hz), 7.39 (1H, d, J=5 Hz), 7.72 (1H, d, J=5 Hz), 7.73 (1H, s), 7.90 (1H, d, J=8 Hz)

EXAMPLE 75

Production of N-(1-{3-[2-(1-benzothiophen-5-yl)ethoxy]propyl}-3-pyrrolidinyl)acetamide

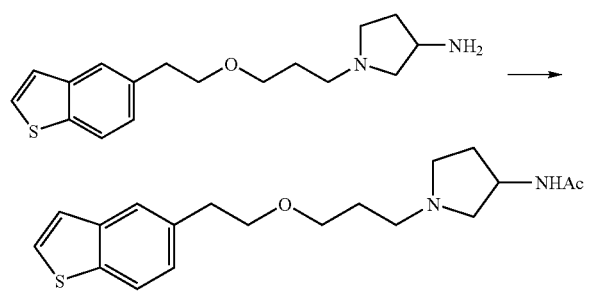

In 5 mL of methylene chloride was dissolved 0.50 g of 1-{3-[2-(1-benzothiophen-5-yl)ethoxy]propyl}-3-pyrrolidinamine, and the solution was cooled to −60° C., after which 0.27 mL of triethylamine and 0.14 mL of acetyl chloride were added to the solution and the resulting mixture was stirred at room temperature for 1 hour. Water and ethyl acetate were added to the reaction mixture and the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; chloroform:methanol=50:1 to 10:1) to obtain 0.55 g of N-(1-{3-[2-(1-benzothiophen-5-yl)ethoxy]propyl}-3-pyrrolidinyl)acetamide as a yellow oil.

IR (neat) cm$^{-1}$: 3292, 2946, 1654, 1560, 1110, 757, 702 NMR (CDCl$_3$) δ values: 1.5-1.7 (1H, m), 1.7-1.8 (2H, m), 1.94 (3H, s), 2.13 (1H, q, J=9 Hz), 2.2-2.3 (1H, m), 2.4-2.5 (3H, m), 2.59 (1H, dd, J=2, 10 Hz), 2.86 (1H, dt, J=4, 9 Hz), 2.99 (2H, t, J=7 Hz), 3.49 (2H, t, J=6 Hz), 3.67 (2H, t, J=7 Hz), 4.3-4.5 (1H, m), 5.8-5.9 (1H, m), 7.22 (1H, dd, J=1, 8 Hz), 7.28 (1H, d, J=5 Hz), 7.42 (1H, d, J=5 Hz), 7.67 (1H, d, J=1 Hz), 7.79 (1H, d, J=8 Hz)

EXAMPLE 76

Production of N-(1-{3-[2-(1-benzothiophen-5-yl)ethoxy]propyl}-3-pyrrolidinyl)acetamide hydrochloride

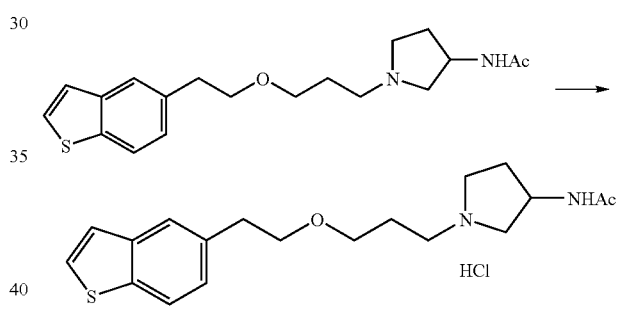

In the same manner as in Example 21, N-(1-{3-[2-(1-benzothiophen-5-yl)ethoxy]propyl}-3-pyrrolidinyl)acetamide hydrochloride was obtained as light-brown crystals.

IR (KBr) cm$^{-1}$: 3422, 2868, 2475, 1664, 1542, 1343, 1117, 711 NMR (CDCl$_3$) δ values: 1.9-2.1 (3H, m), 2.05 (3H, s), 2.3-2.4 (1H, m), 2.4-2.5 (1H, m), 2.6-2.7 (1H, m), 2.8-2.9 (2H, m), 2.97 (2H, t, J=6 Hz), 3.4-3.4 (1H, m), 3.51 (2H, t, J=6 Hz), 3.6-3.7 (1H, m), 3.70 (2H, t, J=6 Hz), 4.6-4.8 (1H, m), 7.22 (1H, dd, J=1, 8 Hz), 7.31 (1H, d, J=5 Hz), 7.46 (1H, d, J=5 Hz), 7.67 (1H, s), 7.81 (1H, d, J=8 Hz)

EXAMPLE 77

Production of N-(1-{3-[2-(1-benzothiophen-5-yl)ethoxy]propyl}-3-pyrrolidinyl)methanesulfonamide

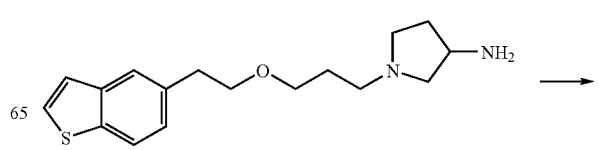

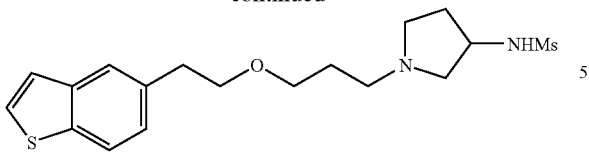

In the same manner as in Example 75, N-(1-{3-[2-(1-benzothiophen-5-yl)ethoxy]propyl}-3-pyrrolidinyl)methanesulfonamide was obtained as a yellow oil.

IR (neat) cm$^{-1}$: 3270, 2927, 2856, 1320, 1148, 1110, 756 NMR (CDCl$_3$) δ values: 1.6-1.8 (3H, m), 2.1-2.3 (2H, m), 2.44 (2H, t, J=7 Hz), 2.50 (1H, dd, J=6, 10 Hz), 2.60 (1H, dd, J=3, 10 Hz), 2.77 (1H, dt, J=4, 9 Hz), 2.94 (3H, s), 2.99 (2H, t, J=7 Hz), 3.48 (2H, t, J=6 Hz), 3.68 (2H, t, J=7 Hz), 3.9-4.0 (1H, m), 4.6-4.8 (1H, m), 7.22 (1H, dd, J=1, 8 Hz), 7.28 (1H, d, J=5 Hz), 7.42 (1H, d, J=5 Hz), 7.67 (1H, d, J=1 Hz), 7.79 (1H, d, J=8 Hz)

EXAMPLE 78

Production of N-(1-{3-[2-(1-benzothiophen-5-yl)ethoxy]propyl}-3-pyrrolidinyl)methanesulfonamide oxalate

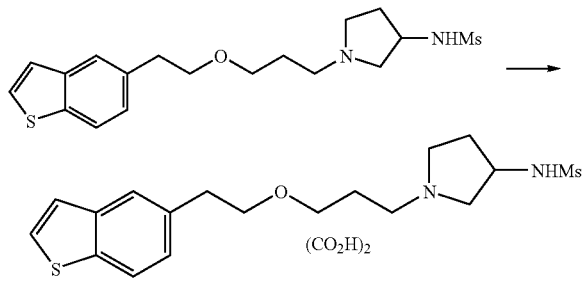

In the same manner as in Example 17, N-(1-{3-[2-(1-benzothiophen-5-yl)ethoxy]propyl}-3-pyrrolidinyl)methanesulfonamide oxalate was obtained as colorless crystals.

IR (KBr) cm$^{-1}$: 3250, 2868, 1718, 1314, 1165, 1119, 707 NMR (DMSO-d$_6$) δ values: 1.8-2.0 (3H, m), 2.2-2.3 (1H, m), 2.93 (2H, t, J=7 Hz), 2.97 (3H, s), 3.0-3.1 (3H, m), 3.1-3.2 (1H, m), 3.2-3.3 (1H, m), 3.4-3.5 (1H, m), 3.45 (2H, t, J=6 Hz), 3.63 (2H, t, J=7 Hz), 4.0-4.1 (1H, m), 7.26 (1H, dd, J=1, 8 Hz), 7.40 (1H, d, J=5 Hz), 7.4-7.6 (1H, m), 7.72 (1H, d, J=5 Hz), 7.74 (1H, d, J=1 Hz), 7.90 (1H, d, J=8 Hz)

EXAMPLE 79

Production of 1-{3-[2-(1-benzothiophen-5-yl)ethoxy]propyl}-N,N-dimethyl-3-pyrrolidinamine

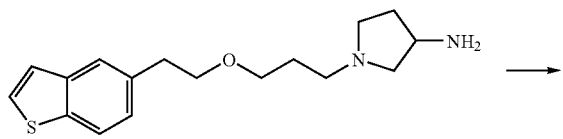

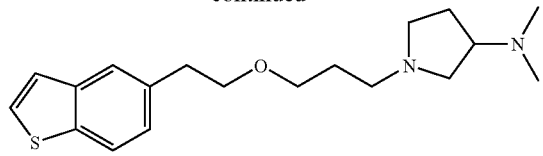

In 8.6 mL of methanol was dissolved 0.43 g of 1-{3-[2-(1-benzothiophen-5-yl)ethoxy]propyl}-3-pyrrolidinamine, and the solution was cooled to 5° C., after which 0.35 mL of 37% formalin and 0.09 g of sodium borohydride were added to the solution and the resulting mixture was stirred at room temperature for 17 hours. Under ice-cooling, 2.6 mL of 2 mol/L hydrochloric acid was added to the reaction mixture, followed by stirring at room temperature for 30 minutes, after which water and ethyl acetate were added thereto and the aqueous layer was separated. Ethyl acetate was added to the aqueous layer and the pH was adjusted to 9.5 with a 2 mol/L aqueous sodium hydroxide solution, after which the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; chloroform:methanol=50:1 to 10:1) to obtain 0.39 g of 1-{3-[2-(1-benzothiophen-5-yl)ethoxy]propyl}-N,N-dimethyl-3-pyrrolidinamine as a yellow oil.

IR (neat) cm$^{-1}$: 2945, 2862, 2786, 1458, 1111, 700 NMR (CDCl$_3$) δ values: 1.6-1.8 (3H, m), 1.9-2.0 (1H, m), 2.20 (6H, s), 2.2-2.3 (1H, m), 2.3-2.5 (2H, m), 2.50 (1H, dt, J=8, 12 Hz), 2.7-2.8 (2H, m), 2.8-2.9 (1H, m), 2.99 (2H, t, J=7 Hz), 3.49 (2H, t, J=7 Hz), 3.67 (2H, t, J=7 Hz), 7.22 (1H, dd, J=1, 8 Hz), 7.28 (1H, d, J=5 Hz), 7.41 (1H, d, J=5 Hz), 7.67 (1H, d, J=1 Hz), 7.79 (1H, d, J=8 Hz)

EXAMPLE 80

Production of 1-{3-[2-(1-benzothiophen-5-yl)ethoxy]propyl}-N,N-dimethyl-3-pyrrolidinamine dihydrochloride

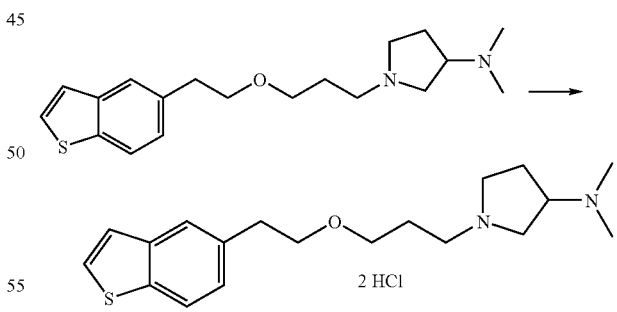

In 4.0 mL of ethyl acetate was dissolved 0.39 g of 1-{3-[2-(1-benzothiophen-5-yl)ethoxy]propyl}-N,N-dimethyl-3-pyrrolidinamine, and to the solution was added 0.80 mL of a 3.25 mol/L dried hydrogen chloride-ethyl acetate solution. The resulting mixture was stirred at room temperature for 1 hour and then at 5° C. for 1 hour. The crystals precipitated were collected by filtration, washed with ethyl acetate and then dried to obtain 0.32 g of 1-{3-[2-(1-benzothiophen-5-yl)ethoxy]propyl}-N,N-dimethyl-3-pyrrolidinamine dihydrochloride as colorless crystals.

IR (KBr) cm$^{-1}$: 2936, 1437, 1101, 701 NMR (CDCl$_3$) δ values: 1.9-2.1 (2H, m), 2.4-2.6 (2H, m), 2.84 (6H, s), 2.98 (2H, t, J=7 Hz), 3.1-3.2 (2H, m), 3.4-3.9 (4H, m), 3.54 (2H, t, J=5 Hz), 3.72 (2H, dt, J=3, 7 Hz), 4.2-4.3 (1H, m), 7.24 (1H, d, J=8 Hz), 7.35 (1H, d, J=5 Hz), 7.43 (1H, d, J=5 Hz), 7.71 (1H, s), 7.84 (1H, d, J=8 Hz)

EXAMPLE 81

Production of 1-{3-[2-(1-benzothiophen-5-yl)ethoxy]propyl}-3-azetidinol 1/2 fumarate

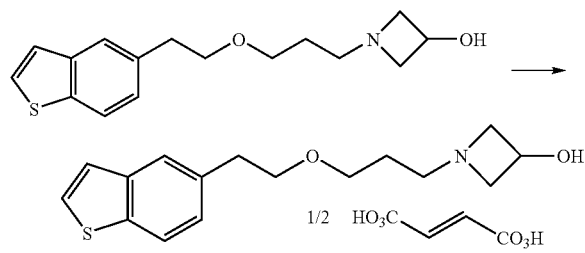

In 10.0 mL of ethanol was dissolved 5.00 g of 1-{3-[2-(1-benzothiophen-5-yl)ethoxy]propyl}-3-azetidinol, and the solution was heated at 70° C., after which 0.99 g of fumaric acid was added to the solution 10 and stirred for 30 minutes. To the resulting solution was added dropwise 30.0 mL of ethyl acetate, and the resulting mixture was stirred at 60° C. for 15 minutes, cooled to 5° C. over a period of 1 hour and then stirred at the same temperature for 1 hour. The crystals precipitated were collected by filtration, washed with ethyl acetate and then dried to obtain 5.83 g of 1-{3-[2-(1-benzothiophen-5-yl)ethoxy]propyl}-3-azetidinol 1/2 fumarate as colorless crystals.

IR (KBr) cm$^{-1}$: 3258, 2936, 2862, 1578, 1360, 1114, 1109, 707, 665 NMR (DMSO-d$_6$) δ values: 1.5-1.6 (2H, m), 2.60 (2H, t, J=7 Hz), 2.91 (2H, t, J=7 Hz), 2.9-3.1 (2H, m), 3.39 (2H, t, J=7 Hz), 3.60 (2H, t, J=7 Hz), 3.6-3.8 (2H, m), 4.1-4.3 (1H, m), 6.50 (1H, s), 7.25 (1H, dd, J=1, 8 Hz), 7.39 (1H, d, J=5 Hz), 7.72 (1H, d, J=5 Hz), 7.73 (1H, d, J=1 Hz), 7.89 (1H, d, J=8 Hz)

EXAMPLE 82

Production of 1-{3-[2-(1-benzothiophen-5-yl)ethoxy]propyl}-3-azetidinol

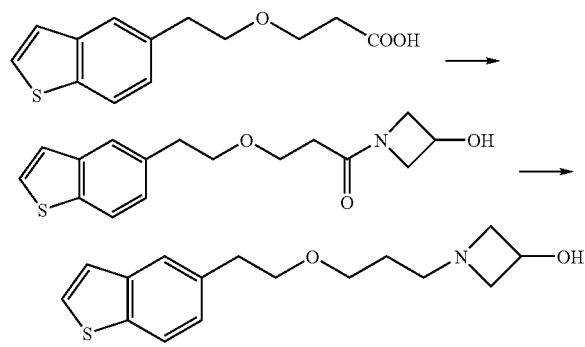

(1) In 12.5 mL of toluene was suspended 5.00 g of 3-[2-(1-benzothiophen-5-yl)ethoxy]propionic acid, and 0.1 mL of N,N-dimethylformamide was added thereto, after which 1.68 mL of thionyl chloride was added dropwise thereto at 15° C. and the resulting mixture was stirred at room temperature for 1 hour. The reaction mixture was added dropwise to a solution of 4.44 g of 3-hydroxyazetidine 1/2 tartrate and 3.76 g of sodium hydroxide in 25 mL of water at 10° C., and stirred at room temperature for 1 hour. Ethyl acetate was added to the reaction mixture and the organic layer was separated. The organic layer was washed with diluted hydrochloric acid and then a saturated aqueous sodium chloride solution, dried over anhydrous magnesium sulfate, and then distilled under reduced pressure to remove the solvent. The residue was purified by a column chromatography (eluent; chloroform: acetone=3:1 to 1:1) and crystallized from diisopropyl ether to obtain 5.48 g of 3-[2-(1-benzothiophen-5-yl)ethoxy]-1-(3-hydroxy-1-azetidinyl)-1-propanone as colorless crystals.

IR (KBr) cm$^{-1}$: 3316, 2875, 1610, 1481, 1112, 992, 706 NMR (CDCl$_3$) δ values: 2.2-2.4 (2H, m), 2.98 (2H, t, J=7 Hz), 3.6-3.8 (5H, m), 3.8-4.0 (1H, m), 4.1-4.3 (2H, m), 4.4-4.4 (1H, m), 7.20 (1H, dd, J=1, 8 Hz), 7.28 (1H, dd, J=1, 5 Hz), 7.41 (1H, d, J=5 Hz), 7.6-7.7 (1H, m), 7.79 (1H, d, J=8 Hz)

(2) In 20 mL of tetrahydrofuran was dissolved 5.00 g of 3-[2-(1-benzothiophen-5-yl)ethoxy]-1-(3-hydroxy-1-azetidinyl)-1-propanone, and 1.09 g of sodium borohydride was added thereto, after which 4.25 mL of a boron trifluoride-tetrahydrofuran complex was added dropwise thereto at 10° C. and the resulting mixture was stirred at the same temperature for 1 hour and then at 40° C. for 3 hours. After the reaction mixture was cooled to 10° C., 30 mL of 6 mol/L hydrochloric acid was added dropwise thereto and the resulting mixture was refluxed for 1 hour. After cooling, the solvent was concentrated under reduced pressure, and ethyl acetate was added. The pH was adjusted to 9.4 with a 20% aqueous sodium hydroxide solution and then the organic layer was separated. The organic layer was washed with water and then a saturated aqueous sodium chloride solution, dried over anhydrous magnesium sulfate, and then distilled under reduced pressure to remove the solvent. The resulting residue was purified by a column chromatography (eluent; chloroform:methanol=20:1 to 10:1) and crystallized from toluene-diisopropyl ether (1:3, 14 mL) to obtain 2.31 g of 1-{3-[2-(1-benzothiophen-5-yl)ethoxy]propyl}-3-azetidinol.

EXAMPLE 83

Production of 1-{3-[2-(1-benzothiophen-5-yl)ethoxy]propyl}-3-azetidinol maleate

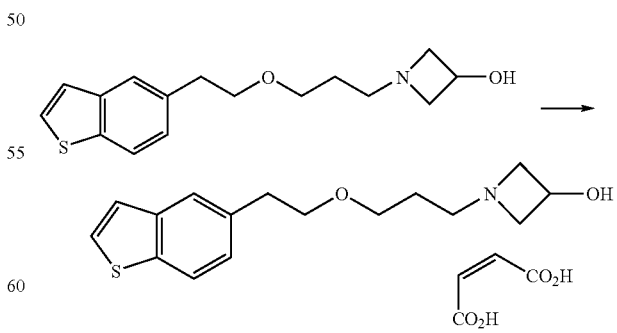

In 56 mL of acetone was dissolved 8.00 g of 1-{3-[2-(1-benzothiophen-5-yl)ethoxy]propyl}-3-azetidinol, followed by adding thereto 3.19 g of maleic acid, and the resulting mixture was heated at 60° C. to effect dissolution. The reaction mixture was slowly cooled and then stirred at 5° C. for 30 minutes. The crystals precipitated were collected by filtration to obtain 9.89 g of 1-{3-[2-(1-benzothiophen-5-yl)ethoxy]propyl}-3-azetidinol maleate as colorless crystals.

NMR (DMSO-$d_6$) δ values: 1.6-1.8 (2H, m), 2.93 (2H, t, J=7 Hz), 3.13 (2H, t, J=7 Hz), 3.43 (2H, t, J=6 Hz), 3.63 (2H, t, J=7 Hz), 3.7-3.9 (2H, m), 4.1-4.3 (2H, m), 4.4-4.5 (1H, m), 6.04 (2H, s), 7.26 (1H, dd, J=1, 8 Hz), 7.40 (1H, d, J=5 Hz), 7.7-7.8 (1H, m), 7.74 (1H, d, J=5 Hz), 7.92 (1H, d, J=8 Hz)

EXAMPLE 84

Production of 1-{3-[2-(1-benzothiophen-5-yl)ethoxy]propyl}-3-azetidinol nitrate

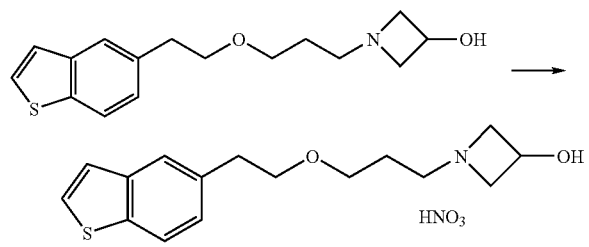

In 20 mL of ethyl acetate was dissolved 10.0 g of 1-{3-[2-(1-benzothiophen-5-yl)ethoxy]propyl}-3-azetidinol, and 20 mL of isopropanol was added thereto, after which 2.60 mL of concentrated nitric acid (61%) was added dropwise thereto at room temperature. To the reaction mixture was added dropwise 60 mL of ethyl acetate, and the resulting mixture was stirred at the same temperature for 1 hour and then at 5° C. for 1 hour. The crystals precipitated were collected by filtration to obtain 11.3 g of 1-{3-[2-(1-benzothiophen-5-yl)ethoxy]propyl}-3-azetidinol nitrate as colorless crystals.

IR (KBr) cm$^{-1}$: 3354, 2880, 1385, 1107, 712 NMR (DMSO-$d_6$) δ values: 1.6-1.8 (2H, m), 2.93 (2H, t, J=7 Hz), 3.1-3.2 (2H, m), 3.44 (2H, t, J=6 Hz), 3.64 (2H, t, J=7 Hz), 3.7-3.9 (2H, m), 4.0-4.4 (2H, m), 4.4-4.5 (1H, m), 7.27 (1H, d, J=8 Hz), 7.41 (1H, d, J=5 Hz), 7.74 (1H, d, J=5 Hz), 7.74 (1H, s), 7.92 (1H, d, J=8 Hz)

EXAMPLE 85

Production of 1-{3-[2-(1-benzothiophen-5-yl)ethoxy]propyl}-3-azetidinol L-tartrate

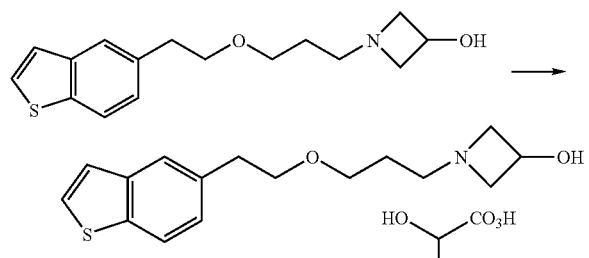

In 40 mL of ethyl acetate was dissolved 10.0 g of 1-{3-[2-(1-benzothiophen-5-yl)ethoxy]propyl}-3-azetidinol, and 5.15 g of L-tartaric acid and 40 mL of ethanol were added thereto, after which the resulting mixture was heated at 65° C. to effect dissolution. After the resulting solution was stirred at 50° C. for 20 minutes, 40 mL of ethyl acetate was added dropwise thereto at the same temperature and the resulting mixture was stirred at 20 to 30° C. for 1 hour. The crystals precipitated were collected by filtration to obtain 13.9 g of 1-{3-[2-(1-benzothiophen-5-yl)ethoxy]propyl}-3-azetidinol L-tartrate as colorless crystals.

IR (KBr) cm$^{-1}$: 3318, 2807, 1305, 1126, 679, 483 NMR (DMSO-$d_6$) δ values: 1.5-1.7 (2H, m), 2.82 (2H, t, J=7 Hz), 2.92 (2H, t, J=7 Hz), 3.2-3.4 (2H, m), 3.41 (2H, t, J=6 Hz), 3.61 (2H, t, J=7 Hz), 3.8-4.0 (2H, m), 4.02 (2H, s), 4.2-4.4 (1H, m), 7.26 (1H, dd, J=2, 8 Hz), 7.40 (1H, d, J=5 Hz), 7.73 (1H, d, J=5 Hz), 7.7-7.8 (1H, m), 7.91 (1H, d, J=5 Hz)

EXAMPLE 86

Production of 1-{3-[2-(1-benzothiophen-5-yl)ethoxy]propyl}-3-azetidinol 1/2 succinate

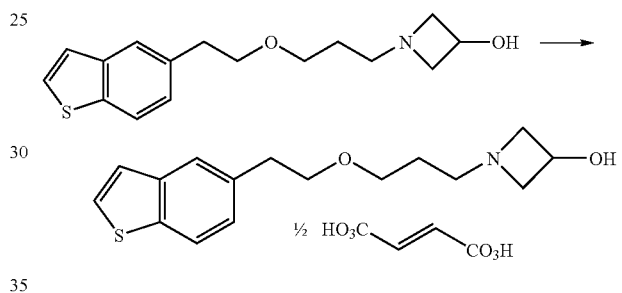

In 30 mL of ethyl acetate was dissolved 10.0 g of 1-{3-[2-(1-benzothiophen-5-yl)ethoxy]propyl}-3-azetidinol, and 2.03 g of succinic acid and 35 mL of isopropanol were added thereto, after which the resulting mixture was refluxed to effect dissolution. After 40 mL of ethyl acetate was added dropwise to the reaction mixture, the resulting mixture was slowly cooled and then stirred at 5° C. for 30 minutes. The crystals precipitated were collected by filtration to obtain 11.1 g of 1-{3-[2-(1-benzothiophen-5-yl)ethoxy]propyl}-3-azetidinol 1/2 succinate as colorless crystals.

IR (KBr) cm$^{-1}$: 3250, 2936, 1576, 1361, 1109, 707, 652 NMR (DMSO-$d_6$) δ values: 1.4-1.6 (2H, m), 2.35 (2H, s), 2.46 (2H, t, J=7 Hz), 2.7-2.9 (2H, m), 2.91 (2H, t, J=7 Hz), 3.38 (2H, t, J=6 Hz), 3.5-3.6 (2H, m), 3.59 (2H, t, J=7 Hz), 4.1-4.2 (1H, m), 7.25 (1H, dd, J=2, 8 Hz), 7.39 (1H, d, J=5 Hz), 7.72 (1H, d, J=5 Hz), 7.7-7.8 (1H, m), 7.90 (1H, d, J=8 Hz)

EXAMPLE 87

Production of 1-{3-[2-(1-benzothiophen-5-yl)ethoxy]propyl}-3-azetidinol citrate

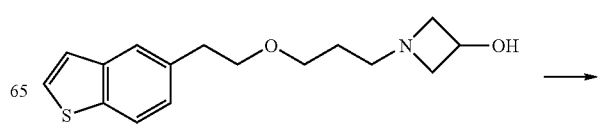

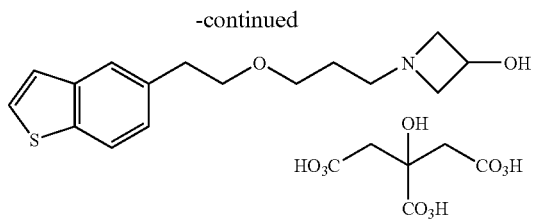

In 14.4 mL of ethanol was dissolved 10.0 g of 1-{3-[2-(1-benzothiophen-5-yl)ethoxy]propyl}-3-azetidinol, followed by adding thereto 7.21 g of citric acid monohydrate, and the resulting mixture was heated at 50° C. to effect dissolution. To the resulting solution were added 35 mL of ethyl acetate and 5.6 mL of ethanol at 50° C., and stirred at 25° C. The reaction mixture was heated at 40° C., after which ethyl acetate (45 mL) was added dropwise thereto and the resulting mixture was stirred at 40° C. for 10 minutes and then at 10 to 20° C. for 1 hour. The crystals precipitated were collected by filtration to obtain 14.9 g of 1-{3-[2-(1-benzothiophen-5-yl)ethoxy]propyl}-3-azetidinol citrate as colorless crystals.

IR (KBr) cm$^{-1}$: 3374, 2943, 1720, 1224, 1104, 706 NMR (DMSO-d$_6$) δ values: 1.6-1.7 (2H, m), 2.50 (2H, d, J=15 Hz), 2.58 (2H, d, J=15 Hz), 93 (2H, t, J=7 Hz), 2.99 (2H, t, J=7 Hz), 3.42 (2H, t, J=6 Hz), 3.5-3.6 (2H, m), 3.63 (2H, t, J=7 Hz), 4.0-4.1 (2H, m), 4.3-4.4 (1H, m), 7.26 (1H, d, J=8 Hz), 7.40 (1H, d, J=5 Hz), 7.73 (1H, d, J=5 Hz), 7.7-7.8 (1H, m), 7.91 (1H, d, J=8 Hz)

EXAMPLE 88

Production of 1-{3-[2-(1-benzothiophen-5-yl)ethoxy]propyl}-3-azetidinyl=benzoate

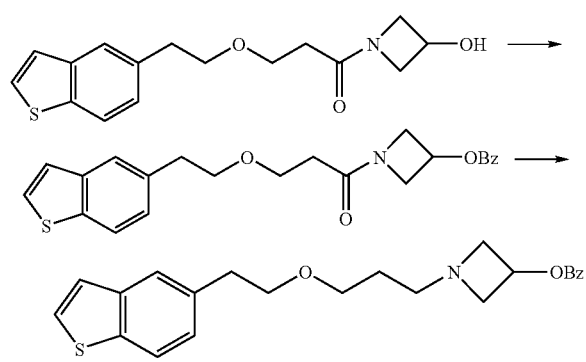

(1) In 7 mL of methylene chloride was dissolved 0.70 g of 3-[2-(1-benzothiophen-5-yl)ethoxy]-1-(3-hydroxy-1-azetidinyl)-1-propanone, and 0.57 mL of triethylamine was added to the solution. After the resulting mixture was cooled to 5° C., 0.42 mL of benzoyl chloride was added thereto, followed by stirring at the same temperature for 1 hour. Water was added to the reaction mixture and the pH was adjusted to 1 with 2 mol/L hydrochloric acid, after which the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; toluene:ethyl acetate=5:1 to 2:1) to obtain 0.45 g of 1-{3-[2-(1-benzothiophen-5-yl)ethoxy]propanoyl}-3-azetidinyl=benzoate as a colorless oil.

IR (neat) cm$^{-1}$: 2873, 1719, 1654, 1451, 1274, 1117, 714 NMR (CDCl$_3$) δ values: 2.3-2.4 (2H, m), 2.99 (2H, t, J=7 Hz), 3.72 (2H, t, J=7 Hz), 3.7-3.8 (2H, m), 4.0-4.3 (2H, m), 4.3-4.4 (1H, m), 4.4-4.6 (1H, m), 5.2-5.4 (1H, m), 7.1-7.3 (2H, m), 7.41 (1H, d, J=5 Hz), 7.46 (2H, t, J=8 Hz), 7.5-7.7 (2H, m), 7.78 (1H, d, J=8 Hz), 8. 0-8.1 (2H, m)

(2) In 1 mL of tetrahydrofuran was dissolved 0.51 g of 1-{3-[2-(1-benzothiophen-5-yl)ethoxy]propanoyl}-3-azetidinyl=benzoate, and 6.8 mL of a 1 mol/L solution of a borane-tetrahydrofuran complex in tetrahydrofuran was added dropwise thereto under ice-cooling, after which the resulting mixture was stirred at room temperature for 22 hours. To the reaction mixture was added 6.2 mL of ethanol, and the resulting mixture was refluxed for 4 hours. After cooling, the solvent was distilled off under reduced pressure and water and ethyl acetate were added to the residue, and the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; toluene:ethyl acetate=5:1–chloroform) to obtain 0.33 g of 1-{3-[2-(1-benzothiophen-5-yl)ethoxy]propyl}-3-azetidinyl=benzoate as a colorless oil.

IR (neat) cm$^{-1}$: 2941, 1718, 1274, 1115, 755, 713 NMR (CDCl$_3$) δ values: 1.6-1.7 (2H, m), 2.54 (2H, t, J=7 Hz), 3.00 (2H, t, J=7 Hz), 3.0-3.2 (2H, m), 3.49 (2H, t, J=6 Hz), 3.67 (2H, t, J=7 Hz), 3.7-3.8 (2H, m), 5.2-5.3 (1H, m), 7.22 (1H, dd, J=2, 8 Hz), 7.28 (1H, d, J=5 Hz), 7.40 (1H, d, J=5 Hz), 7.45 (2H, t, J=8 Hz), 7.5-7.6 (1H, m), 7.6-7.7 (1H, m), 7.79 (1H, d, J=8 Hz), 8.0-8.1 (2H, m)

EXAMPLE 89

Production of 1-{3-[2-(1-benzothiophen-5-yl)ethoxy]propyl}-3-azetidinyl=benzoate maleate

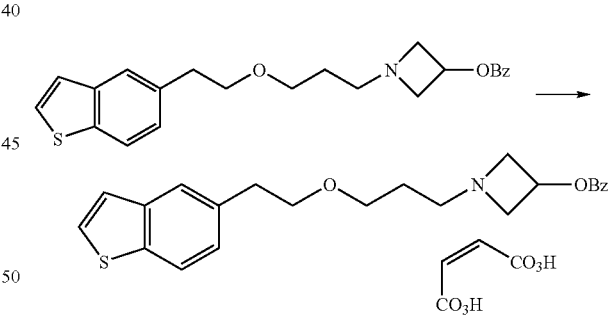

In 3 mL of ethyl acetate was dissolved 0.25 g 5 of 1-{3-[2-(1-benzothiophen-5-yl)ethoxy]propyl}-3-azetidinyl=benzoate, and 0.07 g of maleic acid was added thereto, after which the resulting mixture was heated to effect dissolution. The reaction mixture was cooled and the crystals precipitated were collected by filtration to obtain 0.15 g of 1-{3-[2-(1-benzothiophen-5-yl)ethoxy]propyl}-3-azetidinyl=benzoate maleate.

IR (KBr) cm$^{-1}$: 2872, 1732, 1454, 1358, 1270, 1119 NMR (DMSO-d$_6$) δ values: 1.6-1.8 (2H, m), 2.94 (2H, t, J=7 Hz), 3.1-3.3 (2H, m), 3.46 (2H, t, J=6 Hz), 3.65 (2H, t, J=7 Hz), 4.1-4.3 (2H, m), 4.4-4.6 (2H, m), 5.3-5.5 (1H, m), 6.04 (2H, s), 7.26 (1H, d, J=8 Hz), 7.39 (1H, d, J=5 Hz), 7.58 (2H, t, J=8 Hz), 7.7-7.8 (3H, m), 7.91 (1H, d, J=8 Hz), 8.0-8.1 (2H, m)

EXAMPLE 90

Production of 1-{3-[2-(1-benzothiophen-5-yl)ethoxy]propyl}-3-azetidinyl=pivalate

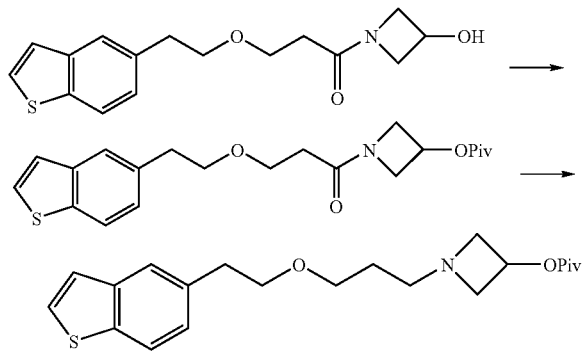

(1) In 8 mL of methylene chloride was dissolved 1.00 g of 3-[2-(1-benzothiophen-5-yl)ethoxy]-1-(3-hydroxy-1-azetidinyl)-1-propanone, and 0.40 mL of pyridine was added to the solution, after which 0.48 mL of pivaloyl chloride was added thereto under ice-cooling and the resulting mixture was stirred at room temperature for 22 hours. Water was added to the reaction mixture and the resulting mixture was acidified with 6 mol/L hydrochloric acid, after which the organic layer was separated. The organic layer was washed with a 2 mol/L aqueous sodium hydroxide solution and a saturated aqueous sodium chloride solution, dried over anhydrous magnesium sulfate, and then distilled under reduced pressure to remove the solvent. The residue was purified by a column chromatography (eluent; toluene:ethyl acetate=3:1 to 2:1) to obtain 1.20 g of 1-{3-[2-(1-benzothiophen-5-yl)ethoxy]-propanoyl}-3-azetidinyl=pivalate as a colorless oil.

IR (neat) cm$^{-1}$: 2972, 1730, 1655, 1458, 1282, 1151, 1112, 703 NMR (CDCl$_3$) δ values: 1.21 (9H, s), 2.2-2.4 (2H, m), 2.99 (2H, t, J=7 Hz), 3.6-3.8 (4H, m), 3.8-4.1 (2H, m), 4.2-4.3 (1H, m), 4.3-4.5 (1H, m), 4.9-5.1 (1H, m), 7.1-7.3 (2H, m), 7.42 (1H, d, J=5 Hz), 7.6-7.7 (1H, m), 7.80 (1H, d, J=8 Hz)

(2) In the same manner as in Example 88 (2), 1-{3-[2-(1-benzothiophen-5-yl)ethoxy]propyl}-3-azetidinyl=pivalate was obtained.

IR (neat) cm$^{-1}$: 2938, 1727, 1283, 1156, 1110, 756, 702 NMR (CDCl$_3$) δ values: 1.20 (9H, s), 1.5-1.7 (2H, m), 2.50 (2H, t, J=7 Hz), 2.8-3.0 (2H, m), 2.99 (2H, t, J=7 Hz), 3.47 (2H, t, J=6 Hz), 3.6-3.8 (4H, m), 4.9-5.1 (1H, m), 7.22 (1H, dd, J=2, 8 Hz), 7.2-7.3 (1H, m), 7.42 (1H, d, J=6 Hz), 7.6-7.7 (1H, m), 7.79 (1H, d, J=8 Hz)

EXAMPLE 91

Production of 1-{3-[2-(1-benzothiophen-5-yl)ethoxy]propyl}-3-azetidinyl=pivalate maleate

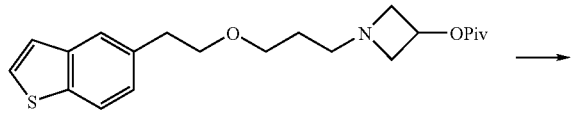

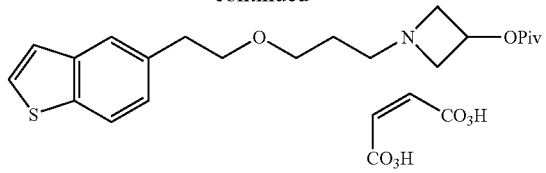

In the same manner as in Example 89, 1-{3-[2-(1-benzothiophen-5-yl)ethoxy]propyl}-3-azetidinyl=pivalate maleate was obtained.

IR (KBr) cm$^{-1}$: 2866, 1740, 1578, 1452, 1356, 1165, 1120, 870 NMR (DMSO-d$_6$) δ values: 1.18 (9H, s), 1.6-1.8 (2H, m), 2.8-3.0 (2H, m), 3.0-3.3 (2H, m), 3.3-3.6 (2H, m), 3.5-3.7 (2H, m), 3.9-4.1 (2H, m), 4.3-4.5 (2H, m), 5.0-5.2 (1H, m), 6.05 (2H, s), 7.26 (1H, d, J=8 Hz), 7.40 (1H, d, J=5 Hz), 7.7-7.8 (2H, m), 7.91 (1H, d, J=8 Hz)

EXAMPLE 92

Production of 1-{3-[2-(1-benzothiophen-5-yl)ethoxy]propyl}-3-azetidinyl=methyl=carbonate

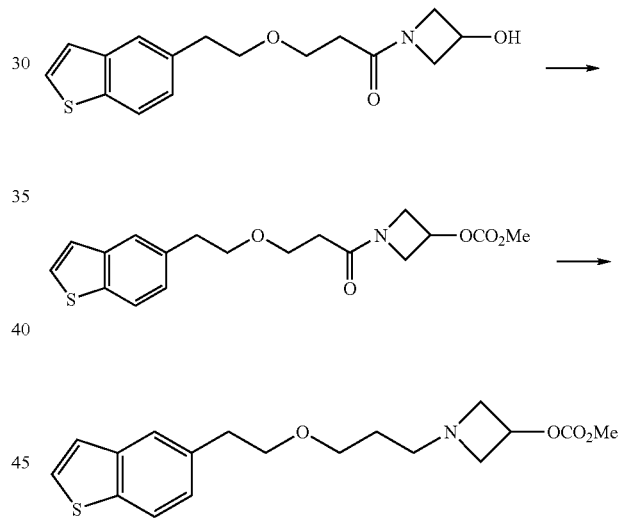

(1) In the same manner as in Example 90 (1), 1-{3-[2-(1-benzothiophen-5-yl)ethoxy]propanoyl}-3-azetidinyl=methyl=carbonate was obtained.

IR (neat) cm$^{-1}$: 2943, 1751, 1272, 1110, 791, 705 NMR (CDCl$_3$) δ values: 2.2-2.4 (2H, m), 2.99 (2H, t, J=7 Hz), 3.7-3.8 (2H, m), 3.71 (2H, t, J=7 Hz), 3.82 (3H, s), 3.9-4.0 (1H, m), 4.0-4.3 (2H, m), 4.3-4.4 (1H, m), 4.9-5.1 (1H, m), 7.21 (1H, dd, J=1, 8 Hz), 7.29 (1H, d, J=5 Hz), 7.42 (1H, d, J=5 Hz), 7.6-7.7 (1H, m), 7.80 (1H, d, J=8 Hz)

(2) In the same manner as in Example 88 (2), 1-{3-[2-(1-benzothiophen-5-yl)ethoxy]propyl}-3-azetidinyl=methyl=carbonate was obtained.

IR (neat) cm$^{-1}$: 2952, 2858, 1749, 1442, 1271, 1109, 792, 704 NMR (CDCl$_3$) δ values: 1.5-1.7 (2H, m), 2.49 (2H, t, J=7 Hz), 2.9-3.1 (4H, m), 3.46 (2H, t, J=6 Hz), 3.6-3.7 (4H, m), 3.78 (3H, s), 4.9-5.1 (1H, m), 7.21 (1H, dd, J=2, 8 Hz), 7.28 (1H, dd, J=1, 5 Hz), 7.42 (1H, d, J=5 Hz), 7.6-7.7 (1H, m), 7.79 (1H, d, J=8 Hz)

EXAMPLE 93

Production of 1-{3-[2-(1-benzothiophen-5-yl)ethoxy]propyl}-3-azetidinyl=methyl=carbonate oxalate

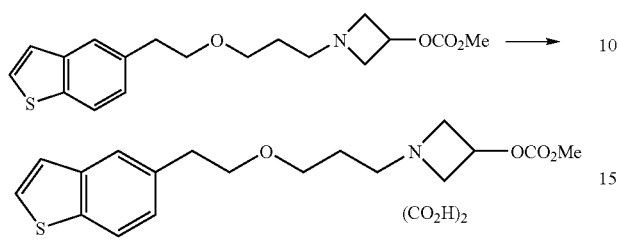

In 7 mL of ethyl acetate was dissolved 0.31 g of 1-{3-[2-(1-benzothiophen-5-yl)ethoxy]propyl}-3-azetidinyl=methyl=carbonate, and to the solution was added a solution of 0.10 g of oxalic acid in 1 mL of ethyl acetate, after which the resulting mixture was stirred at room temperature. The crystals precipitated were collected by filtration to obtain 0.34 g of 1-{3-[2-(1-benzothiophen-5-yl)ethoxy]propyl}-3-azetidinyl=methyl=carbonate oxalate.

IR (KBr) cm$^{-1}$: 2863, 2594, 1753, 1444, 1278, 1112, 719 NMR (DMSO-d$_6$) δ values: 1.6-1.8 (2H, m), 2.92 (2H, t, J=7 Hz), 3.0-3.1 (2H, m), 3.42 (2H, t, J=6 Hz), 3.62 (2H, t, J=7 Hz), 3.74 (3H, s), 3.9-4.0 (2H, m), 4.2-4.3 (2H, m), 5.0-5.2 (1H, m), 7.26 (1H, dd, J=1, 8 Hz), 7.40 (1H, dd, J=1, 5 Hz), 7.7-7.8 (2H, m), 7.90 (1H, d, J=8 Hz)

EXAMPLE 94

Production of 1-{3-[2-(1-benzothiophen-5-yl)ethoxy]propyl}-3-azetidinyl=ethyl=carbonate

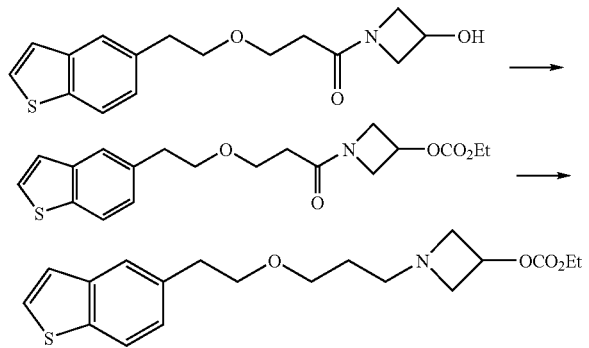

(1) In the same manner as in Example 90 (1), 1-{3-[2-(1-benzothiophen-5-yl)ethoxy]propanoyl}-3-azetidinyl=ethyl=carbonate was obtained.

IR (neat) cm$^{-1}$: 2942, 2873, 1747, 1654, 1450, 1260, 1111, 791, 704 NMR (CDCl$_3$) δ values: 1.32 (3H, t, J=7 Hz), 2.2-2.4 (2H, m), 2.99 (2H, t, J=7 Hz), 3.7-3.8 (2H, m), 3.71 (2H, t, J=7 Hz), 3.9-4.0 (1H, m), 4.0-4.2 (1H, m), 4.2-4.3 (1H, m), 4.22 (2H, q, J=7 Hz), 4.3-4.4 (1H, m), 4.9-5.1 (1H, m), 7.21 (1H, dd, J=2, 8 Hz), 7.29 (1H, d, J=5 Hz), 7.42 (1H, d, J=5 Hz), 7.6-7.7 (1H, m), 7.80 (1H, d, J=8 Hz)

(2) In the same manner as in Example 88 (2), 1-{3-[2-(1-benzothiophen-5-yl)ethoxy]propyl}-3-azetidinyl=ethyl=carbonate was obtained.

IR (neat) cm$^{-1}$: 2941, 1750, 1262, 1110, 1049, 792, 704 NMR (CDCl$_3$) δ values: 1.31 (3H, t, J=7 Hz), 1.5-1.7 (2H, m), 2.50 (2H, t, J=7 Hz), 2.9-3.1 (4H, m), 3.46 (2H, t, J=6 Hz), 3.6-3.7 (4H, m), 4.19 (2H, q, J=7 Hz), 4.9-5.1 (1H, m), 7.21 (1H, dd, J=2, 8 Hz), 7.28 (1H, dd, J=1, 5 Hz), 7.42 (1H, d, J=5 Hz), 7.6-7.7 (1H, m), 7.79 (1H, d, J=8 Hz)

EXAMPLE 95

Production of 1-{3-[2-(1-benzothiophen-5-yl)ethoxy]propyl}-3-azetidinyl=ethyl=carbonate oxalate

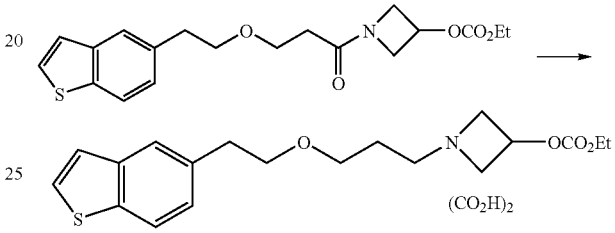

In the same manner as in Example 93, 1-{3-[2-(1-benzothiophen-5-yl)ethoxy]propyl}-3-azetidinyl=ethyl=carbonate oxalate was obtained.

IR (KBr) cm$^{-1}$: 2932, 2864, 2583, 1748, 789, 719 NMR (DMSO-d$_6$) δ values: 1.23 (3H, t, J=7 Hz), 1.6-1.8 (2H, m), 2.92 (2H, t, J=7 Hz), 3.0-3.1 (2H, m), 3.43 (2H, t, J=6 Hz), 3.62 (2H, t, J=7 Hz), 3.9-4.0 (2H, m), 4.16 (2H, q, J=7 Hz), 4.2-4.3 (2H, m), 5.0-5.2 (1H, m), 7.26 (1H, dd, J=2, 8 Hz), 7.40 (1H, d, J=6 Hz), 7.7-7.8 (2H, m), 7.90 (1H, d, J=8 Hz)

EXAMPLE 96

Production of 1-{3-[2-(1-benzothiophen-5-yl)ethoxy]propyl}-3-(methoxymethoxy)azetidine

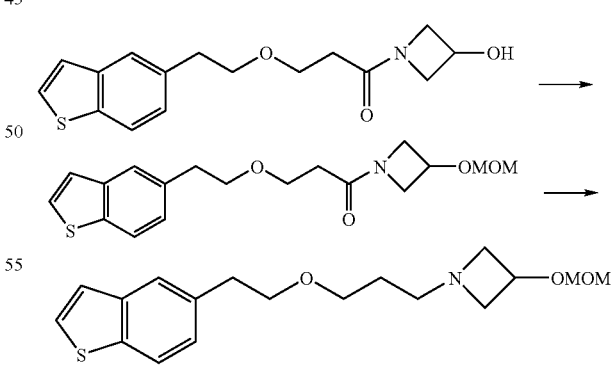

(1) In 8.5 mL of methylene chloride was dissolved 1.52 g of 3-[2-(1-benzothiophen-5-yl)ethoxy]-1-(3-hydroxy-1-azetidinyl)-1-propanone, and 2.6 mL of N,N-diisopropylethylamine was added to the solution. After the resulting mixture was cooled to 5° C., 1.0 mL of chloromethyl methyl ether was added thereto, followed by stirring at room temperature for 17 hours. Water and ethyl acetate were added to the reaction mixture and the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; toluene:ethyl acetate=3:1 to 1:1) to obtain 1.40 g of 3-[2-(1-benzothiophen-5-yl)ethoxy]-1-[3-(methoxymethoxy)-1-azetidinyl]-1-propanone as an oil.

IR (neat) cm$^{-1}$: 2941, 2867, 1654, 1112, 1055, 919, 704 NMR (CDCl$_3$) δ values: 2.3-2.4 (2H, m), 2.99 (2H, t, J=7 Hz), 3.37 (3H, s), 3.7-3.8 (2H, m), 3.72 (2H, t, J=7 Hz), 3.8-4.1 (2H, m), 4.1-4.4 (3H, m), 4.60 (2H, s), 7.21 (1H, dd, J=2, 8 Hz), 7.29 (1H, d, J=5 Hz), 7.42 (1H, d, J=5 Hz), 7.6-7.7 (1H, m), 7.79 (1H, d, J=8 Hz)

(2) In the same manner as in Example 88 (2), 1-{3-[2-(1-benzothiophen-5-yl)ethoxy]propyl}-3-(methoxymethoxy)azetidine was obtained.

IR (neat) cm$^{-1}$: 2943, 1113, 1059, 1012, 919, 703 NMR (CDCl$_3$) δ values: 1.5-1.7 (2H, m), 2.49 (2H, t, J=7 Hz), 2.8-2.9 (2H, m), 2.99 (2H, t, J=7 Hz), 3.36 (3H, s), 3.47 (2H, t, J=6 Hz), 3.5-3.7 (4H, m), 4.2-4.3 (1H, m), 4.59 (2H, s), 7.22 (1H, dd, J=1, 8 Hz), 7.28 (1H, dd, J=1, 5 Hz), 7.42 (1H, d, J=5 Hz), 7.6-7.7 (1H, m), 7.79 (1H, d, J=8 Hz)

EXAMPLE 97

Production of 1-{3-[2-(1-benzothiophen-5-yl)ethoxy]propyl}-3-(methoxymethoxy)azetidine oxalate

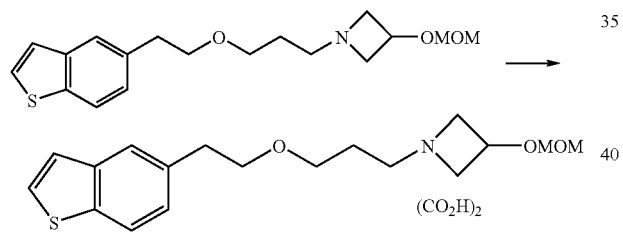

In the same manner as in Example 93, 1-{3-[2-(1-benzothiophen-5-yl)ethoxy]propyl}-3-(methoxymethoxy)azetidine oxalate was obtained.

IR (KBr) cm$^{-1}$: 2866, 1719, 1624, 1112, 989, 920, 707 NMR (DMSO-d$_6$) δ values: 1.6-1.8 (2H, m), 2.93 (2H, t, J=7 Hz), 3.0-3.1 (2H, m), 3.29 (3H, s), 3.43 (2H, t, J=6 Hz), 3.63 (2H, t, J=7 Hz), 3.7-3.9 (2H, m), 4.1-4.3 (2H, m), 4.3-4.5 (1H, m), 4.60 (2H, s), 7.26 (1H, dd, J=2, 8 Hz), 7.40 (1H, d, J=5 Hz), 7.7-7.8 (2H, m), 7.90 (1H, d, J=8 Hz)

EXAMPLE 98

Production of 1-{3-[2-(1-benzothiophen-5-yl)ethoxy]propyl}-3-[(benzyloxy)methoxy]azetidine

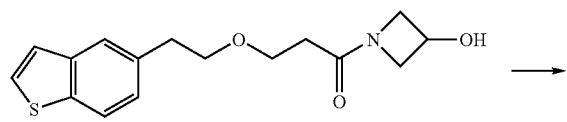

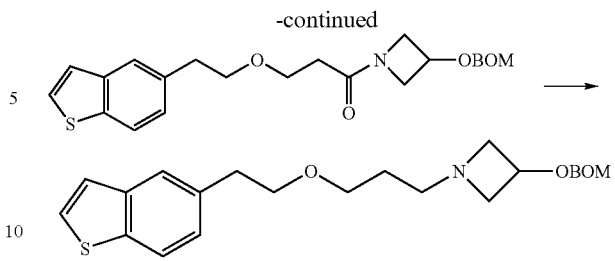

(1) In the same manner as in Example 96 (1), 3-[2-(1-benzothiophen-5-yl)ethoxy]-1-{3-[(benzyloxy)methoxy]-1-azetidinyl}-1-propanone was obtained.

IR (neat) cm$^{-1}$: 2872, 1654, 1112, 700 NMR (CDCl$_3$) δ values: 2.3-2.4 (2H, m), 2.99 (2H, t, J=7 Hz), 3.7-3.8 (2H, m), 3.71 (2H, t, J=7 Hz), 3.8-4.3 (4H, m), 4.3-4.4 (1H, m), 4.60 (2H, s), 4.73 (2H, s), 7.21 (1H, dd, J=1, 8 Hz), 7.2-7.4 (6H, m), 7.40 (1H, d, J=5 Hz), 7.6-7.7 (1H, m), 7, 79 (1H, d, J=8 Hz)

(2) In the same manner as in Example 88 (2), 1-{3-[2-(1-benzothiophen-5-yl)ethoxy]propyl}-3-[(benzyloxy)methoxy]azetidine was obtained.

IR (neat) cm$^{-1}$: 2942, 1196, 1115, 1060, 700 NMR (CDCl$_3$) δ values: 1.5-1.7 (2H, m), 2.49 (2H, t, J=7 Hz), 2.8-3.0 (2H, m), 2.99 (2H, t, J=7 Hz), 3.47 (2H, t, J=6 Hz), 3.5-3.7 (2H, m), 3.66 (2H, t, J=7 Hz), 4.2-4.4 (1H, m), 4.60 (2H, s), 4.72 (2H, s), 7.2-7.4 (6H, m), 7.22 (1H, dd, J=1, 8 Hz), 7.41 (1H, d, J=6 Hz), 7.6-7.7 (1H, m), 7.79 (1H, d, J=8 Hz)

EXAMPLE 99

Production of 1-{3-[2-(1-benzothiophen-5-yl)ethoxy]propyl}-3-(trityloxy)azetidine

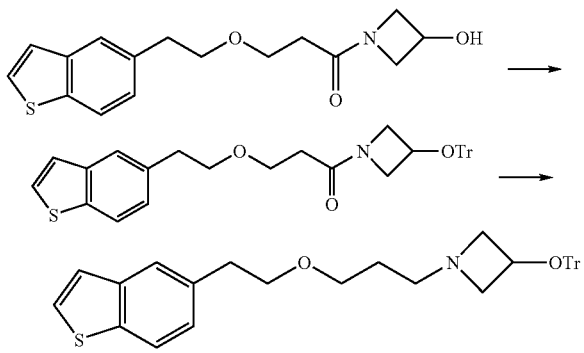

(1) In 6.8 mL of toluene was dissolved 0.85 g of 3-[2-(1-benzothiophen-5-yl)ethoxy]-1-(3-hydroxy-1-azetidinyl)-1-propanone, and to the solution were added 0.34 mL of pyridine, 0.02 g of 4-(dimethylamino)-pyridine and 0.93 g of trityl chloride, after which the resulting mixture was stirred at 50° C. for 3 hours. To the mixture was added 0.85 mL of N,N-dimethylformamide, followed by stirring at 50° C. for another 24 hours. Water and ethyl acetate were added to the reaction mixture and the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; toluene ethyl acetate=5:1 to 3:1) to obtain 1.15 g of 3-[2-(1-benzothiophen-5-yl)ethoxy]-1-[3-(trityloxy)-1-azetidinyl]-1-propanone as an oil.

IR (neat) cm$^{-1}$: 2940, 2870, 1654, 1116, 762, 707 NMR (CDCl$_3$) δ values: 2.18 (2H, t, J=6 Hz), 2.94 (2H, t, J=7 Hz), 3.5-3.8 (8H, m), 4.2-4.4 (1H, m), 7.1-7.5 (18H, m), 7.6-7.7 (1H, m), 7.73 (1H, d, J=8 Hz)

(2) In the same manner as in Example 88 (2), 1-{3-[2-(1-benzothiophen-5-yl)ethoxy]propyl}-3-(trityloxy)azetidine was obtained.

IR (neat) cm$^{-1}$: 2943, 1492, 1449, 1104, 706 NMR (CDCl$_3$) δ values: 1.4-1.6 (2H, m), 2.3-2.4 (2H, m), 2.5-2.7 (2H, m), 2.95 (2H, t, J=7 Hz), 3.0-3.1 (2H, m), 3.37 (2H, t, J=7 Hz), 3.61 (2H, t, J=7 Hz), 4.1-4.3 (1H, m), 7.1-7.3 (11H, m), 7.3-7.5 (7H, m), 7.6-7.7 (1H, m), 7.77 (1H, d, J=8 Hz)

EXAMPLE 100

Production of 1-{3-[2-(1-benzothiophen-5-yl)ethoxy]propyl}-3-(trityloxy)azetidine oxalate

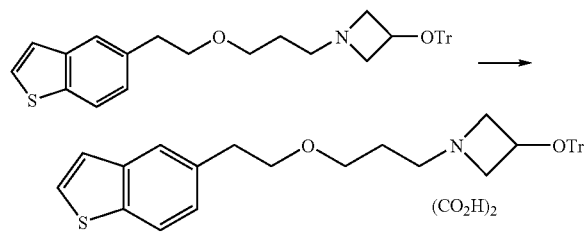

In the same manner as in Example 93, 1-{3-[2-(1-benzothiophen-5-yl)ethoxy]propyl}-3-(trityloxy)-azetidine oxalate was obtained.

IR (KBr) cm$^{-1}$: 2866, 1491, 1451, 1155, 1110, 704 NMR (DMSO-d$_6$) δ values: 1.4-1.6 (2H, m), 2.8-3.0 (4H, m), 3.34 (2H, t, J=6 Hz), 3.4-3.6 (6H, m), 4.2-4.4 (1H, m), 7.23 (1H, d, J=8 Hz), 7.3-7.5 (16H, m), 7.6-7.8 (2H, m), 7.88 (1H, d, J=8 Hz)

EXAMPLE 101

Production of 1-{3-[2-(1-benzothiophen-5-yl)ethoxy]propyl}-3-[(triethylsilyl)oxy]azetidine

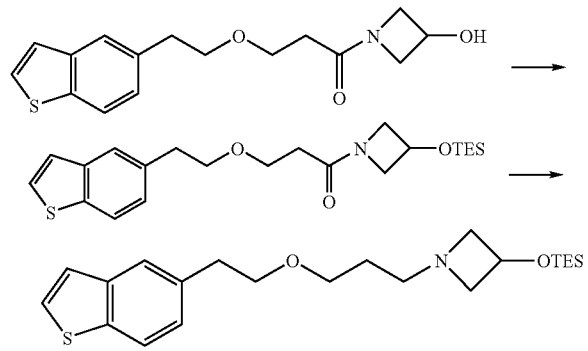

(1) In the same manner as in Example 99 (1), 3-[2-(1-benzothiophen-5-yl)ethoxy]-1-{3-[(triethylsilyl)oxy]-1-azetidinyl}-1-propanone was obtained.

IR (neat) cm$^{-1}$: 2954, 2875, 1654, 1458, 1113, 1004, 750 NMR (CDCl$_3$) δ values: 0.57 (6H, q, J=8 Hz), 0.94 (9H, t, J=8 Hz), 2.2-2.4 (2H, m), 2.99 (2H, t, J=7 Hz), 3.6-3.9 (5H, m), 3.9-4.0 (1H, m), 4.1-4.3 (2H, m), 4.4-4.6 (1H, m), 7.21 (1H, dd, J=2, 8 Hz), 7.29 (1H, d, J=5 Hz), 7.42 (1H, d, J=5 Hz), 7.6-7.7 (1H, m), 7.79 (1H, d, J=8 Hz)

(2) In the same manner as in Example 88 (2), 1-{3-[2-(1-benzothiophen-5-yl)ethoxy]propyl}-3-[(triethylsilyl)oxy]azetidine was obtained.

IR (neat) cm$^{-1}$: 2951, 1380, 1201, 1114, 865, 747, 701 NMR (CDCl$_3$) δ values: 0.57 (6H, q, J=8 Hz), 0.94 (9H, t, J=8 Hz), 1.5-1.7 (2H, m), 2.48 (2H, t, J=7 Hz), 2.7-2.8 (2H, m), 2.99 (2H, t, J=7 Hz), 3.46 (2H, t, J=6 Hz), 3.5-3.7 (2H, m), 3.66 (2H, t, J=7 Hz), 4.3-4.5 (1H, m), 7.21 (1H, dd, J=2, 8 Hz), 7.28 (1H, dd, J=1, 8), 7.41 (1H, d, J=6 Hz), 7.6-7.7 (1H, m), 7.79 (1H, d, J=8 Hz)

EXAMPLE 102

Production of 1-{3-[2-(1-benzothiophen-5-yl)ethoxy]propyl}-3-(benzyloxy)azetidine

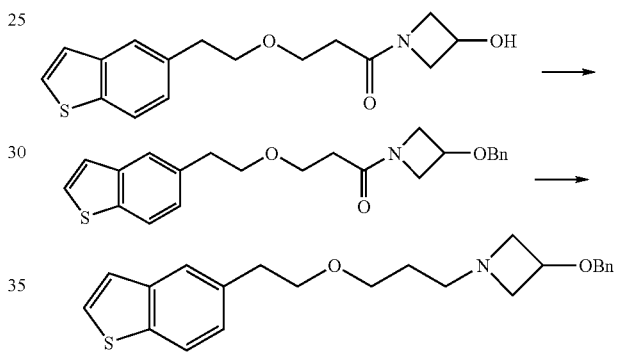

(1) In 8 mL of N,N-dimethylformamide was dissolved 1.00 g of 3-[2-(1-benzothiophen-5-yl)ethoxy]-1-(3-hydroxy-1-azetidinyl)-1-propanone, and 1.90 g of silver(I) oxide and 0.97 mL of benzyl bromide were added to the solution, after which the resulting mixture was stirred at room temperature for 31 hours. The insoluble materials were filtered off and water and ethyl acetate were added to the residue, after which the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; toluene: ethyl acetate=3:1 to 1:4) to obtain 1.00 g of 3-[2-(1-benzothiophen-5-yl)ethoxy]-1-[3-(benzyloxy)-1-azetidinyl]-1-propanone as an oil.

IR (neat) cm$^{-1}$: 2869, 1654, 1112, 754, 700 NMR (CDCl$_3$) δ values: 2.2-2.4 (2H, m), 2.98 (2H, t, J=7 Hz), 3.6-3.8 (4H, m), 3.8-3.9 (1H, m), 3.9-4.0 (1H, m), 4.0-4.1 (1H, m), 4.1-4.3 (2H, m), 4.40 (1H, d, J=12 Hz), 4.44 (1H, d, J=12 Hz), 7.20 (1H, dd, J=1, 8 Hz), 7.2-7.5 (7H, m), 7.6-7.7 (1H, m), 7.78 (1H, d, J=8 Hz)

(2) In the same manner as in Example 1 (2), 1-{3-[2-(1-benzothiophen-5-yl)ethoxy]propyl}-3-(benzyloxy)azetidine was obtained.

IR (neat) cm$^{-1}$: 2939, 1355, 1194, 1110, 754, 700 NMR (CDCl$_3$) δ values: 1.5-1.7 (2H, m), 2.48 (2H, t, J=7 Hz), 2.8-2.9 (2H, m), 2.98 (2H, t, J=7 Hz), 3.46 (2H, t, J=6 Hz), 3.5-3.7 (2H, m), 3.65 (2H, t, J=7 Hz), 4.1-4.3 (1H, m), 4.42

(2H, s), 7.21 (1H, dd, J=1, 8 Hz), 7.2-7.4 (6H, m), 7.41 (1H, d, J=5 Hz), 7.6-7.7 (1H, m), 7.79 (1H, d, J=8 Hz)

EXAMPLE 103

Production of 1-{3-[2-(1-benzothiophen-5-yl) ethoxy]propyl}-3-(benzyloxy)azetidine oxalate

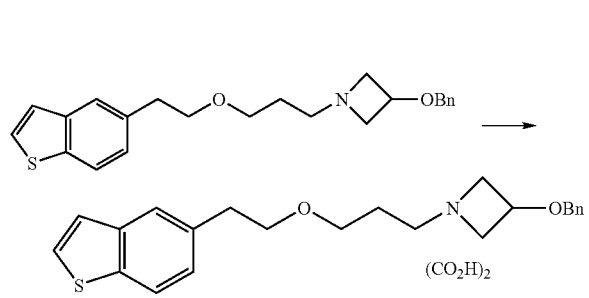

In the same manner as in Example 93, 1-{3-[2-(1-benzothiophen-5-yl)ethoxy]propyl}-3-(benzyloxy)azetidine oxalate was obtained.

IR (KBr) cm$^{-1}$: 2859, 1111, 700 NMR (DMSO-d$_6$) δ values: 1.6-1.8 (2H, m), 2.92 (2H, t, J=7 Hz), 3.06 (2H, t, J=7 Hz), 3.42 (2H, t, J=6 Hz), 3.62 (2H, t, J=7 Hz), 3.7-3.9 (2H, m), 4.1-4.2 (2H, m), 4.3-4.4 (1H, m), 4.46 (2H, s), 7.26 (1H, d, J=8 Hz), 7.3-7.5 (6H, m), 7.7-7.8 (2H, m), 7.90 (1H, d, J=8 Hz)

EXAMPLE 104

Production of 1-{3-[2-(1-benzothiophen-5-yl) ethoxy]propyl}-3-(trityloxy)azetidine

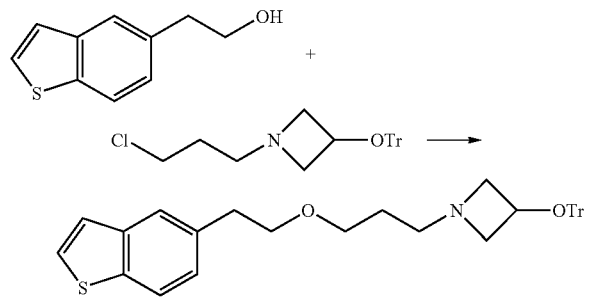

In a mixture of 0.4 mL of toluene and 7 mL of a 50% (W/V) aqueous sodium hydroxide solution was suspended 0.54 g of 2-(1-benzothiophen-5-yl)-1-ethanol, followed by adding thereto 1.45 g of 1-(3-chloropropyl)-3-(trityloxy)azetidine oxalate and 0.03 g of tetra-n-butylammonium bromide, and the resulting mixture was refluxed for 7 hours. After the reaction mixture was cooled, water and toluene were added thereto and the organic layer was separated. The organic layer was washed with a saturated aqueous sodium chloride solution, dried over anhydrous magnesium sulfate, and then distilled under reduced pressure to remove the solvent. The residue was purified by a column chromatography (eluent; chloroform:methanol=75:1) to obtain 0.59 g of 1-{3-[2-(1-benzothiophen-5-yl)ethoxy]propyl}-3-(trityloxy)azetidine as a light-yellow oil.

EXAMPLE 105

Production of 1-{3-[2-(1-benzothiophen-5-yl) ethoxy]propyl}-3-(trityloxy)azetidine maleate

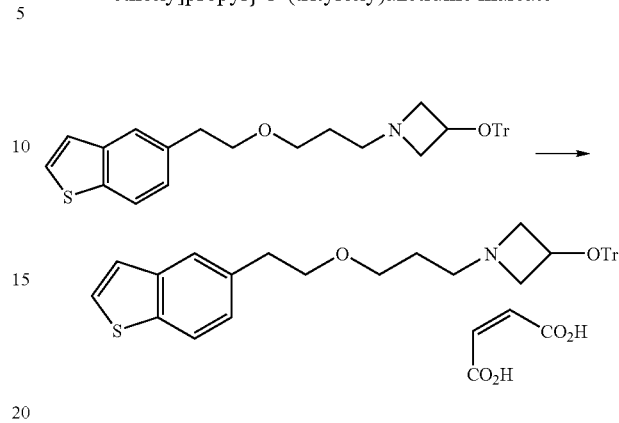

In the same manner as in Example 89, 1-{3-[2-(1-benzothiophen-5-yl)ethoxy]propyl}-3-(trityloxy)-azetidine maleate was obtained.

IR (KBr) cm$^{-1}$: 3059, 1346, 1119, 871, 706 NMR (CDCl$_3$) δ values: 1.6-1.8 (2H, m), 2.8-3.0 (4H, m), 3.1-3.3 (2H, m), 3.40 (2H, t, J=6 Hz), 3.63 (2H, t, J=7 Hz), 3.8-4.0 (2H, m), 4.4-4.6 (1H, m), 6.23 (2H, s), 7.18 (1H, d, J=8 Hz), 7.2-7.5 (17H, m), 7.64 (1H, s), 7.79 (1H, d, J=8 Hz)

EXAMPLE 106

Production of 1-{3-[2-(1-benzothiophen-5-yl) ethoxy]propyl}-3-(tetrahydro-2H-pyran-2-yloxy) azetidine

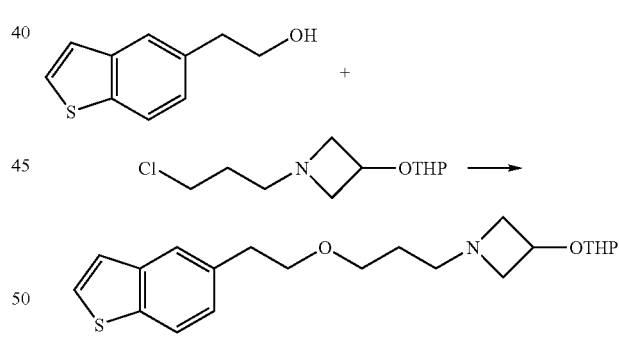

In the same manner as in Example 104, 1-{3-[2-(1-benzothiophen-5-yl)ethoxy]propyl}-3-(tetrahydro-2H-pyran-2-yloxy)azetidine was obtained from 2-(1-benzothiophen-5-yl)-1-ethanol and 1-(3-chloropropyl)-3-(tetrahydro-2H-pyran-2-yloxy)azetidine.

IR (neat) cm$^{-1}$: 2943, 2853, 1201, 1115, 1037, 975, 703 NMR (CDCl$_3$) δ values: 1.4-1.9 (8H, m), 2.49 (2H, t, J=7 Hz), 2.8-3.0 (2H, m), 2.98 (2H, t, J=7 Hz), 3.4-3.6 (1H, m), 3.46 (2H, t, J=6 Hz), 3.5-3.7 (4H, m), 3.8-3.9 (1H, m), 4.2-4.4 (1H, m), 4.5-4.6 (1H, m), 7.21 (1H, dd, J=2, 8 Hz), 7.28 (1H, dd, J=1, 6 Hz), 7.41 (1H, d, J=6 Hz), 7.6-7.7 (1H, m), 7.78 (1H, d, J=8 Hz)

EXAMPLE 107

Production of 1-{3-[2-(1-benzothiophen-5-yl)ethoxy]propyl}-3-azetidinyl=pivalate

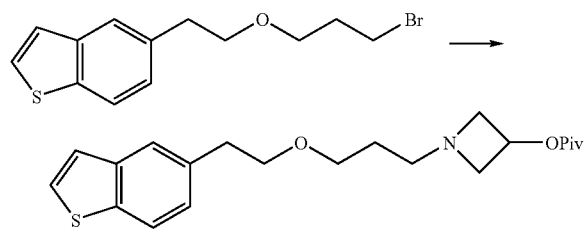

In 3.75 mL of dimethyl sulfoxide was dissolved 0.75 g of 5-[2-(3-bromopropoxy)ethyl]-1-benzothiophene, and 0.63 g of sodium hydrogencarbonate and 0.73 g of 3-azetidinyl=pivalate hydrochloride were added to the solution, after which the resulting mixture was stirred at 70° C. for 4 hours. After the reaction mixture was cooled, 20 mL of water and 15 mL of ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; toluene:ethyl acetate=1:1 to 1:5) to obtain 0.78 g of 1-{3-[2-(1-benzothiophen-5-yl)ethoxy]propyl}-3-azetidinyl=pivalate as a light-yellow oil.

EXAMPLE 108

Production of 1-{3-[2-(1-benzothiophen-5-yl)ethoxy]propyl}-3-(trityloxy)azetidine

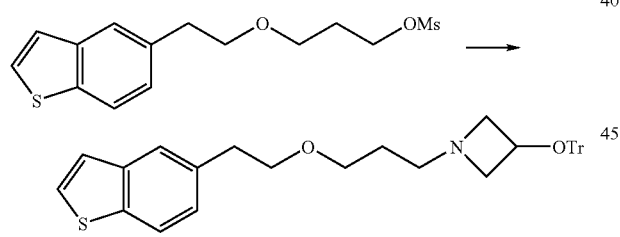

In 15 mL of water was suspended 2.69 g of 3-(trityloxy)azetidine hydrochloride, and 20 mL of ethyl acetate was added thereto, after which the pH was adjusted to 9 with a 2 mol/l aqueous sodium hydroxide solution and the organic layer was separated. The organic layer was washed with water and then a saturated aqueous sodium chloride solution, dried over anhydrous magnesium sulfate, and then distilled under reduced pressure to remove the solvent. The resulting residue was dissolved in 10 mL of dimethyl sulfoxide, and to the resulting solution were added 0.80 g of sodium hydrogencarbonate and 2.00 g of 3-[2-(1-benzothiophen-5-yl)ethoxy]propyl=methanesulfonate, followed by stirring at 50° C. for 3 hours. To the reaction mixture were added 20 mL of water and 20 mL of ethyl acetate, and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; toluene:ethyl acetate=3:1 to 1:3) to obtain 2.89 g of 1-{3-[2-(1-benzothiophen-5-yl)ethoxy]propyl}-3-(trityloxy)azetidine as a light-yellow oil.

EXAMPLE 109

Production of 1-{3-[2-(1-benzothiophen-5-yl)ethoxy]propyl}-3-azetidinyl=acetate

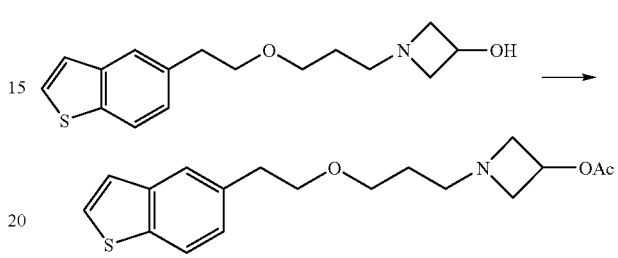

In 15 mL of tetrahydrofuran was dissolved 1.50 g of 1-{3-[2-(1-benzothiophen-5-yl)ethoxy]propyl}-3-azetidinol, and 0.73 mL of acetic anhydride and 0.06 mL of a boron trifluoride-diethyl ether complex were added thereto under ice-cooling, after which the resulting mixture was stirred at room temperature for 1 hour. Ethyl acetate and a saturated aqueous sodium hydrogencarbonate solution were added to the reaction mixture and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; chloroform:methanol=100:1 to 50:1) to obtain 1.63 g of 1-{3-[2-(1-benzothiophen-5-yl)ethoxy]propyl}-3-azetidinyl=acetate as a light-yellow oil.

IR (neat) cm$^{-1}$: 2941, 2859, 1741, 1375, 1239, 1109, 756, 703 NMR (CDCl$_3$) δ values: 1.5-1.7 (2H, m), 2.06 (3H, s), 2.49 (2H, t, J=7 Hz), 2.9-3.1 (4H, m), 3.46 (2H, t, J=6 Hz), 3.5-3.7 (2H, m), 3.66 (2H, t, J=7 Hz), 4.9-5.1 (1H, m), 7.21 (1H, dd, J=1, 8 Hz), 7.28 (1H, d, J=5 Hz), 7.42 (1H, d, J=5 Hz), 7.6-7.7 (1H, m), 7.79 (1H, d, J=8 Hz)

EXAMPLE 110

Production of 1-{3-[2-(1-benzothiophen-5-yl)ethoxy]propyl}-3-azetidinyl=acetate oxalate

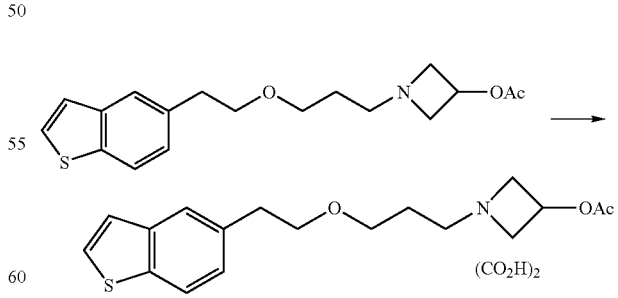

In the same manner as in Example 93, 1-{3-[2-(1-benzothiophen-5-yl)ethoxy]propyl}-3-azetidinyl=acetate oxalate was obtained.

IR (KBr) cm$^{-1}$: 2862, 1745, 1253, 1108, 711 NMR (DMSO-d$_6$) δ values: 1.6-1.8 (2H, m), 2.06 (3H, s), 2.92 (2H, t, J=7 Hz), 3.05 (2H, t, J=7 Hz), 3.43 (2H, t, J=6 Hz), 3.62 (2H, t, J=7 Hz), 3.8-4.0 (2H, m), 4.2-4.3 (2H, m), 5.0-5.2 (1H, m), 7.26 (1H, dd, J=1, 8 Hz), 7.40 (1H, d, J=6 Hz), 7.7-7.8 (2H, m), 7.91 (1H, d, J=8 Hz)

EXAMPLE 111

Production of 1-{3-[2-(1-benzothiophen-5-yl)ethoxy]propyl}-3-azetidinol maleate

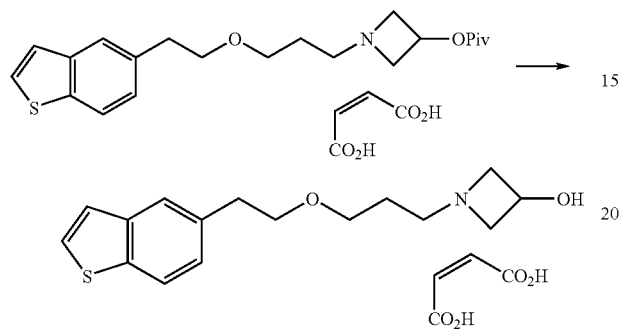

In 2.6 mL of isopropanol was suspended 1.30 g of 1-{3-[2-(1-benzothiophen-5-yl)ethoxy]propyl}-3-azetidinyl=pivalate maleate, and 2.1 mL of a 5 mol/L aqueous sodium hydroxide solution was added thereto at 20° C., after which the resulting mixture was stirred at room temperature for 6 hours. Water and ethyl acetate were added to the reaction mixture, and the organic layer was separated and then washed successively with water and a saturated aqueous sodium chloride solution. To the organic layer was added 0.29 g of maleic acid, and the resulting mixture was heated to effect dissolution, after which the solvent was distilled off under reduced pressure. To the resulting residue were added 5.2 mL of ethyl acetate and 1.3 mL of isopropanol, and the resulting mixture was stirred at room temperature for 30 minutes and then under ice-cooling for 1 hour. The crystals precipitated were collected by filtration to obtain 0.76 g of 1-{3-[2-(1-benzothiophen-5-yl)ethoxy]propyl}-3-azetidinol maleate as colorless crystals.

EXAMPLE 112

Production of 1-{3-[2-(1-benzothiophen-5-yl)ethoxy]propyl}-3-azetidinol maleate

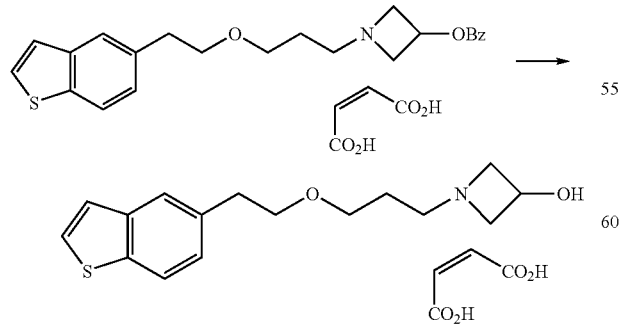

In 10 mL of isopropanol was suspended 2.00 g of 1-{3-[2-(1-benzothiophen-5-yl)ethoxy]propyl}-3-azetidinyl=benzoate maleate, and 7.82 mL of a 2 mol/L aqueous sodium hydroxide solution was added thereto, after which the resulting mixture was stirred at room temperature for 1 hour. Water and ethyl acetate were added to the reaction mixture and the organic layer was separated. The organic layer was washed with water and then a saturated aqueous sodium chloride solution, dried over anhydrous magnesium sulfate, and then distilled under reduced pressure to remove the solvent. To the residue was added 0.43 g of maleic acid, and crystallization from ethyl acetate-isopropanol (4:1, 10 mL) was carried out to obtain 1.29 g of 1-{3-[2-(1-benzothiophen-5-yl)ethoxy]propyl}-3-azetidinol maleate as colorless crystals.

EXAMPLE 113

Production of 1-{3-[2-(1-benzothiophen-5-yl)ethoxy]propyl}-3-azetidinol maleate

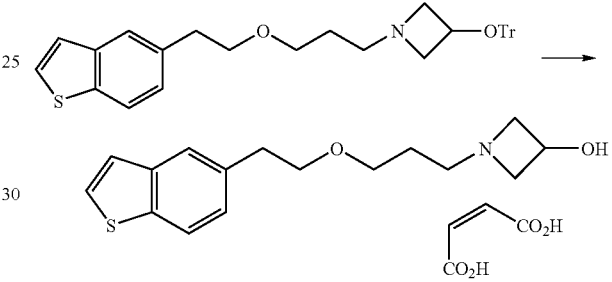

In 4 mL of chloroform was dissolved 0.83 g of 1-{3-[2-(1-benzothiophen-5-yl)ethoxy]propyl}-3-(trityloxy)azetidine, and 1.66 mL of a 4.75 mol/L dried hydrogen chloride-ethanol solution was added thereto, after which the resulting mixture was stirred at room temperature for 6 hours. Water and chloroform were added to the reaction mixture and the aqueous layer was separated. Ethyl acetate was added to the aqueous layer and the pH was adjusted to 10 with a 5 mol/L aqueous sodium hydroxide solution, after which the organic layer was separated. The organic layer was washed with water and then a saturated aqueous sodium chloride solution, dried over anhydrous magnesium sulfate, and then distilled under reduced pressure to remove the solvent. To the residue was added 0.11 g of maleic acid, and crystallization from ethyl acetate-isopropanol (4:1, 5 mL) was carried out to obtain 0.33 g of 1-{3-[2-(1-benzothiophen-5-yl)ethoxy]propyl}-3-azetidinol maleate as colorless crystals.

REFERENCE EXAMPLE 1

Production of 3-[2-(1-benzothiophen-4-yl)ethoxy]-1-propanol

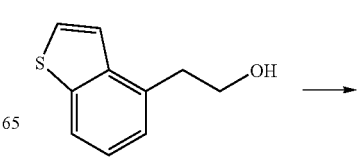

-continued

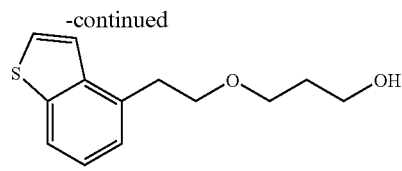

In a mixture of 2.2 mL of toluene and 8.8 mL of a 50% (W/V) aqueous sodium hydroxide solution was suspended 2.2 g of 2-(1-benzothiophen-4-yl)-1-ethanol, followed by adding thereto 4.41 g of 2-(3-chloropropoxy)tetrahydro-2H-pyran and 0.42 g of tetra-n-butylammonium hydrogensulfate, and the resulting mixture was heated under reflux for 2 hours. After the reaction mixture was cooled, water and toluene were added thereto and the organic layer was separated. The organic layer was washed with water and then a saturated aqueous sodium chloride solution, and dried over anhydrous magnesium sulfate. Then, the solvent was distilled off under reduced pressure to obtain 6.50 g of a mixture of 2-{3-[2-(1-benzothiophen-4-yl)ethoxy]propoxy}tetrahydro-2H-pyran and 2-(3-chloropropoxy)tetrahydro-2H-pyran as a light-brown oil.

In 8.0 mL of methanol was dissolved 6.50 g of this mixture, followed by adding thereto 8.0 mL of water and 0.70 g of p-toluenesulfonic acid monohydrate, and the resulting mixture was stirred at room temperature for 12 hours. Ethyl acetate and a saturated aqueous sodium hydrogencarbonate solution were added to the reaction mixture and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; toluene:ethyl acetate=4:1 to 3:1) to obtain 1.42 g of 3-[2-(1-benzothiophen-4-yl)ethoxy]-1-propanol as an oil.

IR (neat) $cm^{-1}$: 3394, 2943, 2867, 1413, 1110, 761 NMR (CDCl$_3$) δ values: 1.81 (2H, qn, J=6 Hz), 2.1 (1H, brs), 3.26 (2H, t, J=7 Hz), 3.63 (2H, t, J=6 Hz), 3.69 (2H, t, J=7 Hz), 3.76 (2H, t, J=6 Hz), 7.0-7.4 (2H, m), 7.45 (2H, s), 7.77 (1H, dd, J=2, 7 Hz)

REFERENCE EXAMPLE 2

The following compounds were obtained in the same manner as in Reference Example 1.

3-[2-(1-Benzothiophen-2-yl)ethoxy]-1-propanol NMR (CDCl$_3$) δ values: 1.68 (1H, brs), 1.86 (2H, qn, J=6 Hz), 3.17 (2H, t, J=6 Hz), 3.67 (2H, t, J=6 Hz), 3.76 (4H, t, J=6 Hz), 7.07 (1H, s), 7.2-7.4 (2H, m), 7.67 (1H, d, J=8 Hz), 7.77 (1H, d, J=8 Hz)

3-[2-(1-Benzothiophen-3-yl)ethoxy]-1-propanol

IR (neat) $cm^{-1}$: 3395, 2942, 2867, 1427, 1113, 762, 732 NMR (CDCl$_3$) δ values: 1.83 (2H, qn, J=6 Hz), 2.27 (1H, t, J=6 Hz), 3.13 (2H, t, J=7 Hz), 3.65 (2H, t, J=6 Hz), 3.74 (2H, t, J=6 Hz), 3.78 (2H, t, J=7 Hz), 7.18 (1H, s), 7.34 (1H, dt, J=1, 7 Hz), 7.39 (1H, dt, J=1, 7 Hz), 7.76 (1H, dd, J=1, 7 Hz), 7.86 (1H, dd, J=1, 7 Hz)

3-[2-(1-Benzothiophen-5-yl)ethoxy]-1-propanol

IR (neat) $cm^{-1}$: 3398, 2939, 2866, 1438, 1110, 704 NMR (CDCl$_3$) δ values: 1.82 (2H, qn, J=6 Hz), 2.29 (1H, t, J=6 Hz), 3.00 (2H, t, J=7 Hz), 3.64 (2H, t, J=6 Hz), 3.71 (2H, t, J=7 Hz), 3.73 (2H, q, J=6 Hz), 7.22 (1H, dd, J=1, 8 Hz), 7.28 (1H, d, J=5 Hz), 7.42 (1H, d, J=5 Hz), 7.66 (1H, d, J=1 Hz), 7.80 (1H, d, J=8 Hz)

3-[2-(1-Benzothiophen-6-yl)ethoxy]-1-propanol

IR (neat) $cm^{-1}$: 3389, 2942, 2865, 1397, 1111, 819, 693 NMR (CDCl$_3$) δ values: 1.82 (2H, qn, J=6 Hz), 2.24 (1H, t, J=6 Hz), 3.00 (2H, t, J=7 Hz), 3.64 (2H, t, J=6 Hz), 3.71 (2H, t, J=7 Hz), 3.74 (2H, q, J=6 Hz), 7.21 (1H, d, J=8 Hz), 7.28 (1H, d, J=5 Hz), 7.38 (1H, d, J=5 Hz), 7.70 (1H, s), 7.75 (1H, d, J=8 Hz)

3-[2-(1-Benzothiophen-7-yl)ethoxy]-1-propanol

REFERENCE EXAMPLE 3

Production of 4-[2-(3-chloropropoxy)ethyl]-1-benzothiophene

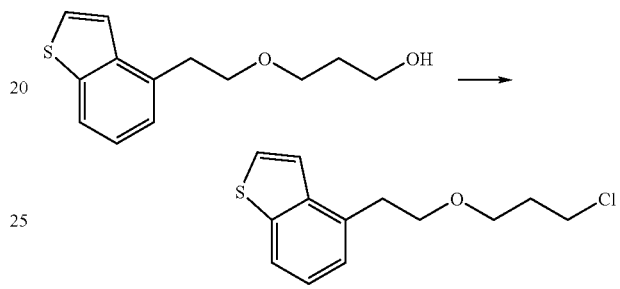

In 7.0 mL of methylene chloride was dissolved 1.40 g of 3-[2-(1-benzothiophen-4-yl)ethoxy]-1-propanol, followed by adding thereto 1.10 mL of thionyl chloride and 0.05 mL of N,N-dimethylformamide, and the resulting mixture was heated under reflux for 5 hours. Then, the solvent was distilled off under reduced pressure. The residue was purified by a column chromatography (eluent; hexane:ethyl acetate=20: 1) to obtain 1.43 g of 4-[2-(3-chloropropoxy)ethyl]-1-benzothiophene as a yellow oil.

IR (neat) $cm^{-1}$: 2867, 1413, 1113, 760 NMR (CDCl$_3$) δ values: 1.99 (2H, qn, J=6 Hz), 3.23 (2H, t, J=7 Hz), 3.58 (2H, t, J=6 Hz), 3.59 (2H, t, J=6 Hz), 3.75 (2H, t, J=7 Hz), 7.18 (1H, dd, J=2, 7 Hz), 7.29 (1H, t, J=7 Hz), 7.1-7.3 (2H, m), 7.45 (2H, s), 7.76 (1H, dd, J=2, 8 Hz)

REFERENCE EXAMPLE 4

The following compounds were obtained in the same manner as in Reference Example 3.

2-[2-(3-Chloropropoxy)ethyl]-1-benzothiophene NMR (CDCl$_3$) δ values: 2.04 (2H, qn, J=6 Hz), 3.16 (2H, t, J=7 Hz), 3.62 (2H, t, J=6 Hz), 3.66 (2H, t, J=6 Hz), 3.75 (2H, t, J=7 Hz), 7.06 (1H, s), 7.25 (1H, dt, J=1, 7 Hz), 7.30 (1H, dt, J=1, 7 Hz), 7.67 (1H, dd, J=1, 7 Hz), 7.77 (1H, dd, J=1, 7 Hz)

3-[2-(3-Chloropropoxy)ethyl]-1-benzothiophene

IR (neat) $cm^{-1}$: 2865, 1427, 1115, 762, 732 NMR (CDCl$_3$) δ values: 2.02 (2H, qn, J=6 Hz), 3.13 (2H, t, J=7 Hz), 3.61 (2H, t, J=6 Hz), 3.62 (2H, t, J=6 Hz), 3.79 (2H, t, J=7 Hz), 7.19 (1H, s), 7.34 (1H, dt, J=1, 7 Hz), 7.39 (1H, dt, J=1, 7 Hz), 7.77 (1H, dd, J=1, 7 Hz), 7.86 (1H, dd, J=1, 7 Hz)

5-[2-(3-Chloropropoxy)ethyl]-1-benzothiophene

IR (neat) $cm^{-1}$: 2864, 1438, 1113, 755, 701 NMR (CDCl$_3$) δ values: 2.01 (2H, qn, J=6 Hz), 3.00 (2H, t, J=7 Hz), 3.59 (2H, t, J=6 Hz), 3.61 (2H, t, J=6 Hz), 3.70 (2H, t, J=7 Hz), 7.22 (1H, dd, J=1, 8 Hz), 7.28 (1H, d, J=5 Hz), 7.42 (1H, d, J=5 Hz), 7.68 (1H, d, J=1 Hz), 7.79 (1H, d, J=8 Hz)

6-[2-(3-Chloropropoxy)ethyl]-1-benzothiophene

IR (neat) cm$^{-1}$: 2864, 1113, 820, 761, 695, 652 NMR (CDCl$_3$) δ values: 2.00 (2H, qn, J=6 Hz), 3.00 (2H, t, J=7 Hz), 3.58 (2H, t, J=6 Hz), 3.61 (2H, t, J=6 Hz), 3.70 (2H, t, J=7 Hz), 7.21 (1H, d, J=8 Hz), 7.28 (1H, d, J=5 Hz), 7.37 (1H, d, J=5 Hz), 7.72 (1H, s), 7.73 (1H, d, J=8 Hz)

7-[2-(3-Chloropropoxy)ethyl]-1-benzothiophene

IR (neat) cm$^{-1}$: 2866, 1460, 1395, 1115, 795, 701 NMR (CDCl$_3$) δ values: 2.00 (2H, qn, J=6 Hz), 3.17 (2H, t, J=7 Hz), 3.60 (4H, t, J=6 Hz), 3.82 (2H, t, J=7 Hz), 7.20 (1H, d, J=8 Hz), 7.33 (1H, t, J=8 Hz), 7.35 (1H, d, J=5 Hz), 7.42 (1H, d, J=5 Hz), 7.70 (1H, d, J=8 Hz)

REFERENCE EXAMPLE 5

Production of 3-[2-(1-benzothiophen-5-yl)ethoxy]propyl=methanesulfonate

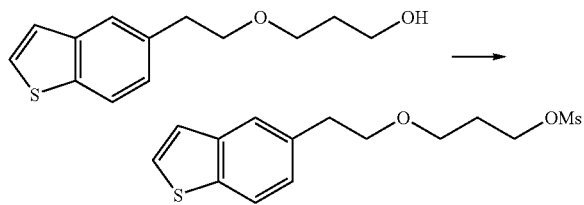

In 16.8 mL of methylene chloride was dissolved 2.03 g of 3-[2-(1-benzothiophen-5-yl)ethoxy]-1-propanol, and to the solution were added 2.43 mL of methanesulfonyl chloride, 4.37 mL of triethylamine and 0.10 g of 4-(dimethylamino)pyridine under ice-cooling, after which the resulting mixture was stirred at the same temperature for 30 minutes and then at room temperature for 12 hours. Methylene chloride and water were added to the reaction mixture and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; hexane:ethyl acetate=5:1) to obtain 1.40 g of 3-[2-(1-benzothiophen-5-yl)ethoxy]propyl=methanesulfonate.

IR (neat) cm$^{-1}$: 2937, 2866, 1352, 1174, 1114, 943, 705, 529 NMR (CDCl$_3$) δ values: 1.97 (2H, qn, J=6 Hz), 2.81 (3H, s), 2.98 (2H, t, J=7 Hz), 3.54 (2H, t, J=6 Hz), 3.70 (2H, t, J=6 Hz), 4.26 (2H, t, J=7 Hz), 7.20 (1H, dd, J=1, 8 Hz), 7.28 (1H, d, J=5 Hz), 7.42 (1H, d, J=5 Hz), 7.65 (1H, d, J=1 Hz), 7.79 (1H, d, J=8 Hz)

REFERENCE EXAMPLE 6

Production of 2-[2-(6-methoxy-1-benzofuran-5-yl)ethoxy]acetic acid and 2-[2-(5-methoxy-1-benzofuran-6-yl)ethoxy]acetic acid (1) Production of 2,4-dimethoxyphenethyl=acetate

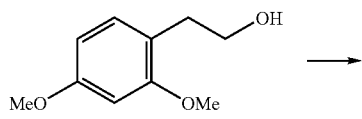

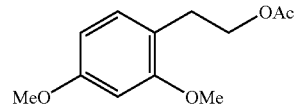

In 150 mL of methylene chloride was dissolved 15.0 g of 2-(2,4-dimethoxyphenyl)-1-ethanol, and to the 10 solution were added 9.32 mL of acetic anhydride, 13.8 mL of triethylamine and 0.10 g of 4-(dimethylamino)-pyridine under ice-cooling, after which the resulting mixture was stirred at the same temperature for 30 minutes and then at room temperature for 12 hours. Water was added to the reaction mixture and the pH was adjusted to 1.5 with 6 mol/L hydrochloric acid, after which the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; hexane ethyl acetate=5:1) to obtain 17.2 g of 2,4-dimethoxyphenethyl=acetate as a colorless oil.

IR (neat) cm$^{-1}$: 2958, 1736, 1509, 1243, 1035, 834 NMR (CDCl$_3$) δ values: 2.03 (3H, s), 2.87 (2H, t, J=7 Hz), 3.80 (6H, s), 4.22 (2H, t, J=7 Hz), 6.41 (1H, d, J=9 Hz), 6.46 (1H, s), 7.05 (1H, d, J=9 Hz)

In the same manner as above, 2,5-dimethoxyphenethyl=acetate was obtained.

IR (neat) cm$^{-1}$: 2952, 1736, 1502, 1226, 1048, 802, 710 NMR (CDCl$_3$) δ values: 2.01 (3H, s), 2.90 (2H, t, J=7 Hz), 3.74 (3H, s), 3.76 (3H, s), 4.25 (2H, t, J=7 Hz), 6.74 (3H, s)

(2) Production of 5-acetyl-2,4-dimethoxyphenethyl=acetate

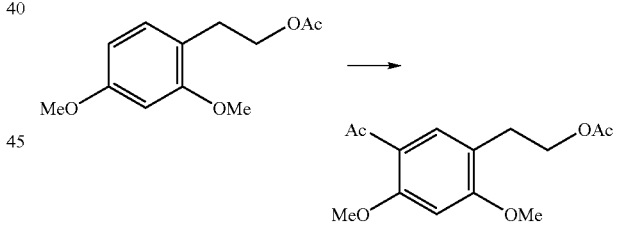

In 170 mL of methylene chloride was dissolved 17.0 g of 2,4-dimethoxyphenethyl=acetate, and 5.93 mL of acetyl chloride and 12.1 g of aluminum chloride were added to the solution under ice-cooling, after which the resulting mixture was stirred at the same temperature for 1 hour. The reaction mixture was poured into ice water and the organic layer was separated. The organic layer was washed with water and then a saturated aqueous sodium chloride solution, dried over anhydrous magnesium sulfate, and then distilled under reduced pressure to remove the solvent. Diisopropyl ether was added to the residue and the crystals precipitated were collected by filtration, washed with diisopropyl ether and then dried to obtain 13.9 g of 5-acetyl-2,4-dimethoxyphenethyl=acetate as yellow crystals.

NMR (CDCl$_3$) δ values: 2.01 (3H, s), 2.57 (3H, s), 2.88 (2H, t, J=7 Hz), 3.90 (3H, s), 3.93 (3H, s), 4.21 (2H, t, J=7 Hz), 6.42 (1H, s), 7.68 (1H, s)

In the same manner as above, 4-acetyl-2,5-dimethoxyphenethyl=acetate was obtained.

(3) Production of 5-acetyl-4-hydroxy-2-methoxy-phenethyl=acetate

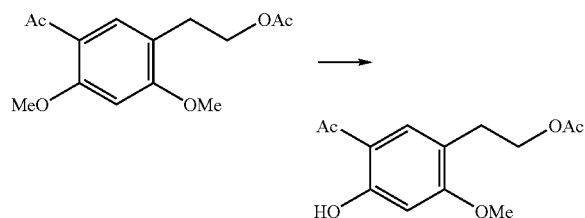

In 70 mL of acetonitrile was dissolved 13.9 g of 5-acetyl-2,4-dimethoxyphenethyl=acetate, and 13.9 g of aluminum chloride and 7.82 g of sodium iodide were added to the solution under ice-cooling, after which the resulting mixture was stirred at 50° C. for 3 hours. The reaction mixture was poured into ice water and to the resulting mixture was added ethyl acetate, after which the organic layer was separated. The organic layer was washed with water and then a saturated aqueous sodium chloride solution, and dried over anhydrous magnesium sulfate. The solvent was distilled off under reduced pressure to obtain 13.3 g of 5-acetyl-4-hydroxy-2-methoxyphenethyl=acetate as a yellow oil.

In the same manner as above, 4-acetyl-5-hydroxy-2-methoxyphenethyl=acetate was obtained.

(4) Production of 1-[2-hydroxy-5-(2-hydroxyethyl)-4-methoxyphenyl]-1-ethanone

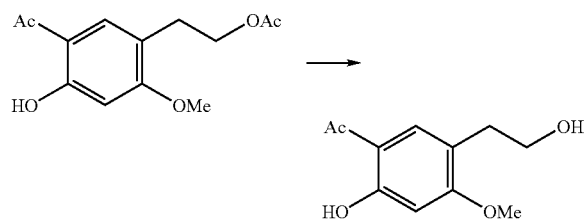

In 30 mL of ethanol was dissolved 13.3 g of the aforesaid 5-acetyl-4-hydroxy-2-methoxyphenethyl=acetate, and to the solution was added 21 mL of a 5 mol/L aqueous sodium hydroxide solution, after which the resulting mixture was stirred at room temperature for 17 hours. Water and ethyl acetate were added to the reaction mixture and the pH was adjusted to 1 with 6 mol/L hydrochloric acid, after which the organic layer was separated. The organic layer was washed with water and then a saturated aqueous sodium chloride solution, dried over anhydrous magnesium sulfate, and then distilled under reduced pressure to remove the solvent. Diisopropyl ether was added to the residue, and the crystals precipitated were collected by filtration, washed with diisopropyl ether and then dried to obtain 8.30 g of 1-[2-hydroxy-5-(2-hydroxyethyl)-4-methoxyphenyl]-1-ethanone as yellow crystals.

In the same manner as above, 1-[2-hydroxy-4-(2-hydroxyethyl)-5-methoxyphenyl]-1-ethanone was obtained.

NMR (CDCl$_3$) δ values: 1.6-1.8 (1H, m), 2.61 (3H, s), 2.90 (2H, t, J=7 Hz), 3.8-4.1 (2H, m), 3.84 (3H, s), 6.84 (1H, s), 7.06 (1H, s), 11.98 (1H, s)

(5) Production of 2-bromo-1-[2-hydroxy-5-(2-hydroxyethyl)-4-methoxyphenyl]-1-ethanone

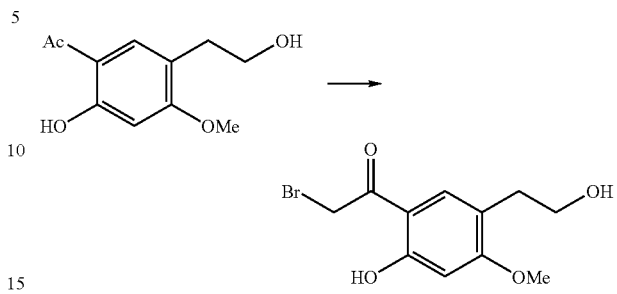

In 100 mL of methylene chloride was dissolved 10.0 g of 1-[2-hydroxy-5-(2-hydroxyethyl)-4-methoxyphenyl]-1-ethanone, and 2.94 mL of bromine was added dropwise to the solution, after which the resulting mixture was stirred at room temperature for 1 hour. The reaction mixture was poured into ice water and the organic layer was separated. The organic layer was washed with water and then a saturated aqueous sodium chloride solution, and dried over anhydrous magnesium sulfate. The solvent was distilled off under reduced pressure to obtain 16.4 g of 2-bromo-1-[2-hydroxy-5-(2-hydroxyethyl)-4-methoxyphenyl]-1-ethanone as a yellow oil.

In the same manner as above, 2-bromo-1-[2-hydroxy-4-(2-hydroxyethyl)-5-methoxyphenyl]-1-ethanone was obtained.

IR (neat) cm$^{-1}$: 3376, 2941, 1644, 1496, 1243, 1034, 757, 690 NMR (CDCl$_3$) δ values: 1.5-1.8 (1H, m), 2.91 (2H, t, J=7 Hz), 3.8-4.1 (2H, m), 3.85 (3H, s) 4.40 (2H, s), 6.89 (1H, s), 7.07 (1H, s) 11.51 (1H, s)

(6) Production of 2-(6-methoxy-1-benzofuran-5-yl)-1-ethanol

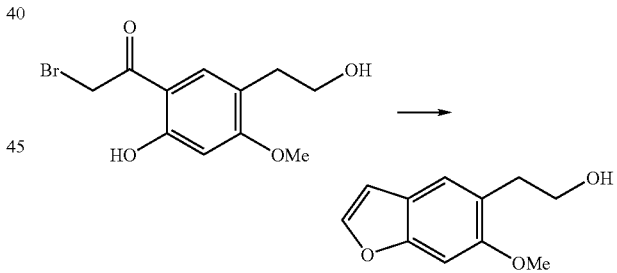

In 70 mL of methanol was dissolved 16.4 g of the aforesaid 2-bromo-1-[2-hydroxy-5-(2-hydroxyethyl)-4-methoxyphenyl]-1-ethanone, and 17.3 g of sodium acetate was added to the solution, after which the resulting mixture was heated under reflux for 5 minutes. After the reaction mixture was cooled, water and ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was dissolved in 150 mL of methanol and to the resulting solution was added 6.30 g of sodium borohydride in small portions, after which the resulting mixture was stirred at room temperature for 1 hour. Then, the resulting solution was adjusted to pH 1 with 6 mol/L hydrochloric acid and stirred at room temperature for another 1 hour. The reaction mixture was concentrated under reduced pressure and water and ethyl acetate were added thereto, after which the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; hexane:ethyl acetate=4:1) to obtain 1.48 g of 2-(6-methoxy-1-benzofuran-5-yl)-1-ethanol as light-yellow crystals.

NMR (CDCl$_3$) δ values: 1.79 (1H, brs), 2.97 (2H, t, J=7 Hz), 3.84 (2H, t, J=7 Hz), 3.86 (3H, s), 6.66 (1H, d, J=3 Hz), 7.03 (1H, s), 7.35 (1H, s), 7.51 (1H, d, J=3 Hz)

In the same manner as above, 2-(5-methoxy-1-benzofuran-6-yl)-1-ethanol was obtained.

NMR (CDCl$_3$) δ values: 2.04 (1H, brs), 2.98 (2H, t, J=6 Hz), 3.86 (2H, t, J=6 Hz), 3.86 (3H, s), 6.68 (1H, d, J=2 Hz), 7.02 (1H, s), 7.31 (1H, s), 7.55 (1H, d, J=2 Hz)

(7) Production of 2-[2-(6-methoxy-1-benzofuran-5-yl)ethoxy]acetic acid

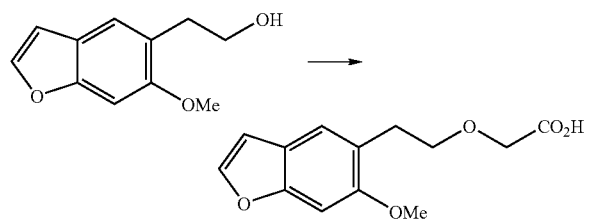

In a mixture of 7.0 mL of tert-butanol and 1.75 mL of N,N-dimethylformamide was dissolved 1.75 g of 2-(6-methoxy-l-benzofuran-5-yl)-1-ethanol, and 2.2 g of 1-chloroacetylpiperidine and 1.54 g of potassium tert-butoxide were added to the solution under ice-cooling, after which the resulting mixture was stirred at the same temperature for 30 minutes and then at the room temperature for 2 hours. Water and ethyl acetate were added to the reaction mixture and the pH was adjusted to 1 with 6 mol/L hydrochloric acid, after which the organic layer was separated. The organic layer was washed with water and then a saturated aqueous sodium chloride solution, dried over anhydrous magnesium sulfate, and then distilled under reduced pressure to remove the solvent. The residue was dissolved in 10.5 mL of a 90% aqueous ethanol solution, followed by adding thereto 0.91 g of sodium hydroxide, and the resulting mixture was heated under reflux for 3 hours. After the reaction mixture was cooled, water and ethyl acetate were added thereto and the pH was adjusted to 1 with 6 mol/L hydrochloric acid, after which the organic layer was separated. The organic layer was washed with water and then a saturated aqueous sodium chloride solution, dried over anhydrous magnesium sulfate, and then distilled under reduced pressure to remove the solvent. Diisopropyl ether was added to the residue, and the crystals precipitated were collected by filtration, washed with diisopropyl ether and then dried to obtain 1.42 g of 2-[2-(6-methoxy-1-benzofuran-5-yl)ethoxy]acetic acid as yellow crystals.

IR (neat) cm$^{-1}$: 2939, 1734, 1426, 1252, 1200, 1148, 1094, 1022, 771 NMR (DMSO-d$_6$) δ values: 2.88 (2H, t, J=7 Hz), 3.64 (2H, t, J=7 Hz), 3.82 (3H, s), 4.01 (2H, s), 6.81 (1H, d, J=2 Hz), 7.22 (1H, s), 7.44 (1H, s), 7.82 (1H, d, J=2 Hz)

In the same manner as above, 2-[2-(5-methoxy-1-benzofuran-6-yl)ethoxy]acetic acid was obtained.

IR (neat) cm$^{-1}$: 2942, 1731, 1466, 1431, 1249, 1132, 1013, 955, 832, 760 NMR (DMSO-d$_6$) δ values: 2.90 (2H, t, J=7 Hz), 3.66 (2H, t, J=7 Hz), 3.82 (3H, s), 4.02 (2H, s), 6.86 (1H, d, J=2 Hz), 7.15 (1H, s), 7.46 (1H, s), 7.88 (1H, d, J=2 Hz)

REFERENCE EXAMPLE 7

Production of 3-[2-(1-benzothiophen-5-yl)ethoxy]propionic acid

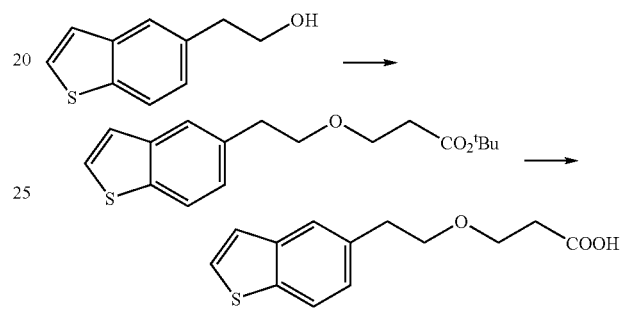

(1) To 4.60 g of 2-(1-benzothiophen-5-yl)-1-ethanol were added 29 mg of potassium hydroxide, 83 mg of tetra-n-butylammonium bromide and 5.67 mL of tert-butyl acrylate, and the resulting mixture was stirred at 45 to 50° C. for 2 hours. After the reaction mixture was cooled, water and toluene were added thereto and the pH was adjusted to 1 with 6 mol/L hydrochloric acid, and the organic layer was separated. The organic layer was washed with water, dried over anhydrous magnesium sulfate, and then distilled under reduced pressure to remove the solvent. The residue was purified by a column chromatography (eluent; hexane ethyl acetate=5:1) to obtain 7.70 g of tert-butyl 3-[2-(1-benzothiophen-5-yl)ethoxy]propionate as a colorless oil.

IR (neat) cm$^{-1}$: 2978, 2867, 1729, 1368, 1159, 1112, 702 NMR (CDCl$_3$) δ values: 1.43 (9H, s), 2.49 (2H, t, J=6 Hz), 2.99 (2H, t, J=7 Hz), 3.70 (2H, t, J=6 Hz), 3.70 (2H, t, J=7 Hz), 7.21 (1H, dd, J=2, 8 Hz), 7.27 (1H, dd, J=1, 5 Hz), 7.41 (1H, d, J=5 Hz), 7.6-7.7 (1H, m), 7.78 (1H, d, J=8 Hz)

(2) In 22.8 mL of toluene was dissolved 7.60 g of tert-butyl 3-[2-(1-benzothiophen-5-yl) ethoxy]propionate, and 94 mg of p-toluenesulfonic acid monohydrate was added thereto, after which the resulting mixture was refluxed for 6 hours. After the reaction mixture was cooled, water and ethyl acetate were added thereto and the organic layer was separated. The organic layer was dried over anhydrous magnesium sulfate and distilled under reduced pressure to remove the solvent. The residue was crystallized from a toluene-cyclohexane mixture (1:4, 23 mL) to obtain 5.30 g of 3-[2-(1-benzothiophen-5-yl)ethoxy]propionic acid as light-red crystals.

IR (KBr) cm$^{-1}$: 2860, 1719, 1273, 1128, 706 NMR (CDCl$_3$) δ values: 2.63 (2H, t, J=6 Hz), 3.00 (2H, t, J=7 Hz), 3.73 (2H, t, J=7 Hz), 3.74 (2H, t, J=6 Hz), 7.20 (1H, dd, J=1, 8 Hz), 7.28 (1H, dd, J=1, 5 Hz), 7.41 (1H, d, J=5 Hz), 7.6-7.7 (1H, m), 7.79 (1H, d, J=8 Hz)

REFERENCE EXAMPLE 8

Production of 3-[2-(1-benzothiophen-5-yl)ethoxy]propionic acid

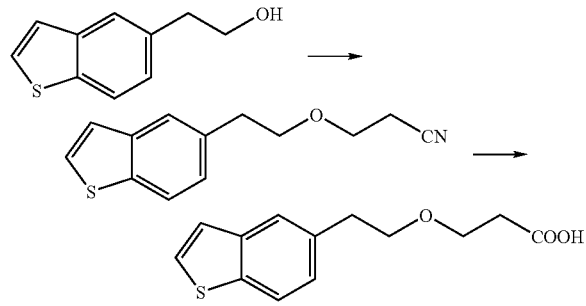

(1) To 2.00 g of 2-(1-benzothiophen-5-yl)-1-ethanol were added 13 mg of potassium hydroxide, 36 mg of tetra-n-butylammonium bromide and 1.11 mL of acrylonitrile, and the resulting mixture was stirred at 45° C. for 3 hours. After the reaction mixture was cooled, water and ethyl acetate were added thereto and the pH was adjusted to 1 with 2 mol/L hydrochloric acid. The insoluble materials were removed and then the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; hexane:ethyl acetate=3:1) to obtain 2.46 g of 3-[2-(1-benzothiophen-5-yl)ethoxy]propiono-nitrile as a colorless oil.

IR (neat) cm$^{-1}$: 2870, 2251, 1114, 757, 704 NMR (CDCl$_3$) δ values: 2.58 (2H, t, J=6 Hz), 3.02 (2H, t, J=7 Hz), 3.66 (2H, t, J=6 Hz), 3.75 (2H, t, J=7 Hz), 7.22 (1H, d, J=8 Hz), 7.29 (1H, d, J=5 Hz), 7.42 (1H, d, J=5 Hz), 7.68 (1H, s), 7.80 (1H, d, J=8 Hz)

(2) In 0.6 mL of acetic acid was dissolved 200 mg of 3-[2-(1-benzothiophen-5-yl)ethoxy]propiononitrile, followed by adding thereto 0.4 mL of water and 0.184 mL of sulfuric acid, and the resulting mixture was stirred at 90 to 100° C. for 1 hour. After the reaction mixture was cooled, water and ethyl acetate were added thereto and the organic layer was separated. The organic layer was washed with water and then a saturated aqueous sodium chloride solution, dried over anhydrous magnesium sulfate, and then distilled under reduced pressure to remove the solvent. The residue was purified by a column chromatography (eluent; toluene ethyl acetate=3:1) to obtain 140 mg of 3-[2-(1-benzothiophen-5-yl)ethoxy]propionic acid as colorless crystals.

REFERENCE EXAMPLE 9

Production of 3-[2-(1-benzothiophen-5-yl)ethoxy]-1-propanol

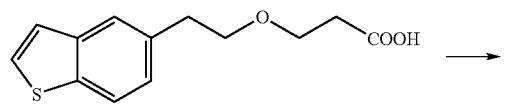

-continued

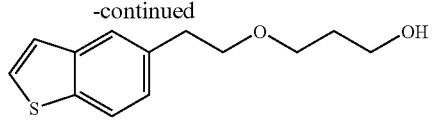

In 8 mL of tetrahydrofuran was dissolved 2.00 g of 3-[2-(1-benzothiophen-5-yl)ethoxy]-1-propionic acid, and 1.31 mL of triethylamine was added thereto. Then, the resulting solution was cooled to −25° C., after which a solution of 0.88 mL of ethyl chloroformate in 2 mL of tetrahydrofuran was added dropwise thereto, and the resulting mixture was stirred at 5° C. for 1 hour. To the reaction mixture were added 15 mL of ethyl acetate and 10 mL of a saturated aqueous sodium chloride solution, and the organic layer was separated. After the organic layer was cooled to 5° C., 0.36 g of sodium borohydride was added thereto and the resulting mixture was stirred at room temperature for 1 hour. To the reaction mixture were added 20 mL of water and 10 mL of ethyl acetate, and the organic layer was separated. The organic layer was washed successively with a 1 mol/L aqueous sodium hydroxide solution, water and a saturated aqueous sodium chloride solution, and then dried over anhydrous magnesium sulfate. The solvent was distilled off under reduced pressure to obtain 1.89 g of 3-[2-(1-benzothiophen-5-yl)ethoxy]-1-propanol as a yellow oil.

REFERENCE EXAMPLE 10

Production of 5-[2-(3-bromopropoxy)ethyl]-1-benzothiophene

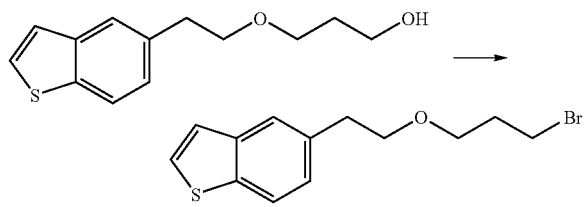

In 40 mL of methylene chloride was dissolved 2.00 g of 3-[2-(1-benzothiophen-5-yl)ethoxy]-1-propanol, and 5.55 g of triphenylphosphine was added to the solution, after which a solution of 8.42 g of carbon tetrabromide in 10 mL of methylene chloride was added dropwise thereto under ice-cooling and the resulting mixture was stirred at room temperature for 20 minutes. To the reaction mixture was added 20 mL of water, and the organic layer was separated. The organic layer was washed with a saturated aqueous sodium hydrogencarbonate solution and then a saturated aqueous sodium chloride solution, dried over anhydrous magnesium sulfate, and then distilled under reduced pressure to remove the solvent. Diethyl ether was added to the residue and the insoluble materials were filtered off, after which the solvent was distilled off under reduced pressure. The residue was purified by a column chromatography (eluent; hexane:ethyl acetate=20:1 to 10:1) to obtain 1.93 g of 5-[2-(3-bromopropoxy)ethyl]-1-benzothiophene as a colorless oil.

IR (neat) cm$^{-1}$: 2863, 1437, 1112, 1051, 701 NMR (CDCl$_3$) δ values: 2.0-2.2 (2H, m), 3.00 (2H, t, J=7 Hz), 3.48 (2H, t, J=6 Hz), 3.58 (2H, t, J=6 Hz), 3.70 (2H, t, J=7 Hz), 7.22 (1H, dd, J=1, 8 Hz), 7.28 (1H, dd, J=1, 5 Hz), 7.42 (1H, d, J=5 Hz), 7.6-7.7 (1H, m), 7.79 (1H, d, J=8 Hz)

REFERENCE EXAMPLE 11

Production of 3-azetidinyl=pivalate hydrochloride

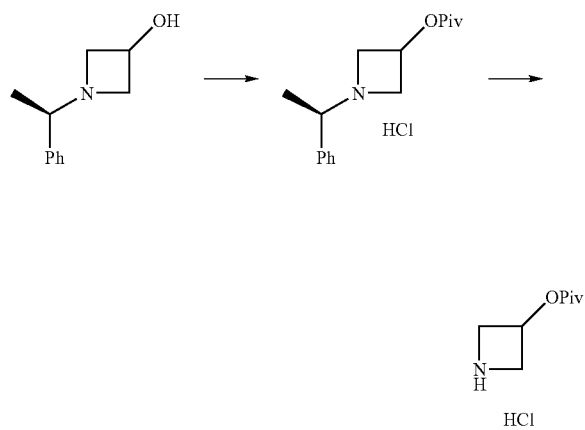

(1) In a mixture of 200 mL of toluene and 100 mL of tert-butanol was dissolved 50.0 g of 1-[(1R)-1-phenylethyl]azetidin-3-ol, and 41.2 g of potassium tert-butoxide was added thereto in small portions under ice-cooling, after which the resulting mixture was stirred at the same temperature for 1.5 hours. Under ice-cooling, 41.7 mL of pivaloyl chloride was added dropwise to the reaction mixture and stirred at the same temperature for 30 minutes. The reaction mixture was poured into 300 mL of water and the insoluble materials were filtered off, after which the organic layer was separated. The organic layer was washed with water and then a saturated aqueous sodium chloride solution, dried over anhydrous magnesium sulfate, and then distilled under reduced pressure to remove the solvent. The oil thus obtained was dissolved in 200 mL of ethyl acetate, and 258 mL of a 1.15 mol/L dried hydrogen chloride-ethyl acetate solution was added thereto at 10° C. and stirred at the same temperature for 20 minutes. The crystals precipitated were collected by filtration to obtain 70.8 g of 1-[(1R)-1-phenylethyl]-3-azetidinyl=pivalate hydrochloride as colorless crystals.

IR (KBr) cm$^{-1}$: 2963, 2509, 2436, 1731, 1284, 1161, 699 NMR (DMSO-d$_6$) δ values: 1.16 (9H, s), 1.49 (3H, d, J=7 Hz), 3.6-4.3 (3H, m), 4.4-4.7 (2H, m), 4.9-5.2 (1H, m), 7.3-7.5 (3H, m), 7.6-7.7 (2H, m)

(2) To a solution of 50.0 g of 1-[(1R)-1-phenylethyl]-3-azetidinyl=pivalate hydrochloride in 250 mL of ethanol was added 5 g of 10% palladium-activated carbon, and the resulting mixture was stirred for 9 hours at 50° C. and atmospheric pressure under a hydrogen atmosphere. After cooling, the insoluble materials were filtered off and the solvent was distilled off under reduced pressure. A mixture of ethyl acetate and hexane (1:2) was added to the residue and the crystals precipitated were collected by filtration to obtain 23.1 g of 3-azetidinyl=pivalate hydrochloride as colorless crystals.

IR (KBr) cm$^{-1}$: 2988, 1718, 1156, 877, 789 NMR (CDCl$_3$) δ values: 1.23 (9H, s), 4.0-4.2 (2H, m), 4.3-4.5 (2H, m), 5.2-5.4 (1H, m)

REFERENCE EXAMPLE 12

Production of 3-(trityloxy)azetidine hydrochloride

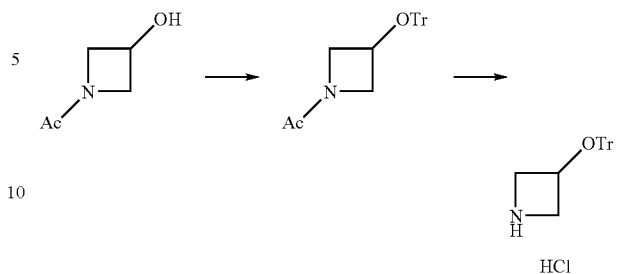

(1) In 50 mL of methylene chloride was dissolved 10.0 g of 1-(3-hydroxy-1-azetidinyl)-1-ethanone, and 31.2 mL of 1,8-diazabicyclo[5,4,0]undec-7-ene and 29.1 g of trityl chloride were added thereto under ice-cooling, after which the resulting mixture was stirred at room temperature for 1 hour. The reaction mixture was poured into 100 mL of ice water and the organic layer was separated. The organic layer was washed with diluted hydrochloric acid, water and a saturated aqueous sodium chloride solution, dried over anhydrous magnesium sulfate, and then distilled under reduced pressure to remove the solvent. Diisopropyl ether was added to the residue and the crystals precipitated were collected by filtration to obtain 21.7 g of 1-[3-(trityloxy)-1-azetidinyl]-1-ethanone as light-yellow crystals.

IR (KBr) cm$^{-1}$: 1646, 1450, 1124, 750, 711 NMR (CDCl$_3$) δ values: 1.74 (3H, s), 3.6-3.8 (4H, m), 4.4-4.5 (1H, m), 7.2-7.5 (15H, m)

(2) In 88 mL of methanol was suspended 22.0 g of 1-[3-(trityloxy)-1-azetidinyl]-1-ethanone, followed by adding thereto 66 mL of a 5 mol/L aqueous sodium hydroxide solution, and the resulting mixture was refluxed for 9 hours. The reaction mixture was distilled under reduced pressure to remove the solvent, and 110 mL of water and 220 mL of ethyl acetate were added to the residue, after which the organic layer was separated. The organic layer was washed with water and then a saturated aqueous sodium chloride solution, dried over anhydrous magnesium sulfate, and then distilled under reduced pressure to remove the solvent. The oil thus obtained was dissolved in 154 mL of ethyl acetate, and to the resulting solution was added 25 mL of a 2.95 mol/L dried hydrogen chloride-ethyl acetate solution, after which the resulting mixture was stirred at room temperature. The crystals precipitated were collected by filtration to obtain 13.7 g of 3-(trityloxy)azetidine hydrochloride as colorless crystals.

IR (KBr) cm$^{-1}$: 2900, 2620, 1447, 751, 700 NMR (DMSO-d$_6$) δ values: 3.4-3.6 (4H, m), 4.3-4.5 (1H, m), 7.2-7.5 (15H, m)

REFERENCE EXAMPLE 13

Production of 3-(tetrahydro-2H-pyran-2-yloxy)azetidine hydrochloride

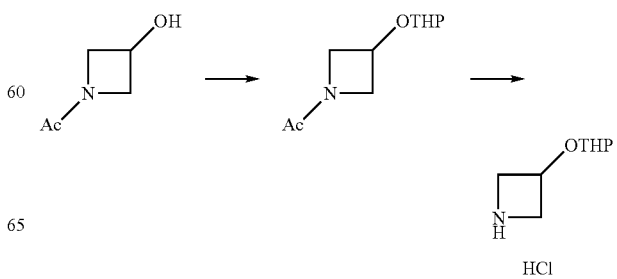

(1) In 10 mL of methylene chloride was dissolved 1.00 g of 1-(3-hydroxy-1-azetidinyl)-1-ethanone, and 1.19 mL of 3,4-dihydro-2H-pyran and 0.08 g of p-toluenesulfonic acid monohydrate were added to the solution, after which the resulting mixture was stirred overnight at room temperature. To the reaction mixture was added 10 mL of water and the pH was adjusted to 8 with a saturated aqueous sodium hydrogencarbonate solution, after which the organic layer was separated. The organic layer was dried over anhydrous magnesium sulfate and distilled under reduced pressure to remove the solvent. The residue was purified by a column chromatography (eluent; chloroform~chloroform:methanol=25:1) to obtain 1.79 g of 1-[3-(tetrahydro-2H-pyran-2-yloxy)-1-azetidinyl]-1-ethanone as a yellow oil.

IR (neat) cm$^{-1}$: 2945, 2875, 1654, 1458, 1138, 1036, 971 NMR (CDCl$_3$) δ values: 1.5-1.9 (6H, m), 1.87 (3H, s) 3.4-3.6 (1H, m), 3.8-4.4 (5H, m), 4.5-4.7 (2H, m)

(2) In the same manner as in Reference Example 12 (2), 3-(tetrahydro-2H-pyran-2-yloxy)azetidine hydrochloride was obtained from 1-[3-(tetrahydro-2H-pyran-2-yloxy)-1-azetidinyl]-1-ethanone.

IR (KBr) cm$^{-1}$: 2956, 2627, 1036, 976, 915 NMR (DMSO-d$_6$) δ values: 1.4-1.8 (6H, m), 3.3-3.5 (1H, m), 3.7-4.2 (5H, m), 4.4-4.7 (2H, m)

REFERENCE EXAMPLE 14

Production of 1-(3-chloropropyl)-3-(trityloxy)azetidine oxalate

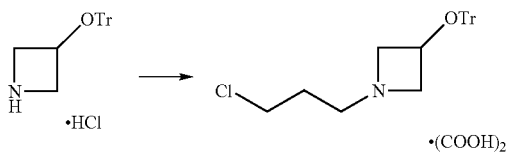

(1) In 5 mL of dimethyl sulfoxide was dissolved 0.50 g of 3-(trityloxy)azetidine hydrochloride, and to the solution were added 0.49 g of potassium carbonate, 0.35 g of potassium iodide and 0.22 mL of 1-bromo-3-chloropropane, after which the resulting mixture was stirred at room temperature for 2 hours. To the reaction mixture were added 15 mL of water and 10 mL of ethyl acetate, and the organic layer was separated. The organic layer was washed with water and then a saturated aqueous sodium chloride solution, and dried over anhydrous magnesium sulfate. The solvent was distilled off under reduced pressure to obtain 1-(3-chloropropyl)-3-(trityloxy)azetidine.

(2) In 10 mL of ethyl acetate was dissolved 1-(3-chloropropyl)-3-(trityloxy)azetidine, and to the resulting solution was added 0.15 g of oxalic acid, after which the resulting mixture was stirred at room temperature. The crystals precipitated were collected by filtration to obtain 0.39 g of 1-(3-chloropropyl)-3-(trityloxy)azetidine oxalate.

IR (KBr) cm$^{-1}$: 3033, 1491, 1449, 1139, 706 NMR (DMSO-d$_6$) δ values: 1.7-1.9 (2H, m), 3.0-3.1 (2H, m), 3.5-3.7 (6H, m), 4.3-4.5 (1H, m), 7.2-7.4 (15H, m)

REFERENCE EXAMPLE 15

Production of 1-(3-chloropropyl)-3-(tetrahydro-2H-pyran-2-yloxy)azetidine

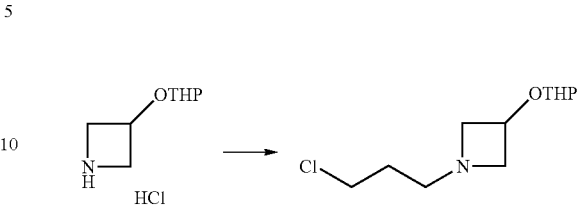

In the same manner as in Reference Example 14 (1), 1-(3-chloropropyl)-3-(tetrahydro-2H-pyran-2-yloxy)azetidine was obtained from 3-(tetrahydro-2H-pyran-2-yloxy)azetidine hydrochloride.

IR (neat) cm$^{-1}$: 2943, 2834, 1203, 1038, 975, 914, 871 NMR (CDCl$_3$) δ values: 1.4-1.8 (6H, m), 1.8-1.9 (2H, m), 2.59 (2H, t, J=7 Hz), 2.8-3.0 (2H, m), 3.4-3.5 (1H, m), 3.57 (2H, t, J=7 Hz), 3.6-3.7 (2H, m), 3.8-3.9 (1H, m), 4.3-4.4 (1H, m), 4.5-4.6 (1H, m)

TEST EXAMPLE 1

[Activity to Accelerate Neurite Outgrowth]

PC12 cells [rat adrenomedullary chromaffinoma (NGF responders)] were cultured in an incubator (5% CO$_2$, 37° C.) by using RPMI1640 medium (available from Nissui Pharmaceutical Co., Ltd.) containing 5% heat inactivated (56° C., 30 minutes) horse serum (available from Bio-Whittaker Inc.), 5% heat inactivated (56° C., 30 minutes) fetal calf serum (available from Sigma Chemical Co.) and 25 μg/ml gentamicin (available from GIBCO BRL).

The cultured PC12 cells were incubated at 37° C. for 30 minutes in phosphate-buffered physiological saline containing 1 mM EDTA, to be detached from a culture flask. The concentration of the cultured PC12 cells was adjusted to 5×10$^4$ cells/mL with RPMI1640 medium containing 1.5% heat inactivated horse serum, 1.5% heat inactivated fetal calf serum and 25 μg/ml gentamicin, and the resulting cell suspension was dispensed in 2 ml portions into 35-mm tissue culture dishes (mfd. by Falcon Inc.) coated with 0.01% polyornithine [dissolved in 150 mM borate buffer (pH 8.4)]. Then, 2.5s-NGF (available from Wako Pure Chemical Industries, Ltd.) [dissolved in phosphate-buffered physiological saline containing 0.1% bovine serum albumin] and each test compound were added to the medium at the same time so as to adjust their final concentrations to 40 ng/mL and 10 μM, respectively, followed by culturing under conditions of 5% CO$_2$ and 37° C. After 48 hours of the culturing, cells were fixed in a 10% neutral formalin solution for 30 minutes, washed with phosphate-buffered physiological saline and distilled water, and then dried. Any four fields of view were selected under a phase contrast microscope, and 50 or more cells were observed in each field of view. The percentage of the number of cells having an neurite extended to a length longer than the diameter of the cell body relative to the total number of cells observed (neurite outgrowth rate) was calculated.

The activity to accelerate neurite outgrowth was calculated according to the following expression as a neurite outgrowth acceleration rate attained by the addition of each test compound, by taking a neutrite outgrowth rate due to NGF as 100%:

(neutrite outgrowth rate attained by addition of each test compound)/(neutrite outgrowth rate due to NGF)×100 (%)

As a result, the neutrite outgrowth acceleration rate was found to be as follows: the compound of Example 2: 265%, the compound of Example 6: 300%, the compound of Example 12: 299%, the compound of Example 14: 207%, the compound of Example 29: 212%, the compound of Example 51: 216%, the compound of Example 59: 241%, the compound of Example 69: 233%, the compound of Example 71: 183%, the compound of Example 74: 246%, the compound of Example 80: 190%, and the compound of Example 81: 190%.

TEST EXAMPLE 2

[Activity to Accelerate Nerve Regeneration]

The test was carried out according to the method described in J. Pharmaco. Exp. Ther., Vol. 290, page 348 (1999) and Neuroscience, vol. 88, page 257 (1999).

SD strain rats (male, aged 6 to 7 weeks, and weighing 170 to 280 g) were anesthetized with pentobarbital, and the left sciatic nerve of each rat was exposed in the femoral region, separated from the surrounding connective tissue, and then cut at a distal position which was about 1 cm apart from the gluteus. The ends of the nerve were inserted into a sterilized silicone tube with a length of 8 mm (inside diameter 1.3 mm, and outside diameter 1.8 mm) to a depth of 3.5 mm so that a space of 1 mm might be formed in the middle of the tube. The ends of the nerve were fixed and the nerve was put back to the muscular tissue together with the tube, after which the incised part was sutured. On the seventh day, each test compound dissolved in distilled water was orally administered in a dose of 1 mg/kg, and thereafter the test compound was administered once a day for 13 days in the same manner as above.

Twenty-one days after cutting the nerve, the sciatic nerve was exposed again under pentobarbital anesthesia, and the nerve in the femoral region and the crural region was separated from the surrounding connective tissues, after which the silicone tube at the cut part was removed. A stimulation electrode was set on the proximal side with respect to the cut position, and a recording electrode was set at the most distal position in the crural region. An electric stimulus (voltage: 2 V, delay: 1 msec, and duration: 100 μsec) was given, and an action potential induced by the stimulus was recorded. The recording electrode was gradually moved toward the proximal, and the distance between the cut position and the most distal position at which an action potential had been obtained was measured as regeneration distance. Only distilled water was administered to a control group.

The sciatic nerve regeneration rate of the test compound was calculated according to the following expression:

(regeneration distance of drug-treated group)/(regeneration distance of control group)×100 (%)

As a result, the sciatic nerve regeneration rate was found to be as follows: the compound of Example 4: 167%, the compound of Example 10: 186%, the compound of Example 12: 142%, the compound of Example 14: 150%, the compound of Example 31: 155%, and the compound of Example 33: 161%.

TEST EXAMPLE 3

[Activity to Inhibit the Neuronal Death Induced by Aβ]

Inhibitory effect on the death of cultured neurons induced by Aβ was investigated by modifying the method described in Brain Res., vol. 639, page 240 (1994).

Cerebral cortices isolated from the brains of embryos (aged 17 to 19 days) of Wistar strain rats were sliced, and then neurons were dissociated by trypsin treatment. The cells were seeded into a 48-well tissue culture plate at a density of $1 \times 10^5$ cells per well and cultured under conditions of 5% $CO_2$ and 37° C. on Dulbecco's modified Eagle's medium added B27 supplement (available from GIBCO BRL) and 3.6 mg/mL glucose.

On the 12th to 13th day of the culture, a potassium chloride solution was added to the medium to adjust the final concentration of potassium chloride to 25 mmol/L. Immediately after this addition, each test compound was added to the medium. After 24 hours, Aβ (a peptides comprising 25 to 35 residues) dissolved in distilled water was added to the medium at a final concentration of 20 μmol/L. After another 24 hours, the medium was replaced with Dulbecco's modified Eagle's medium added B27 supplement and 3.6 mg/mL glucose and test compound.

The inhibitory activity of the test compound against the death of cultured neurons was determined by inhibition against the decrease of reducing ability of MMT. That is, MTT assay [J. Immuno. Methods, vol. 65, page 55 (1983)] developed by Mosmann was carried out 48 hours after the medium replacement, and the inhibition rate (%) of the test compound against a decrease of a MTT assay value induced by Aβ was calculated.

Inhibition rate=[(MTT assay value of a group treated with Aβ and the drug)−(MTT assay value of a group treated with Aβ)]/[MTT assay value of an untreated group−MTT assay value of a group treated with Aβ]×100 (%).

As a result, the inhibition rate at a concentration of 1 μM was found to be as follows: the compound of Example 4: 63%, the compound of Example 6: 48%, the compound of Example 10: 42%, the compound of Example 14: 48%, the compound of Example 31: 50%, the compound of Example 33: 54%, the compound of Example 61: 52%, the compound of Example 69: 70%, the compound of Example 74: 50%, and the compound of Example 80: 75%.

TEST EXAMPLE 4

[Metabolism in Human Liver Microsomes]

In a test tube were placed 50 μL of 100 mmol/L potassium phosphate buffer (pH 7.4) and 25 μL of 3 mg protein/mL pooled human liver microsomes (available from Gentest Inc.), and a solution prepared by blending 10 μL of 66 mmol/L sodium glucose 6-phosphate, 10 μL of 10 units/mL glucose 6-phosphate dehydrogenase, 10 μL of 26 mmol/L nicotinamide adenine dinucleotide phosphate oxidized form, 10 μL of 66 mmol/L magnesium chloride and 135 μL of 100 mmol/L potassium phosphate buffer (pH 7.4) was added thereto, followed by preincubation for 5 minutes. Thereto was added 50 μL of each test compound to a concentration of 6 μmol/L to initiate the reaction, and incubation was carried out at 37° C. for 60 minutes (final volume: 300 μL). The reaction was terminated by the addition of 600 μL of acetonitrile, followed by centrifugation at 12000×g and at 4° C. for 15 minutes. The supernatant was separated, concentrated by centrifugation under reduced pressure, and then subjected to high performance liquid chromatography, and the amount of the residual test compound after the metabolic reaction was determined.

The residual rate was calculated by the following equation:

Residual rate (%)=[(peak area due to the test compound after 60 minutes of the reaction)/(peak area due to the test compound in the case of stopping the reaction by adding acetonitrile simultaneously with the addition of the test compound after the preincubation)]×100

As a result, the residual rate was found to be as follows: the compound of Example 4: 80%, the compound of Example 10: 70%, the compound of Example 12: 83%, the compound of Example 14: 75%, the compound of Example 61: 74%, the compound of Example 69: 74%, the compound of Example 71: 80%, and the compound of Example 74: 71%.

INDUSTRIAL APPLICABILITY

The alkyl ether derivative of the general formula [1] or salt thereof of the present invention has excellent activity to accelerate neurite outgrowth, activity to accelerate nerve regeneration and activity to protect neurons, is excellent also in stability to metabolism, and is useful as a therapeutic agent for diseases in central and peripheral nerves.

The invention claimed is:

1. A compound represented by the general formula, or a salt thereof:

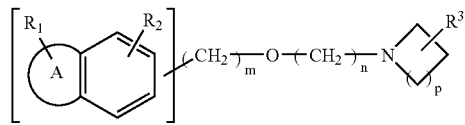

wherein $R^1$ is hydrogen and $R^2$ is halogen or alkoxy,
$R^3$ is a substituted or unsubstituted alkylamino group, or a protected or unprotected amino or hydroxyl group;
the ring A is thiophene;
each of m and n is an integer of 1 to 6; and
p is an integer of 2 or 3.

2. A compound represented by the general formula, or a salt thereof:

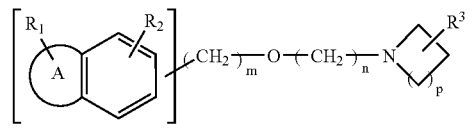

wherein $R^1$ and $R^2$ are both hydrogen,
$R^3$ is a substituted or unsubstituted alkylamino group, or a protected or unprotected amino or hydroxyl group;
the ring A is thiophene;
each of m and n is an integer of 1 to 6; and
p is an integer of 2 or 3.

3. A compound represented by the general formula, or a salt thereof:

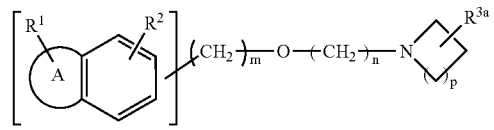

wherein $R^1$ and $R^2$, which may be the same or different, represents one or more groups selected from a hydrogen atom, a halogen atom, alkyl, alkoxy and hydroxyl,
$R^3$ is a substituted or unsubstituted alkylamino group, or a protected or unprotected amino or hydroxyl group;
the ring A is thiophene;
each of m and n is an integer of 1 to 6; and
p is an integer of 2 or 3.

* * * * *